US009732381B2

(12) United States Patent
Stoddart et al.

(10) Patent No.: US 9,732,381 B2
(45) Date of Patent: Aug. 15, 2017

(54) METHOD FOR SEQUENCING A HETEROPOLYMERIC TARGET NUCLEIC ACID SEQUENCE

(75) Inventors: David Stoddart, Oxford (GB); Andrew John Heron, Oxford (GB); Giovanni Maglia, Kessel-Lo (BE); John Hagan Pryce Bayley, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 54 days.

(21) Appl. No.: 13/260,178

(22) PCT Filed: Mar. 25, 2010

(86) PCT No.: PCT/GB2010/000567
§ 371 (c)(1),
(2), (4) Date: Jan. 17, 2012

(87) PCT Pub. No.: WO2010/109197
PCT Pub. Date: Sep. 30, 2010

(65) Prior Publication Data
US 2012/0107802 A1 May 3, 2012

(30) Foreign Application Priority Data
Mar. 25, 2009 (GB) .................... 0905140.0

(51) Int. Cl.
*C12Q 1/68* (2006.01)
(52) U.S. Cl.
CPC .................. *C12Q 1/6869* (2013.01)

(58) Field of Classification Search
None
See application file for complete search history.

(56) References Cited

U.S. PATENT DOCUMENTS

| 5,561,043 A | 10/1996 | Cantor et al. |
| 5,777,078 A | 7/1998 | Bayley et al. |
| 5,795,782 A | 8/1998 | Church et al. |
| 5,817,771 A | 10/1998 | Bayley et al. |
| 5,985,834 A | 11/1999 | Engel et al. |

(Continued)

FOREIGN PATENT DOCUMENTS

| GB | 2130219 | 5/1984 |
| GB | 2453377 | 4/2009 |

(Continued)

OTHER PUBLICATIONS

Khulbe, Pramod K. et al., "DNA translocation through a-hemolysin nanopores with potential application to macromolecular data storage," Journal of Applied Physics, vol. 97(104317):1-7 (2005).

(Continued)

*Primary Examiner* — Robert T Crow
(74) *Attorney, Agent, or Firm* — Nelson Mullins Riley & Scarborough LLP; Jane E. Remillard, Esq.; Adam J. Gastonguay

(57) ABSTRACT

The invention relates to a method for sequencing a heteropolymeric target nucleic acid sequence that involves stochastic sensing. The invention also relates to a method for improving a pore for sequencing a target nucleic acid sequence by modifying one or more sites in the pore.

15 Claims, 11 Drawing Sheets

(56) References Cited

U.S. PATENT DOCUMENTS

| | | | |
|---|---|---|---|
| 6,015,714 | A | 1/2000 | Baldarelli et al. |
| 6,123,819 | A * | 9/2000 | Peeters .................. 204/452 |
| 6,127,166 | A | 10/2000 | Bayley et al. |
| 6,251,610 | B1 | 6/2001 | Gupte et al. |
| 6,362,002 | B1 | 3/2002 | Denison et al. |
| 6,426,231 | B1 | 7/2002 | Bayley et al. |
| 6,451,563 | B1 | 9/2002 | Wittig et al. |
| 6,627,067 | B1 * | 9/2003 | Branton et al. ............ 205/778 |
| 6,824,659 | B2 | 11/2004 | Bayley et al. |
| 6,863,833 | B1 * | 3/2005 | Bloom et al. ............. 216/2 |
| 6,916,665 | B2 | 7/2005 | Bayley et al. |
| 6,927,070 | B1 | 8/2005 | Bayley et al. |
| 7,087,729 | B1 | 8/2006 | Prive |
| 7,189,503 | B2 | 3/2007 | Akeson et al. |
| 8,105,846 | B2 | 1/2012 | Bayley et al. |
| 8,158,344 | B2 | 4/2012 | Haines et al. |
| 8,785,211 | B2 | 7/2014 | Bayley et al. |
| 8,822,160 | B2 | 9/2014 | Bayley et al. |
| 9,447,152 | B2 * | 9/2016 | Clarke ............ C07K 14/245 |
| 2002/0028458 | A1 | 3/2002 | Lexow |
| 2002/0094526 | A1 | 7/2002 | Bayley et al. |
| 2003/0044816 | A1 | 3/2003 | Denison et al. |
| 2003/0087232 | A1 | 5/2003 | Christians et al. |
| 2003/0099951 | A1 | 5/2003 | Akeson et al. |
| 2003/0108902 | A1 | 6/2003 | Abarzua |
| 2003/0118595 | A1 | 6/2003 | Niemeyer et al. |
| 2003/0165936 | A1 | 9/2003 | Rabbani et al. |
| 2003/0166137 | A1 | 9/2003 | Zuker et al. |
| 2003/0211502 | A1 * | 11/2003 | Sauer et al. ............ 435/6 |
| 2003/0215881 | A1 | 11/2003 | Bayley et al. |
| 2004/0214177 | A1 | 10/2004 | Bension |
| 2004/0229315 | A1 | 11/2004 | Lee et al. |
| 2005/0053961 | A1 | 3/2005 | Akeson et al. |
| 2005/0221316 | A1 | 10/2005 | Pedersen et al. |
| 2005/0260655 | A1 | 11/2005 | Liu et al. |
| 2007/0015182 | A1 | 1/2007 | Abarzua |
| 2007/0122885 | A1 | 5/2007 | Reeves et al. |
| 2008/0166724 | A1 | 7/2008 | Gerber et al. |
| 2008/0206252 | A1 | 8/2008 | Pennica et al. |
| 2008/0311582 | A1 * | 12/2008 | Bayley et al. ............ 435/6 |
| 2009/0256116 | A1 | 10/2009 | Shumaker-Parry et al. |
| 2009/0298075 | A1 | 12/2009 | Travers et al. |
| 2010/0221212 | A1 | 9/2010 | Stagliano et al. |
| 2011/0019186 | A1 | 1/2011 | Himmelhaus et al. |
| 2011/0177498 | A1 | 7/2011 | Clarke et al. |
| 2011/0229877 | A1 | 9/2011 | Jayasinghe et al. |
| 2011/0311965 | A1 | 12/2011 | Maglia et al. |
| 2012/0058468 | A1 | 3/2012 | McKeown |
| 2012/0064599 | A1 | 3/2012 | Jayasinghe et al. |
| 2012/0100530 | A1 | 4/2012 | Moysey et al. |
| 2013/0143802 | A1 | 6/2013 | Chilkoti |
| 2013/0195908 | A1 | 8/2013 | Leonetti et al. |
| 2014/0051069 | A1 | 2/2014 | Jayasinghe et al. |
| 2014/0206842 | A1 | 7/2014 | Majeed et al. |
| 2015/0008126 | A1 | 1/2015 | Maglia et al. |
| 2015/0031020 | A1 | 1/2015 | Jayasinghe et al. |
| 2015/0175663 | A1 | 6/2015 | Yokoi et al. |

FOREIGN PATENT DOCUMENTS

| | | |
|---|---|---|
| JP | 11-137260 | 5/1999 |
| WO | 99/05167 A1 | 2/1999 |
| WO | 00/28312 A1 | 5/2000 |
| WO | 01/40516 A2 | 6/2001 |
| WO | 01/42782 A1 | 6/2001 |
| WO | 01/59453 A2 | 8/2001 |
| WO | 02/42496 A2 | 5/2002 |
| WO | 03/021146 A1 | 3/2003 |
| WO | 03/095669 A1 | 11/2003 |
| WO | 2005/056750 A2 | 6/2005 |
| WO | 2006/020775 A2 | 2/2006 |
| WO | 2006/028508 A2 | 3/2006 |
| WO | 2006/100484 A2 | 9/2006 |
| WO | 2007/057668 A1 | 5/2007 |
| WO | 2007/075987 A2 | 7/2007 |
| WO | 2007/084103 A2 | 7/2007 |
| WO | 2008/045575 A2 | 4/2008 |
| WO | 2008/083554 A1 | 7/2008 |
| WO | 2008/102120 A1 | 8/2008 |
| WO | 2008/102121 A1 | 8/2008 |
| WO | 2008/124107 A1 | 10/2008 |
| WO | 2010/004265 A1 | 1/2010 |
| WO | 2010/034018 A2 | 3/2010 |

OTHER PUBLICATIONS

Kocalka, Petr et al., "Rapid and Efficient DNA Strand Cross-Linking by Click Chemistry," ChemBioChem, vol. 9:1280-1285 (2008).

Kolb, Hartmuth C. et al., "Click Chemistry: Diverse Chemical Function from a Few Good Reactions," Angew. Chem. Int. Ed., vol. 40:2004-2021 (2001).

Kovall, Rhett et al., "Toroidal Structure of Lambda-Exonuclease," Science, vol. 277:1824-1827 (1997).

Li, Jiali et al., "DNA molecules and configurations in a solid-state nanopore microscope," Nature, vol. 2:611-615 (2003).

Lovett, Susan T. et al., "Identification and purification of a single-stranded-DNA-specific exonuclease encoded by the recJ gene of *Escherichia coli*," Proc. Natl. Acad. Sci. USA, vol. 86:2627-2631 (1989).

Lovrinovic, Marina et al., "Rapid synthesis of DNA-cysteine conjugates for expressed protein ligation," Biochemical and Biophysical Research Communications, vol. 335:943-948 (2005).

Luo, Kaifu et al., "Influence of Polymer-Pore Interactions on Translocation," Physical Review Letters, vol. 99:148102, DOI: 10.1103/PhysRev Lett. 99.148102, 4 pages, (2007).

Lutz, Jean-Francois et al., "Efficient construction of therapeutics, bioconjugates, biomaterials and bioactive surfaces using azide-alkyne 'click' chemistry," Advanced Drug Delivery Reviews, vol. 60:958-970 (2008).

Martin, Hugh et al., "Nanoscale Protein Pores Modified with PAMAM Dendrimers," J. Am. Chem. Soc., vol. 129:9640-9649 (2007).

Martinez, Javier et al., "The mRNA Cap Structure Stimulates Rate of Poly(A) Removal and Amplifies Processivity of Degradation," The Journal of Biological Chemistry, vol. 276(30):27923-27929 (2001).

Marziali, Andre et al., "New DNA Sequencing Methods," Annu. Rev. Biomed. Eng., vol. 3:195-223 (2001).

Mathé, Jérôme et al., "Orientation discrimination of a single-stranded DNA inside the a-hemolysin membrane channel," PNAS, vol. 102(35):12377-12382 (2005).

Matsuura, Shun-ichi et al., "Real-time observation of a single DNA digestion by l exonuclease under a fluorescence microscope field," Nucleic Acids Research, vol. 29(16):1-5 (2001).

Meller, Amit, "Dynamics of polynucleotide transport through nanometre-scale pores," Journal of Physics: Condensed Matter, vol. 15:R581-R607 (2003).

Meller, Amit et al., "Single molecule measurements of DNA transport through a nanopore," Electrophoresis, vol. 23: 2583-2591 (2002).

Merzlyak, Petr G. et al., "Conductance and Ion Selectivity of a Mesoscopic Protein Nanopore Probed with Cysteine Scanning Mutagenesis," Biophysical Journal, vol. 89:3059-3070 (2005).

Mohammad, Mohammad M. et al., "Controlling a Single Protein in a Nanopore through Electrostatic Traps," J. Am. Chem. Soc., vol. 130:4081-4088 (2008).

Mol, Clifford D. et al., "Structure and function of the multifunctional DNA-repair enzyme exonuclease III," Nature, vol. 374:381-386 (1995).

Movileanu, Llviu et al., "Detecting protein analytes that modulate transmembrane movement of a polymer chain within a single protein pore," Nature Biotechnology, vol. 18:1091-1095 (2001).

Movileanu, Liviu et al., "Location of a Construction in the Lumen of a Transmembrane Pore by Targeted Covalent Attachment of Polymer Molecules," J. Gen. Physiol., vol. 117:239-251 (2001).

(56) References Cited

OTHER PUBLICATIONS

Muller, Joachim et al., "DNA-directed assembly of artificial multienzyme complexes," Biochemical and Biophysical Research Communications, vol. 377:62-67 (2008).
Nakane, Jonathan et al., "A Nanosensor for Transmembrane Capture and Identification of Single Nucleic Acid Molecules," Biophysical Journal, vol. 87:615-621 (2004).
Nakane, Jonathan J. et al., "Nanopore sensors for nucleic acid analysis," J. Phys.: Condens. Matter, vol. 15:R1365-R1393 (2003).
Niemeyer, Christof M. et al., "DNA-Directed Assembly of Bienzymic Complexes from In Vivo Biotinylated NAD(P)H: FMN Oxidoreductase and Luciferase," ChemBioChem., vol. 3:242-245 (2002).
Nwe, Kido et al., "Growing Applications of 'Click Chemistry' for Bioconjugation in Comtemporary Biomedical Research," Cancer Biotherapy and Radiopharmaceuticals, vol. 24(3):289-302 (2009).
Paner, Teodoro M. et al., "Studies of DNA Dumbells. III. Theoretical Analysis of Optical Melting Curves of Dumbells with a 16 Base-Pair Duplex Stem and Tn End Loops (n=2, 3, 4, 5, 6, 8, 10, 14)," Biopolymers, vol. 32(7):881-892 (1992).
Paner, Teodoro M. et al., "Studies of DNA Dumbells. VI. Analysis of Optical Melting Curves of Dumbells with a Sixteen-Base Pair Duplex Stem and End-Loops of Variable Size and Sequence," Biopolymers, vol. 39:779-793 (1996).
Phoenix, David A. et al., "OmpF-LPP Signal Sequence Mutants with Varying Charge Hydrophobicity Ratios Provide Evidence for a Phosphatidylglycerol-Signal Sequence Interaction during Protein Translocation across the *Escherichia coli* Inner Membrane," The Journal of Biological Chemistry, vol. 268(23):17069-17073 (1993).
Sanderson, Katherine, "Standard and Pores. Could the next generation of genetic sequencing machines be built froma collection of miniscule holes?" Nature News, vol. 456(7218):23-25 (2008).
Seeman, Nadrian C., "Nucleic Acid Junctions and Lattices," J. theor. Biol., vol. 99:237-247 (1982).
Seo, Tae Seok et al., "Click Chemistry to Construct Fluorescent Oligonucleotides for DNA Sequencing," J. Org. Chem., vol. 68:609-612 (2003).
Seol, Yeonee, Stretching of Homopolymeric RNA Reveals Single-Stranded Helices and Base-Stacking, Physical Review Letters, vol. 98:158103, DOI: 10.1103/PhysRevLett.98.158103, 4 pages, (2007).
Shank, Lalida P. et al., "Redesigning Channel-Forming Peptides: Amino Acid Substitutions that Enhance Rates of Supramolecular Self-Assembly and Raise Ion Transport Activity," Biophysical Journal, vol. 90:2138-2150 (2006).
Smeets, Ralph M.M. et al., "Salt Dependence of Ion Transport and DNA Translocation through Solid-State Nanopores," Nano Letters, vol. 6(1):89-95 (2006).
Song, Langzhou et al., "Structure of Staphylococcal alpha-Hemolysin, a Heptameric Transmembrane Pore," Science, vol. 274:1859-1866 (1996).
Sutherland, Todd C. et al., "An analysis of mismatched duplex DNA unzipping through a bacterial nanopore," Biochem. Cell Biol., vol. 82:407-412 (2004).
Tadey, Tanya et al., "Capillary electrophoretic separation of nucleotide isomers via complexation with cyclodextrin and borate," Journal of Chromatography B, vol. 657:365-372 (1994).
Thomas, Kirk R. et al., "Processivity of DNA Exonucleases," The Journal of Biological Chemistry, vol. 253(2):424-429 (1978).
Tohda, Koji et al., "Channel Mimetic Sensing Membranes for Nucleotides Based on Multitopic Hydrogen Bonding," Israel Journal of Chemistry, vol. 37:267-275 (1997).
Travers, Kevin J. et al., "A flexible and efficient template format for circular consensus sequencing and SNP detection," Nucleic Acids Research, vol. 38(15):e159, doi:10.1093/nar/gkq543 (2010).
Tung, Ching-Hsuan, "Preparation and Applications of Peptide-Oligonucleotide Conjugates," Bioconjugate Chemistry, vol. 11(5):605-618 (2000).
Van De Goor, Tom A., "Nanopore Detection: Threading DNA Through a Tiny Hole," PharmaGenomics, vol. 4 (3):28-30 (2004).

Walker, Barbara et al., "Key Residues for Membrane Binding, Oligomerization and Pore Forming Activity of Staphylococcal alpha-Hemolysin Identified by Cysteine Scanning Mutagenesis and Targeted Chemical Modification," The Journal of Biological Chemistry, vol. 270 (39):23065-23071 (1995).
Wang, Qian et al., "Bioconjugation by Copper(I)-Catalyzed Azide-Alkyne [3 + 2] Cycloaddition," J. Am. Chem. Soc., vol. 125:3192-3193 (2003).
Wang, Hui et al., "Nanopores with a spark for single-molecule detection," Nature Biotechnology, vol. 19:622-623 (2001).
Wanunu, Meni et al., "DNA Translocation Governed by Interactions with Solid-State Nanopores," Biophysical Journal, vol. 95:4716-4725 (2008).
Wemmer, David E. et al., "Preparation and melting of single strand circular DNA loops," Nucleic Acids Research, vol. 13(23):8611-8621 (1985).
Wolfe, Aaron J. et al., "Catalyzing the Translocation of Polypeptides through Attractive Interactions," J. Am. Chem. Soc., vol. 129:14034-14041 (2007).
Wong, C.T.A. et al., "Polymer capture by electro-osmotic flow of oppositely charged nanopores," The Journal of Chemical Physics, vol. 126:164903-1-164903-6 (2007).
Amblard, Franck et al., "The Cu(I)-catalyzed Huisgen azide-alkyne 1,3-dipolar cycloaddition reaction in nucleotide and oligonucleotide chemistry," Chem. Rev., vol. 109(9):4207-4220 (2009).
Ashkenasy, Nurit et al., "Single Nucleobase Sensitivity of a-Hemolysin (a-HL) Transmembrane Protein Pore: Toward Single DNA Sequencing," ACS National Meeting, vol. 45(13), Abstract No. 74 (2005).
Astier, Yann et al., "Stochastic Detection of Motor Protein-RNA Complexes by Single-Channel Current Recording," ChemPhysChem, vol. 8:2189-2194 (2007).
Bayley, Hagan, "Sequencing single molecules of DNA," Current Opinion in Chemical Biology, vol. 10:628-637 (2006).
Benner, Seico et al., "Sequence-specific detection of individual DNA polymerase complexes in real time using a nanopore," Nature Nanotechnology, vol. 2:718-724 (2007).
Braslavsky, Ido et al., "Sequence information can be obtained from single DNA molecules," PNAS, vol. 100 (7):3960-3964 (2003).
Budanova, Natalia et al., "Heptakis(6-amino-6-deoxy)-beta-cyclodextrin as a chiral selector for the separation of anionic analyte enantiomers by capillary electrophoresis," Electrophoresis, vol. 25:2795-2800 (2004).
Busam, Robert D., "Structure of *Escherichia coli* exonuclease I in complex with thymidine 5'-monophosphate," Acta Cryst., vol. D64:206-210 (2008).
Butler, Tom Z. et al., "Determination of RNA Orientation during Translocation through a Biological Nanopore," Biophysical Journal, vol. 90:190-199 (2006).
Chan, Eugene Y., "Advances in sequencing technology," Mutation Research, vol. 573:13-40 (2005).
Cheley, Stephen et al., "A functional protein pore with a 'retro' transmembrane domain," Protein Science, vol. 8:1257-1267 (1999).
Cheley, Stephen et al., "A Genetically Encoded Pore for the Stochastic Detection of a Protein Kinase," ChemBioChem, vol. 7:1923-1927 (2006).
Cheley, Stephen et al., "Spontaneous oligomerization of a staphylococcal alpha-hemolysin conformationally constrained by removal of residues that form the transmembrane beta-barrel," Protein Engineering, vol. 10 (12):1433-1443 (1997).
Cheley, Stephen et al., "Stochastic Sensing of Nanomolar Inositol 1,4,5-Triphosphate with an Engineered Pore," Chemistry & Biology, vol. 9:829-838 (2002).
Chen, Peng et al., "Atomic Layer Deposition to Fine-Tune the Surface Properties and Diameters of Fabricated Nanopores," Nano Letters, vol. 4(7):1333-1337 (2004).
Chen, Min et al., "Outer membrane protein G: Engineering a quiet pore for biosensing," PNAS, vol. 105 (17):6272-6277 (2008).
Cockroft, Scott L. et al., "A Single-Molecule Nanopore Device Detects DNA Polymerase Activity with Single-Nucleotide Resolution," J.Am. Chem. Soc., vol. 130:818-820 (2008).
Comai, Massimiliano et al., "Protein engineering modulates the transport properties and ion selectivity of the pores formed by

(56) References Cited

OTHER PUBLICATIONS staphylococcal y-haemolysins in lipid membranes," Molecular Microbiology, vol. 44(5):1251-1267 (2002).
Cudic, Predrag et al., "Binding of Nucleotides in Water by Phenathridinium Bis(intercaland) Receptor Molecules," J. Chem. Soc., Chem. Commun., pp. 1073-1075 (1995).
Dapprich, Johannes, "Single-Molecule DNA Digestion by Lambda-Exonuclease," Cytometry, vol. 36:163-168 (1999).
Deamer, David W. et al., "Characterization of Nucleic Acids by Nanopore Analysis," Ac. Chem. Res., vol. 35:817-825 (2002).
Deamer, David W. et al., "Nanopores and nucleic acids: prospects for ultrarapid sequencing," TIBTECH, vol. 18:147-151 (2000).
Dorre, Klaus et al., "Techniques for single molecule sequencing," Bioimaging, vol. 5:139-152 (1997).
Eid, John et al., "Real-Time DNA Sequencing from Single Polymerase Molecules," Science, vol. 323:133-138 (2009).
Eliseev, Alexey V. et al., "Aminocyclodextrins as Selective Hosts with Several Binding Sites for Nucleotides," Angew. Chem. Int. Ed. Engl., vol. 32(9):1331-1333 (1993).
Eliseev, Alexey V. et al., "Molecular Recognition of Nucleotides, Nucleosides, and Sugars by Aminocyclodextrins," J. Am. Chem. Soc., vol. 116:6081-6088 (1994).
Erie, Dorothy et al., "A Dumbell-Shaped, Double-Hairpin Structure of DNA: A Thermodynamic Investigation," Biochemistry, vol. 26:7150-7159 (1987).
Flomembom, O. et al., Single stranded DNA translocation through a nanopore: A master equation approach, Physical Review E, vol. 68:041910, DOI: 10.1103/PhysRevE.68.041910, 7 pages, (2003).
Flusberg, Benjamin A. et al., "Direct detection of DNA methylation during single-molecule, real-time sequencing," Nature Methods, vol. 7(6):461-465 (2010).
Genschel, Jochen et al., "Interaction of E. coli Single-Stranded DNA Binding Protein (SSB) with Exonuclease I. The Carboxy-Terminus of SSB Is the Recognition Site fo the Nuclease," Biol. Chem., vol. 381:183-192 (2000).
Gershow, Marc et al., "Recapturing and trapping single molecules with a solid-state nanopore," Nature Nanotechnology, vol. 2:775-779 (2007).
Ghosal, Sandip, "Electrokinetic-flow-induced viscous drag on a tethered DNA inside a nanopore," Physical Review E, vol. 76:061916, DOI: 10.1103/PhysRevE.76.061916, 3 pages, (2007).
Gu, Li-Qun et al., "Electroosmotic enhancement of the binding of a neutral molecule to a transmembrane pore," PNAS, vol. 100(26):15498-15503 (2003).
Han, Jongyoon et al., "Characterization and Optimization of an Entropic Trap for DNA Separation," Anal. Chem., vol. 74:394-401 (2002).
Han, Eugene S. et al., "RecJ exonuclease: substrates, products and interaction with SSB," Nucleic Acids Research, vol. 34(4):1084-1091 (2006).
Hein, Christopher D. et al., "Click Chemistry, a Powerful Tool for Pharmaceutical Sciences," Pharm. Res., vol. 25 (10):2216-2230 (2008).
Henrickson, Sarah E. et al., "Driven DNA Transport into an Asymmetric Nanometer-Scale Pore," Physical Review Letters, vol. 85(14):3057-3060 (2000).
Holden, Matthew A. et al., "Direct Introduction of Single Protein Channels and Pores into Lipid Bilayers," J. Am. Chem. Soc., vol. 127:6502-6503 (2005).
Holden, Matthew A. et al., "Functional Bionetworks from Nanoliter Water Droplets," J. Am. Chem. Soc., vol. 129:8650-8655 (2007).
Hornblower, Breton et al., "Single-molecule analysis of DNA-protein complexes using nanopores," Nature Methods, vol. 4(4):315-317 (2007).
Howorka, Stefan et al., "DNA Duplex Formation of Individual DNA Strands within a Single Protein Pore," Biophysical Journal, vol. 82(1, pt. 2):508a, No. 2482—Plat (2002).
Howorka, S. et al., "Improved Protocol for High-Throughput Cysteine Scanning Mutagenesis," Biotechniques, vol. 25(5):764-766 (1998).
Howorka, Stefan et al., "Kinetics of duplex formation for individual DNA strands within a single protein nanopore," PNAS, vol. 98(23):12996-13001 (2001).
Howarka, Stefan et al., "Probing Distance and Electrical Potential within a Protein Pore with Tethered DNA," Biophysical Journal, vol. 83:3202-3210 (2002).
Howorka, Stefan et al., "Sequence-specific detection of individual DNA strands using engineered nanopores," Nature Biotechnology, vol. 19:636-639 (2001).
Hu, Tao et al., "Theory of DNA translocation through narrow ion channels and nanopores with charged walls," Physical Review E, vol. 78:032901, DOI: 10.1103/PhysRevE.78.032901, 3 pages, (2008).
Hwang, William L. et al., "Electrical Behavior of Droplet Interface Bilayer Networks: Experimental Analysis and Modeling," J. Am. Chem. Soc., vol. 129:11854-11864 (2007).
Jung, Yuni et al., "The Internal Cavity of the Staphylococcal alpha-Hemolysin Pore Accommodates ~175 Exogenous Amino Acid Residues," Biochemistry, vol. 44(25):8919-8929 (2005).
Kalisch, Bernd W. et al., "Covalently linked sequencing primer linkers (splinkers) for sequence analysis of restriction fragments (Recombinant DNA; hairpin ligation; synthetic oligodeoxynucleotides; dideoxynucleotides)," Gene, vol. 44:263-270 (1986).
Kang, Xiao-feng et al., "Single Protein Pores Containing Molecular Adapters at High Temperatures," Angew. Chem. Int. Ed., vol. 44:1495-1499 (2005).
Wu, Hai-Chen et al., "Protein Nanopores with Covalently Attached Molecular Adapters," J. Am. Chem. Soc., vol. 129:16142-16148 (2007).
Xie, Hongzhi et al., "Single-Molecule Observation of the Catalytic Subunit of cAMP-Dependent Protein Kinase Binding to an Inhibitor Peptide," Chemistry & Biology, vol. 12:109-120 (2005).
Yamagata, Atsushi et al., "Overexpression, purification and characterization of RecJ protein from Thermus thermophilus HB8 and its core domain," Nucleic Acids Research, vol. 29(22):4617-4624 (2001).
International Preliminary Report on Patentability and Written Opinion for Application No. PCT/GB2009/001679, 6 pages, dated Jan. 11, 2011.
International Search Report for Application No. PCT/GB2009/001679, 3 pages, dated Nov. 5, 2009.
International Preliminary Report on Patentability for Application No. PCT/GB2006/004265, 7 pages, dated May 20, 2008.
International Preliminary Report on Patentability for Application No. PCT/GB2008/003372, 6 pages, dated Apr. 7, 2010.
International Search Report for Application No. PCT/GB2009/001690, 3 pages, dated Oct. 13, 2009.
International Preliminary Report on Patentability and Written Opinion for Appliction No. PCT/GB2009/001690, 9 pages, dated Jan. 11, 2011.
Akeson, Mark et al., "Microsecond Time-Scale Discrimination Among Polycytidylic Acid, Polyadenylic Acid, and Polyuridylic Acid as Homopolymers or as Segments Within Single RNA Molecules," Biophysical Journal, vol. 77:3227-3233 (1999).
Ashkenasy, Nurit et al., "Recognizing a Single Base in an Individual DNA Strand: A Step Toward DNA Sequencing in Nanopores," Angew. Chem. Int. Ed., vol. 44:1401-1404 (2005).
Astier, Yann et al., "Toward Single Molecule DNA Sequencing: Direct Identification of Ribonucleoside and Deoxyribonucleoside 5'-Monophosphates by Using an Engineered Protein Nanopore Equipped with a Molecular Adapter," J. Am. Chem. Soc., vol. 128:1705-1710 (2006).
Bayley, Hagan et al., "Stochastic sensors inspired by biology," Nature, vol. 413:226-230 (2001).
Braha, Orit et al., "Carriers versus Adapters in Stochastic Sensing," ChemPhysChem., vol. 6:889-892 (2005).
Braha, Orit et al., "Designed protein pores as components for biosensors," Chemistry & Biology, vol. 4:497-505 (1997).
Branton, Daniel et al., "The potential and challenges of nanopore sequencing," Nat. Biotechnol., vol. 26 (10):1146-1153 (2008).

(56) References Cited

OTHER PUBLICATIONS

Butler, Tom Z. et al., "Single-molecule DNA detection with an engineered MspA protein nanopore," PNAS, vol. 105 (52):20647-20652 (2008).
Clarke, James et al., "Continuous base identification for single-molecule nanopore DNA sequencing," Nature Nanotechnology, vol. 4:265-270 (2009).
Cockroft, Scott L. et al., "A Single-Molecule Nanopore Device Detects DNA Polymerase Activity with Single-Nucleotide Resolution," J. Am. Chem. Soc., vol. 130:818-820 (2008).
Gu, Li-Qun et al., "Capture of a Single Molecule in a Nanocavity," Science, vol. 291:636-640 (2001).
Gu, Li-Qun et al., "Prolonged Residence Time of a Noncovalent Molecular Adapter, beta-Cyclodextrin, within the Lumen of Mutant alpha-Hemolysin Pores," J. Gen. Physiol., vol. 118:481-493 (2001).
Gu, Li-Qun et al., "Reversal of charge selectivity in transmembrane protein pores by using noncovalent molecular adapters," PNAS, vol. 97(8):3959-3964 (2000).
Gu, Li-Qun et al., "Stochastic sensing of organic analytes by a pore-forming protein containing a molecular adapter," Nature, vol. 398:686-690 (1999).
Guan, Xiyun et al., "Stochastic Sensing of TNT with a Genetically Engineered Pore," ChemBioChem, vol. 6:1875-1881 (2005).
Jayasinghe, Lakmal et al., "The leukocidin pore: Evidence for an octamer with four LukF subunits and four LukS subunits alternating around a central axis," Protein Science, vol. 14:2550-2561 (2005).
Kasianowicz, John J. et al., "Characterization of individual polynucleotide molecules using a membrane channel," Proc. Natl. Acad. Sci. USA, vol. 93:13770-13773 (1996).
Maglia, Giovanni et al., "Enhanced translocation of single DNA molecules through alpha-hemolysin nanopores by manipulation of internal charge," PNAS, vol. 105(50):19720-19725 (2008).
Meller, Amit et al., "Rapid nanopore discrimination between single polynucleotide molecules," PNAS, vol. 97 (3):1079-1084 (2000).
Mitchell, Nick et al., "Chemical Tags Facilitate the Sensing of Individual DNA Strands with Nanopores," Angew. Chem. Int. Ed., vol. 47:5565-5568 (2008).
Purnell, Robert F. et al., "Nucleotide Identification and Orientation Discrimination of DNA Homopolymers Immobilized in a Protein Nanopore," Nano Letters, vol. 8(9):3029-3034 (2008).
Sanchez-Quesada, Jorge et al., "Cyclic Peptides as Molecular Adapters for a Pore-Forming Protein," Journal of the American Chemical Society, vol. 122(48):11757-11766 (2000).
Sanchez-Quesada, Jorge et al., "Single DNA Rotaxanes of a Transmembrane Pore Protein," Angew. Chem. Int. Ed., vol. 43:3063-3067 (2004).
Sauer-Budge, Alexis F. et al., "Unzipping Kinetics of Double-Stranded DNA in a Nanopore," Phys. Rev. Letters, vol. 90(23):238101-1-238101-4 (2003).
Shin, Seong-Ho et al., "Kinetics of a Reversible Covalent-Bond-Forming Reaction Observed at the Single-Molecule Level," Angew. Chem. Int. Ed., vol. 41(19):3707-3709 (2002).
Stoddart, David et al., "Multiple base-recognition sites in a biological nanopore—two heads are better than one," Angew. Chem. Int. Ed. Engl., vol. 49(3):556-559 (2010).
Stoddart, David et al., "Single-nucleotide discrimination in immobilized DNA oligonucleotides with a biological nanopore," PNAS, vol. 106(19):7702-7707 (2009).
Winters-Hilt, Stephen et al., "Highly Accurate Classification of Watson-Crick Basepairs on Termini of Single DNA Molecules," Biophysical Journal, vol. 84:967-976 (2003).
U.S. Appl. No. 12/093,610, filed Jul. 28, 2008, Hagan Bayley.
U.S. Appl. No. 13/338,794, filed Dec. 28, 2011, Hagan Bayley.
U.S. Appl. No. 12/681,643, filed Jun. 15, 2010, John Hagan Bayley.
U.S. Appl. No. 13/002,709, filed May 13, 2011, Lakmal Jayasinghe.
U.S. Appl. No. 13/002,717, filed Mar. 30, 2011, James Clarke.
U.S. Appl. No. 13/129,278, filed Aug. 26, 2011, Giovanni Maglia.
U.S. Appl. No. 13/147,171, filed Nov. 10, 2011, Ruth Moysey.
U.S. Appl. No. 13/147,159, filed Nov. 15, 2011, Brian McKeown.
U.S. Appl. No. 12/093,610, Sep. 27, 2011.
U.S. Appl. No. 12/093,610, Apr. 4, 2011.
U.S. Appl. No. 12/093,610, Sep. 29, 2010.
U.S. Appl. No. 12/093,610, Jan. 22, 2010.
U.S. Appl. No. 12/093,610, Oct. 6, 2009.
U.S. Appl. No. 13/338,794, Mar. 5, 2013.
U.S. Appl. No. 13/338,794, Sep. 24, 2012.
U.S. Appl. No. 13/338,794, Jul. 19, 2012.
U.S. Appl. No. 12/681,643, Nov. 6, 2013.
U.S. Appl. No. 12/681,643, Mar. 8, 2013.
U.S. Appl. No. 12/681,643, Jul. 10, 2012.
U.S. Appl. No. 12/681,643, Dec. 21, 2011.
U.S. Appl. No. 12/681,643, Sep. 6, 2011.
U.S. Appl. No. 13/002,709, Jun. 27, 2013.
U.S. Appl. No. 13/002,709, Dec. 21, 2012.
U.S. Appl. No. 13/002,717, Dec. 20, 2012.
U.S. Appl. No. 13/129,278, Jun. 11, 2013.
U.S. Appl. No. 13/129,278, Feb. 27, 2013.
U.S. Appl. No. 13/147,171, May 6, 2013.
U.S. Appl. No. 13/147,171, Jan. 3, 2013.
U.S. Appl. No. 13/147,159, May 28, 2013.
U.S. Appl. No. 13/147,159, Jan. 25, 2013.
U.S. Appl. No. 13/968,778, filed Aug. 16, 2013, Lakmal Jayasinghe.
U.S. Appl. No. 14/071,731, filed Nov. 5, 2013, Ruth Moysey.
U.S. Appl. No. 13/147,176, Lakmal Jayasinghe, filed Nov. 18, 2011, Mar. 14, 2014.
U.S. Appl. No. 13/338,794, Hagan Bayley, filed Dec. 28, 2011, Mar. 13, 2014.
U.S. Appl. No. 12/681,643, John H. Bayley, filed Jun. 15, 2010, Apr. 24, 2014.
U.S. Appl. No. 13/002,709, Lakmal Jayasinghe, filed May 13, 2011, Mar. 10, 2014.
U.S. Appl. No. 13/002,717, James Clarke, filed Mar. 30, 2011, Apr. 3, 2014.
U.S. Appl. No. 13/129,278, Giovanni Maglia, filed Aug. 26, 2011, Feb. 18, 2014.
U.S. Appl. No. 13/147,159, Brian McKeown, filed Nov. 15, 2011, Dec. 18, 2013.
Bowie, James U. et al., "Deciphering the Message in Protein Sequences: Tolerance to Amino Acid Substitutions," Science, vol. 247:1306-1310 (1990).
Burgess, Wilson H. et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology, vol. 111:2129-2138 (1990).
Kanan, Matthew W. et al., "Reaction discovery enabled by DNA-templated synthesis and in vitro selection," Nature vol. 431:545-549 (2004).
Lazar, Eliane et al., "Transforming Growth Factor alpha: Mutation of Aspartic Acid 47 and Leucine 48 Results in Different Biological Activities," Molecular and Cellular Biology, vol. 8(3):1247-1252 (1988).
U.S. Appl. No. 14/334,285, filed Jul. 17, 2014, Giovanni Maglia.
U.S. Appl. No. 14/455,394, filed Aug. 8, 2014, Lakmal Jayasinghe.
U.S. Appl. No. 13/968,778, Lakmal Jayasinghe, filed Aug. 16, 2013, Mar. 20, 2015.
U.S. Appl. No. 13/968,778, Lakmal Jayasinghe, filed Aug. 16, 2013, Jul. 9, 2014.
U.S. Appl. No. 13/002,717, James Clarke, filed Mar. 30, 2011, Dec. 3, 2014.
U.S. Appl. No. 14/334,285, Giovanni Maglia, filed Jul. 17, 2014, Feb. 9, 2015.
U.S. Appl. No. 13/147,176, Lakmal Jayasinghe, filed Nov. 18, 2011, May 8, 2015.
U.S. Appl. No. 13/147,176, Lakmal Jayasinghe, filed Nov. 18, 2011, Oct. 20, 2014.
Avrameas et al., "The Cross-Linking of Proteins with Glutaraldehyde and its use for the Preparation of Immunoadsorbants," Immunochemistry, vol. 6, pp. 43-52, (1969).
U.S. Appl. No. 13/147,176, Lakmal Jayasinghe, filed Nov. 18, 2011, Aug. 31, 2015.
U.S. Appl. No. 14/858,138, filed Sep. 18, 2015, L. Jayasinghe.

(56) References Cited

OTHER PUBLICATIONS

U.S. Appl. No. 13/147,159, B. Mckeown, filed Nov. 15, 2011, Oct. 20, 2015.
U.S. Appl. No. 14/455,394, L. Jayasinghe, filed Aug. 8, 2014, Oct. 2, 2015.
U.S. Appl. No. 15/390,806, filed Dec. 27, 2016, Brian Mckeown.

* cited by examiner

5'-ACTACCTAGTTTACGTAATCCATCTGCACAATGCAGCATTBtn-3' (SEQ ID NO: 50)
5'-ACTACCTAGTTTACGTAATCCATCTGTACAATGCAGCATTBtn-3' (SEQ ID NO: 48)
5'-ACTACCTAGTTTACGTAATCCATCTGAACAATGCAGCATTBtn-3' (SEQ ID NO: 47)
5'-ACTACCTAGTTTACGTAATCCATCTGGACAATGCAGCATTBtn-3' (SEQ ID NO: 49)

| Oligo | E111N/K147N ($I_0$= 172 ± 1 pA) | | | |
|---|---|---|---|---|
| | C | T | A | G |
| $I_{RES}$ (%) | 35.7 ± 0.1 | 36.6 ± 0.1 | 37.9 ± 0.1 | 38.6 ± 0.1 |

METHOD FOR SEQUENCING A HETEROPOLYMERIC TARGET NUCLEIC ACID SEQUENCE

GOVERNMENT LICENSE RIGHTS

This invention was made with government support under Grant No. R01 HG003709 awarded by NIH/NIAAA. The government has certain rights in this invention.

RELATED APPLICATIONS

This application is a 35 U.S.C. §371 national stage filing of PCT Application No. PCT/GB2010/000567 filed on Mar. 25, 2010, which claims priority to Great Britain Patent Application No. UK 0905140.0 filed Mar. 25, 2009. The contents of the aforementioned applications are hereby incorporated by reference.

FIELD OF THE INVENTION

The invention relates to a method for sequencing a heteropolymeric target nucleic acid sequence that involves stochastic sensing. The invention also relates to a method for improving a pore for sequencing a target nucleic acid sequence by modifying one or more sites in the pore.

BACKGROUND OF THE INVENTION

Stochastic detection is an approach to sensing that relies on the observation of individual binding events between analyte molecules and a receptor. Stochastic sensors can be created by placing a single pore of nanometer dimensions in an insulating membrane and measuring voltage-driven ionic transport through the pore in the presence of analyte molecules. The frequency of occurrence of fluctuations in the current reveals the concentration of an analyte that binds within the pore. The identity of an analyte is revealed through its distinctive current signature, notably the duration and extent of current block (Braha, O., Walker, B., Cheley, S., Kasianowicz, J. J., Song, L., Gouaux, J. E., and Bayley, H. (1997) *Chem. Biol.* 4, 497-505; and Bayley, H., and Cremer, P. S. (2001) *Nature* 413, 226-230).

Engineered versions of the bacterial pore forming toxin α-hemolysin (α-HL) have been used for stochastic sensing of many classes of molecules (Bayley, H., and Cremer, P. S. (2001) *Nature* 413, 226-230; Shin, S., H., Luchian, T., Cheley, S., Braha, O., and Bayley, H. (2002) *Angew. Chem. Int. Ed.* 41, 3707-3709; and Guan, X., Gu, L.-Q., Cheley, S., Braha, O., and Bayley, H. (2005) *Chem. BioChem.* 6, 1875-1881). In the course of these studies, it was found that attempts to engineer α-HL to bind small organic analytes directly can prove taxing, with rare examples of success (Guan and colleague, supra). Fortunately, a different strategy was discovered, which utilised non-covalently attached molecular adaptors, notably cyclodextrins (Gu, L.-Q., Braha, O., Conlan, S., Cheley, S., and Bayley, H. (1999) *Nature* 398, 686-690), but also cyclic peptides (Sanchez-Quesada, J., Ghadiri, M. R., Bayley, H., and Braha, O. (2000) *J. Am. Chem. Soc.* 122, 11758-11766) and cucurbiturils (Braha, O., Webb, J., Gu, L.-Q., Kim, K., and Bayley, H. (2005) *Chem. Phys. Chem* 6, 889-892). Cyclodextrins become transiently lodged in the α-HL pore and produce a substantial but incomplete channel block. Organic analytes, which bind within the hydrophobic interiors of cyclodextrins, augment this block allowing analyte detection (Gu, L.-Q., Braha, O., Conlan, S., Cheley, S., and Bayley, H. (1999) *Nature* 398, 686-690).

There is currently a need for rapid and cheap DNA or RNA sequencing technologies across a wide range of applications. Existing technologies are slow and expensive mainly because they rely on amplification techniques to produce large volumes of nucleic acid and require a high quantity of specialist fluorescent chemicals for signal detection. Stochastic sensing has the potential to provide rapid and cheap DNA sequencing by reducing the quantity of nucleotide and reagents required.

Translocating homopolymer nucleic acid sequences can be distinguished by protein nanopores (for example Branton, D., Deamer, D. W., Marziali, A., Bayley, H., Benner, S. A., Butler, T., Di Ventra, M., Garaj, S., Hibbs, A., Huang, X., et al. (2008) *Nature Biotechnology* 26, 1146-1153). The transition between two homopolymer sequences within a translocating single RNA strand can also be observed (Akeson, M., Branton, D., Kasianowicz, J. J., Brandin, E., & Deamer, D. W. (1999) *Biophys. J.* 77, 3227-3233). Individual base pairs at the end of an immobilized DNA strand can also be identified within a nanopore (Winters-Hilt, S., Vercoutere, W., DeGuzman, V. S., Deamer, D., Akeson, M., & Haussler, D. (2003) *Biophys. J.* 84, 967-976), but it is not clear how this might be adapted for sequencing. Recently, individual modified nucleotide bases have been observed "on the fly" (Mitchell, N. & Howorka, S. (2008) *Angew. Chem. Int. Ed. Engl.* 47, 5565-5568), but these structures were very bulky. There is currently no known method for sequencing heteropolymeric nucleic acid sequences using a nanopore.

SUMMARY OF THE INVENTION

The inventors have surprisingly demonstrated that a pore can discriminate between at least four different nucleotides in a nucleic acid sequence. In other words, the inventors have surprisingly demonstrated that a pore may be used to sequence an intact heteropolymeric target nucleic acid sequence via stochastic sensing.

The inventors have also surprisingly demonstrated that pores having two or more distinct sites that are capable of discriminating between different nucleotides display improved nucleotide recognition. Such pores are advantageous for sequencing nucleic acid sequences. As discussed in more detail below, the presence in a pore of more than one site that is capable of discriminating between different nucleotides not only allows the length of a nucleic acid sequence to be determined, but also allows the sequence of a nucleic acid sequence to be determined more efficiently.

Finally, the inventors have surprisingly demonstrated that pores for sequencing nucleic acids can be improved by modifying at least one site that is capable of discriminating between different nucleotides. If a pore has too few sites that are capable of discriminating between different nucleotides, it can be improved by introducing one or more additional sites. If a pore has too many sites that are capable of discriminating between different nucleotides, it can be improved by removing one or more of the sites. Pores may also be improved by enhancing or reducing the ability of one or more sites to discriminate between different nucleotides.

Accordingly, the invention provides a method for sequencing a heteropolymeric target nucleic acid sequence, comprising:

(a) passing the target sequence through a transmembrane pore so that a proportion of the nucleotides in the target sequence interacts one at a time with at least one site in the pore that is capable of discriminating between different nucleotides; and (b) measuring the current passing through the pore during each interaction and thereby determining the sequence of the target sequence.

The invention also provides:
use of a transmembrane protein pore comprising seven subunits comprising the sequence shown SEQ ID NO: 4 or a variant thereof for sequencing a target nucleic acid sequence;
a method for improving a transmembrane pore for sequencing a target nucleic acid sequence, comprising:
  (a) modifying a transmembrane pore comprising one site that is capable of discriminating between different nucleotides; and
  (b) determining whether or not the resulting pore comprises two or more distinct sites that are capable of discriminating between different nucleotides;
a method for improving a transmembrane pore for sequencing a target nucleic acid sequence, comprising:
  (a) modifying a transmembrane pore comprising more than two distinct sites that are capable of discriminating between different nucleotides; and
  (b) determining whether or not the resulting pore comprises two distinct sites that are capable of discriminating between different nucleotides;
a method for improving a transmembrane pore for sequencing a target nucleic acid sequence, comprising:
  (a) modifying a transmembrane pore comprising more than one distinct site that is capable of discriminating between different nucleotides; and
  (b) determining whether or not the resulting pore comprises one site that is capable of discriminating between different nucleotides;
a method for improving a transmembrane pore for sequencing a target nucleic acid sequence, comprising:
  (a) modifying a transmembrane pore comprising two or more sites that are capable of discriminating between different nucleotides at one of the distinct sites; and
  (b) determining whether or not the ability of one or more of the other distinct sites to discriminate between different nucleotides is altered; and
a pore improved using a method of the invention.

DESCRIPTION OF THE SEQUENCE LISTING

Figure 1:
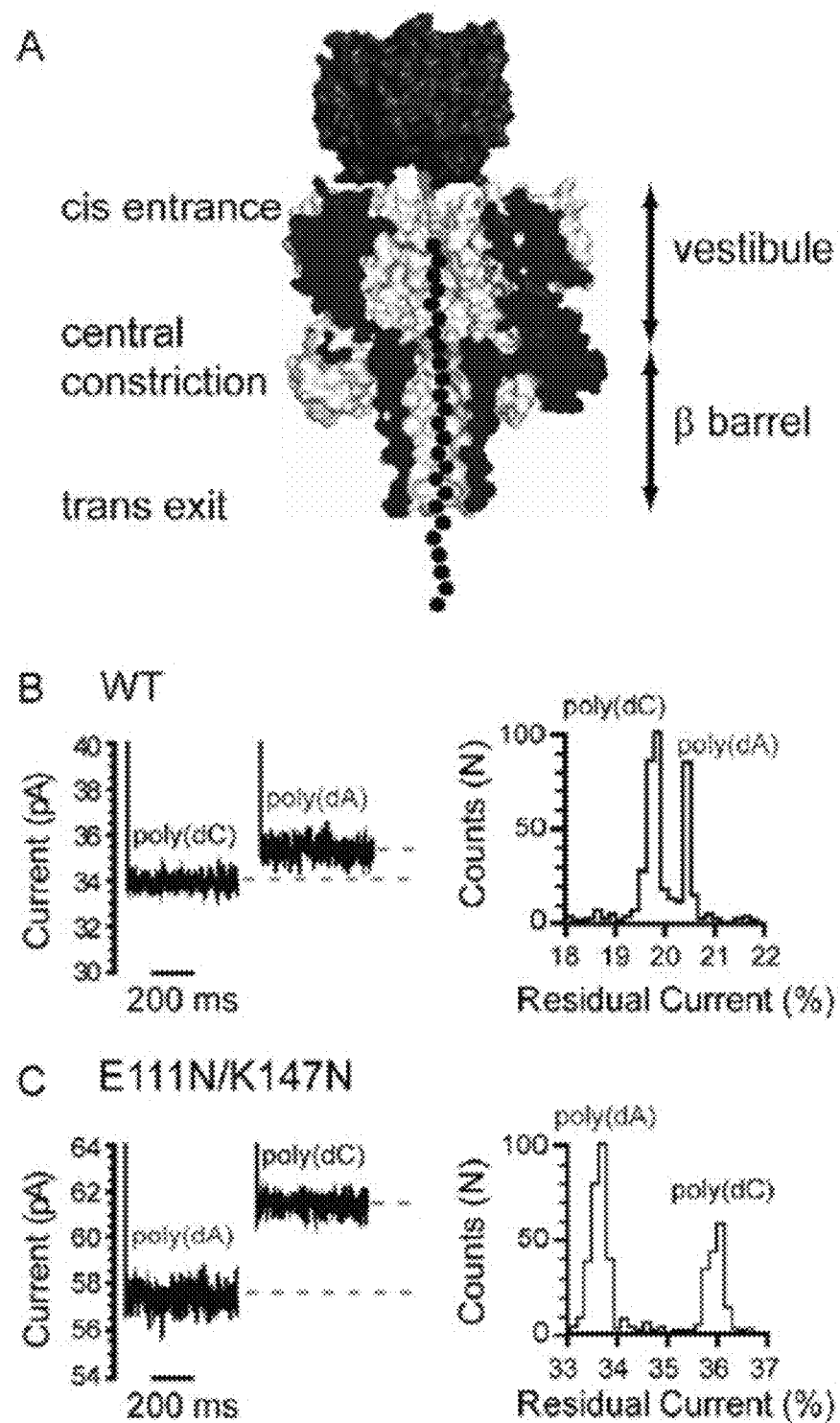
FIG. 1 shows discrimination of immobilized DNA homopolymers by α-HL pores. (A) Schematic representation of a homopolymeric DNA oligonucleotide (blue circles, only the first 25 nucleotides of the 60 nucleotide long sequence are shown) immobilized inside an α-HL pore (grey, cross-section) through the use of a biotin (yellow)-streptavidin (red) linkage. The α-HL pore can be divided into two halves, each approximately 5 nm in length; an upper vestibule located between the cis entrance and the central constriction, and a fourteen-stranded, transmembrane, antiparallel β barrel, located between the central constriction and trans exit. The central constriction of 1.4 nm diameter is formed by the Glu-111, Lys-147 (shaded green) and Met-113 side chains contributed by all seven subunits. (B, C, left). Current levels for the WT and E111N/K147N pores when blocked with immobilized poly(dC) and poly (dA) oligonucleotides. (B, C, right). Typical event histograms displaying the residual current levels, caused by poly(dC) and poly(dA) oligonucleotide blockages, for the WT and E111N/K147N pores. The mean residual current levels for each oligonucleotide were determined by performing Gaussian fits to the data.

SEQ ID NO: 1 shows the polynucleotide sequence encoding one subunit of wild type α-hemolysin (α-HL).

SEQ ID NO: 2 shows the amino acid sequence of one subunit of wild type α-HL. Amino acids 2 to 6, 73 to 75, 207 to 209, 214 to 216 and 219 to 222 form α-helices. Amino acids 22 to 30, 35 to 44, 52 to 62, 67 to 71, 76 to 91, 98 to 103, 112 to 123, 137 to 148, 154 to 159, 165 to 172, 229 to 235, 243 to 261, 266 to 271, 285 to 286 and 291 to 293 form β-strands. All the other non-terminal amino acids, namely 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274 and 287 to 290 form loop regions. Amino acids 1 and 294 are terminal amino acids.

SEQ ID NO: 3 shows the polynucleotide sequence encoding one subunit of α-HL E111N/K147N.

SEQ ID NO: 4 shows the amino acid sequence of one subunit of α-HL E111N/K147N. The same amino acids that form α-helices, β-strands and loop regions in wild type α-HL form the corresponding regions in this subunit.

SEQ ID NO: 5 shows the codon optimised polynucleotide sequence derived from the sbcB gene from E. coli. It encodes the exonuclease I enzyme (EcoExo I) from E. coli.

SEQ ID NO: 6 shows the amino acid sequence of exonuclease I enzyme (EcoExo I) from E. coli. This enzyme performs processive digestion of 5' monophosphate nucleosides from single stranded DNA (ssDNA) in a 3'-5' direction. Amino acids 60 to 68, 70 to 78, 80 to 93, 107 to 119, 124 to 128, 137 to 148, 165 to 172, 182 to 211, 213 to 221, 234 to 241, 268 to 286, 313 to 324, 326 to 352, 362 to 370, 373 to 391, 401 to 454 and 457 to 475 form α-helices. Amino acids 10 to 18, 28 to 26, 47 to 50, 97 to 101, 133 to 136, 229 to 232, 243 to 251, 258 to 263, 298 to 302 and 308 to 311 form β-strands. All the other non-terminal amino acids, 19 to 27, 37 to 46, 51 to 59, 69, 79, 94 to 96 102 to 106, 120 to 123, 129 to 132, 149 to 164, 173 to 181, 212, 222 to 228 233, 242, 252 to 257, 264 to 267, 287 to 297, 303 to 307, 312, 325, 353 to 361, 371, 372, 392 to 400, 455 and 456, form loops. Amino acids 1 to 9 are terminal amino acids. The overall fold of the enzyme is such that three regions combine to form a molecule with the appearance of the letter C, although residues 355-358, disordered in the crystal structure, effectively convert this C into an O-like shape. The amino terminus (1-206) forms the exonuclease domain and has homology to the DnaQ superfamily, the following residues (202-354) form an SH3-like domain and the carboxyl domain (359-475) extends the exonuclease domain to form the C-like shape of the molecule. Four acidic residues of EcoExo I are conserved with the active site residues of the DnaQ superfamily (corresponding to D15, E17, D108 and D186). It is suggested a single metal ion is bound by residues D15 and 108. Hydrolysis of DNA is likely catalyzed by attack of the scissile phosphate with an activated water molecule, with H181 being the catalytic residue and aligning the nucleotide substrate.

SEQ ID NO: 7 shows the codon optimised polynucleotide sequence derived from the xthA gene from E. coli. It encodes the exonuclease III enzyme from E. coli.

SEQ ID NO: 8 shows the amino acid sequence of the exonuclease III enzyme from E. coli. This enzyme performs distributive digestion of 5' monophosphate nucleosides from one strand of double stranded DNA (dsDNA) in a 3'-5' direction. Enzyme initiation on a strand requires a 5' overhang of approximately 4 nucleotides. Amino acids 11 to 13, 15 to 25, 39 to 41, 44 to 49, 85 to 89, 121 to 139, 158 to 160, 165 to 174, 181 to 194, 198 to 202, 219 to 222, 235 to 240 and 248 to 252 form α-helices. Amino acids 2 to 7, 29 to 33, 53 to 57, 65 to 70, 75 to 78, 91 to 98, 101 to 109, 146 to 151, 195 to 197, 229 to 234 and 241 to 246 form β-strands. All the other non-terminal amino acids, 8 to 10, 26 to 28, 34 to 38, 42, 43, 50 to 52, 58 to 64, 71 to 74, 79 to 84, 90, 99, 100, 110 to 120, 140 to 145, 152 to 157, 161 to 164, 175 to 180, 203 to 218, 223 to 228, 247 and 253 to 261, form loops. Amino acids 1, 267 and 268 are terminal amino acids. The enzyme active site is formed by loop regions connecting $\beta_1$-$\alpha_1$, $\beta_3$-$\beta_4$, $\beta_5$-$\beta_6$, $\beta_{III}$-$\alpha_I$, $\beta_{IV}$-$\alpha_{II}$ and $\beta_V$-$\beta_{VI}$ (consisting of amino acids 8-10, 58-64, 90, 110-120, 152-164, 175-180, 223-228 and 253-261 respectively). A single divalent metal ion is bound at residue E34 and aids nucleophilic attack on the phosphodiester bond by the D229 and H259 histidine-aspartate catalytic pair.

SEQ ID NO: 9 shows the codon optimised polynucleotide sequence derived from the recJ gene from T. thermophilus. It encodes the RecJ enzyme from T. thermophilus (TthRecJ-cd).

SEQ ID NO: 10 shows the amino acid sequence of the RecJ enzyme from *T. thermophilus* (TthRecJ-cd). This enzyme performs processive digestion of 5' monophosphate nucleosides from ssDNA in a 5'-3' direction. Enzyme initiation on a strand requires at least 4 nucleotides. Amino acids 19 to 33, 44 to 61, 80 to 89, 103 to 111, 136 to 140, 148 to 163, 169 to 183, 189 to 202, 207 to 217, 223 to 240, 242 to 252, 254 to 287, 302 to 318, 338 to 350 and 365 to 382 form α-helices. Amino acids 36 to 40, 64 to 68, 93 to 96, 116 to 120, 133 to 135, 294 to 297, 321 to 325, 328 to 332, 352 to 355 and 359 to 363 form β-strands. All the other non-terminal amino acids, 34, 35, 41 to 43, 62, 63, 69 to 79, 90 to 92, 97 to 102, 112 to 115, 121 to 132, 141 to 147, 164 to 168, 184 to 188203 to 206, 218 to 222, 241, 253, 288 to 293, 298 to 301, 319, 320, 326, 327, 333 to 337, 351 to 358 and 364, form loops. Amino acids 1 to 18 and 383 to 425 are terminal amino acids. The crystal structure has only been resolved for the core domain of RecJ from *Thermus thermophilus* (residues 40-463). To ensure initiation of translation and in vivo expression of the RecJ core domain a methionine residue was added at its amino terminus, this is absent from the crystal structure information. The resolved structure shows two domains, an amino (2-253) and a carboxyl (288-463) region, connected by a long α-helix (254-287). The catalytic residues (D46, D98, H122, and D183) co-ordinate a single divalent metal ion for nucleophilic attack on the phosphodiester bond. D46 and H120 proposed to be the catalytic pair; however, mutation of any of these conserved residues in the *E. coli* RecJ was shown to abolish activity.

SEQ ID NO: 11 shows the codon optimised polynucleotide sequence derived from the bacteriphage lambda exo (redX) gene. It encodes the bacteriophage lambda exonuclease.

SEQ ID NO: 12 shows the amino acid sequence of the bacteriophage lambda exonuclease. The sequence is one of three identical subunits that assemble into a trimer. The enzyme performs highly processive digestion of nucleotides from one strand of dsDNA, in a 3'-5' direction. Enzyme initiation on a strand preferentially requires a 5' overhang of approximately 4 nucleotides with a 5' phosphate. Amino acids 3 to 10, 14 to 16, 22 to 26, 34 to 40, 52 to 67, 75 to 95, 135 to 149, 152 to 165 and 193 to 216 form α-helices. Amino acids 100 to 101, 106 to 107, 114 to 116, 120 to 122, 127 to 131, 169 to 175 and 184 to 190 form β-strands. All the other non-terminal amino acids, 11 to 13, 17 to 21, 27 to 33, 41 to 51, 68 to 74, 96 to 99, 102 to 105, 108 to 113, 117 to 119, 123 to 126, 132 to 134, 150 to 151, 166 to 168, 176 to 183, 191 to 192, 217 to 222, form loops. Amino acids 1, 2 and 226 are terminal amino acids. Lambda exonuclease is a homo-trimer that forms a toroid with a tapered channel through the middle, apparently large enough for dsDNA to enter at one end and only ssDNA to exit at the other. The catalytic residues are undetermined but a single divalent metal ion appears bound at each subunit by residues D119, E129 and L130.

Figure 7:
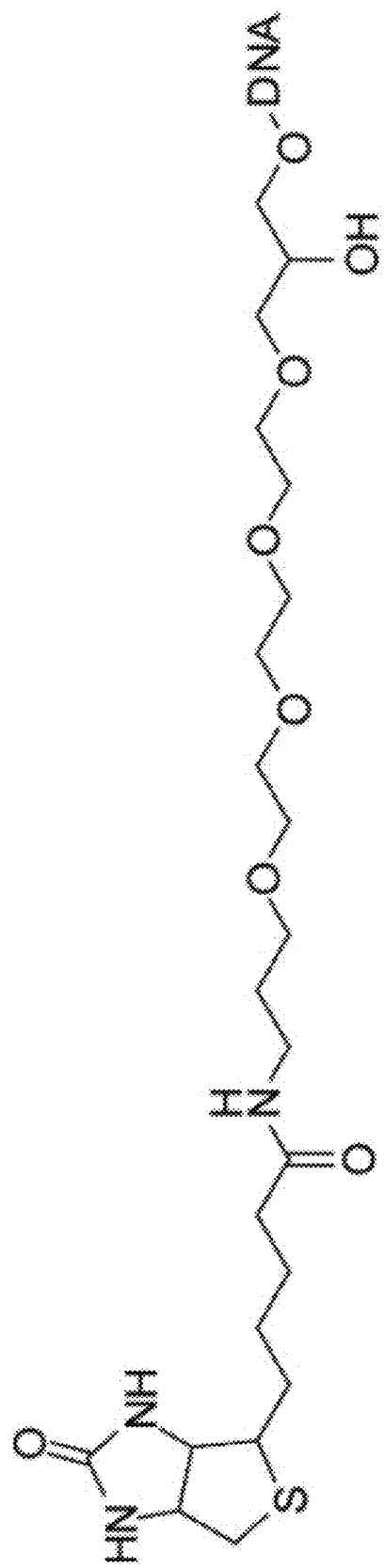
FIG. 7 shows the chemical structure of the biotin-TEG linker used to biotinylate the 3' terminus of the DNA oligonucleotides. The structure was produced with Chem-BioDraw Ultra 11.

SEQ ID NOs: 13 to 66 show the oligonucleotides used in the Examples. When used, all oligonucleotides had a 3' biotin-TEG tag and linker (FIG. 7).

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a nucleotide" includes "nucleotides", reference to "a pore" includes two or more such pores, reference to "an enzyme" includes two or more such enzymes, and the like.

All publications, patents and patent applications cited herein, whether supra or infra, are hereby incorporated by reference in their entirety.

Method of Sequencing Nucleic Acids

The invention provides a method for sequencing a heteropolymeric target nucleic acid sequence. The method comprises (a) passing the target sequence through a transmembrane pore so that a proportion of the nucleotides in the target sequence interacts one at a time with at least one site in the pore that is capable of discriminating between different nucleotides and (b) measuring the current passing through the pore during each interaction and thereby determining the sequence of the target sequence. The nucleotides are identified one at a time sequentially as they interact with at least one site in the pore that is capable of discriminating between different nucleotides. Hence, the method involves stochastic sensing of a proportion of the nucleotides in a target nucleic acid sequence as the nucleotides pass through the barrel or channel of a transmembrane pore in a successive manner in order to sequence the target sequence.

Pores comprising two or more distinct sites that are capable of discriminating between different nucleotides are particularly suited to this method. In order to effectively sequence the nucleic acid, it is important to ensure that the nucleotides in the target sequence are identified in a successive manner. As discussed in more detail below, presence of two or more distinct sites that are capable of discriminating between different nucleotides ensures that the nucleotides in the target sequence are read at least twice. This improves the accuracy of the sequencing.

The method may be carried out using any suitable membrane/transmembrane pore system in which a transmembrane pore is inserted into a membrane. The method is typically carried out using (i) an artificial membrane comprising a transmembrane pore, (ii) an isolated, naturally occurring membrane comprising a transmembrane pore, or (iii) a cell expressing a transmembrane pore. The method is preferably carried out using an artificial membrane. The membrane may comprise other transmembrane and/or intramembrane proteins as well as other molecules in addition to the transmembrane pore used for sequencing.

The membrane forms a barrier to the flow of ions, nucleotides and nucleic acids. The membrane is preferably a lipid bilayer. Lipid bilayers suitable for use in accordance with the invention can be made using methods known in the art. For example, lipid bilayer membranes can be formed using the method of Montal and Mueller (1972). Lipid bilayers can also be formed using the method described in International Application No. PCT/GB08/000,563 and PCT/GB07/002,856.

The method of the invention may be carried out using lipid bilayers formed from any membrane lipid including, but not limited to, phospholipids, glycolipids, cholesterol and mixtures thereof. Any of the lipids described in International Application No. PCT/GB08/000,563 may be used.

Methods are known in the art for inserting pores into membranes, such as lipid bilayers. Some of those methods are discussed above.

The method is typically carried out in vitro.

Heteropolymeric Target Nucleic Acid Sequence

The whole or only part of the target sequence may be sequenced using the method of the invention. The target sequence can be any length. For example, the target sequence can be at least 10, at least 50, at least 100, at least 150, at least 200, at least 250, at least 300, at least 400 or at least 500 nucleotides in length.

The target sequence may form part of a larger nucleic acid sequence. For instance, the target sequence may correspond to a section, such as half, of a larger nucleic acid sequence. The other part(s) of the sequence outside the target sequence do not have to be sequenced in accordance with the invention.

The target sequence used in the method of the invention is an intact sequence. In other words, the target is not cleaved or digested to form shorter nucleic acid sequences or individual nucleotides before it is sequenced in accordance with the invention.

A nucleic acid is a macromolecule comprising two or more nucleotides. The nucleic acid bound by the protein may comprise any combination of any nucleotides. The nucleotides can be naturally occurring or artificial. A nucleotide typically contains a nucleobase, a sugar and at least one phosphate group. The nucleobase is typically heterocyclic. Nucleobases include, but are not limited to, purines and pyrimidines and more specifically adenine, guanine, thymine, uracil and cytosine. The nucleobase may also be 5-methylcytosine or hydroxymethyl-cytosine. The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The nucleotides are preferably selected from AMP, TMP, GMP, CMP, UMP, dAMP, dTMP, dGMP or dCMP.

The nucleotides are typically bonded together in the target sequence via phosphodiester bonds.

The target nucleic acid can be deoxyribonucleic acid (DNA) or ribonucleic acid (RNA). The target nucleic acid may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains.

The target sequence can be single stranded or double stranded. If the target sequence is double stranded, the method preferably involves passing only one strand of the target sequence through the pore. The barrels or channels of many pores, especially transmembrane protein pores, are typically not large enough to allow a double stranded nucleic acid to pass through. Method for separating one strand from a double stranded target sequence and passing it through the pore are discussed in more detail below.

A heteropolymeric target nucleic sequence is one which comprises two or more, such as 3, 4, 5, 6 or more, different nucleotides. The target sequence preferably comprises three or more different nucleotides. The target sequence more preferably comprises four different nucleotides. The four different nucleotides are preferably the four different nucleotides that make up DNA or RNA. In particular, the four different nucleotides preferably independently comprise the nucleobases (a) adenine, (b) guanine, (c) thymine or uracil and (d) cytosine. The target sequence even more preferably comprises five different nucleotides. The five different nucleotides preferably independently comprise the nucleobases (a) adenine, (b) guanine, (c) thymine or uracil, (d) cytosine and (e) 5-methylcytosine.

The method is typically carried out using a target sequence whose sequence is unknown. Alternatively, the method may be carried out using a target sequence whose sequence is known in whole or in part or can be predicted in whole or in part.

The target sequence can be naturally occurring or artificial. For instance, the method may be used to verify the sequence of a manufactured oligonucleotide. The method is typically carried out using a target sequence obtained from or extracted from any organism or microorganism. The organism or microorganism is typically prokaryotic, eukaryotic or an archæon and typically belongs to one the five kingdoms: plantae, animalia, fungi, monera and protista. The method may be carried out on a target sequence obtained from or extracted from any virus. Typically, the target sequence is human in origin, but alternatively it may be from another mammal animal such as from commercially farmed animals such as horses, cattle, sheep or pigs or may alternatively be pets such as cats or dogs.

The target sequence is typically processed prior to undergoing the method, for example by amplification, centrifugation or by passage through a membrane that filters out unwanted molecules or cells, such as red blood cells. The target sequence may be used immediately upon being taken. The target sequence may also be typically stored prior to undergoing the method, preferably below −70° C.

Passing the Target Sequence Through the Pore

The method of the invention involves passing the target sequence through the pore in a controlled and stepwise manner. The target sequence is typically pushed or pulled through the pore. Any method for passing the target sequence through the pore may be used. The target sequence may be passed through the pore cis to trans or trans to cis. The target sequence may be passed through the pore either with or against an applied potential.

The target sequence is preferably passed through the pore using a nucleic acid handling enzyme. The majority of nucleic acid handling enzymes are suitable for use in this application provided they hydrolyse, polymerise or process nucleic acids.

The enzyme may handle single stranded or double stranded nucleic acid. If a transmembrane protein pore is used, the enzyme preferably passes a single strand of the target sequence through the pore. If the target sequence is double stranded, this may be achieved by using an enzyme that separates the two strands of double stranded nucleic acid. For instance, exonucleases that act progressively or processively on double stranded nucleic acids can be used on the cis side of the pore to feed the remaining single strand through under an applied potential or from the trans side under a reverse potential. Likewise, a helicase that unwinds double stranded nucleic acids can also be used in a similar manner.

The method preferably involves contacting the target sequence with a nucleic acid handling enzyme so that the target sequence is passed through a pore at a rate that allows a proportion of the nucleotides in the target sequence to interact one at a time with at least one site in the pore that is capable of discriminating between different nucleotides. Methods for doing this are well known in the art. The rate at which the nucleic acid handling enzyme functions can be altered by mutation compared to a wild type enzyme. For example, variant enzyme with a reduced or improved optimal rate of activity may be used in accordance with the invention. A suitable rate of activity of a nucleic acid handling enzyme in the method of the invention involves handling of from 0.5 to 1000 nucleotides per second, from 0.6 to 500 nucleotides per second, 0.7 to 200 nucleotides per second, from 0.8 to 100 nucleotides per second, from 0.9 to 50 nucleotides per second or 1 to 20 or 10 nucleotides per second. The rate is preferably 1, 10, 100, 500 or 1000 nucleotides per second.

The enzyme also preferably retains at least partial activity at temperatures from 0° C. to 100° C., such as from 10° C. to 60° C. or at room temperature. This allows the sequencing of the target sequence at a variety of temperatures, including room temperature.

A nucleic acid handling enzyme is a polypeptide that is capable of interacting with and modifying at least one property of a nucleic acid. The enzyme preferably modifies the nucleic acid by orienting it or moving it to a specific position.

The nucleic acid handling enzyme is preferably derived from a nucleolytic enzyme or nuclease. The nucleic acid handling enzyme used in the construct of the enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The nucleic acid handling enzyme is more preferably derived from any one of the following enzymes:

3.1.11.—Exodeoxyribonucleases Producing 5'-Phosphomonoesters.
  3.1.11.1 Exodeoxyribonuclease I.
  3.1.11.2 Exodeoxyribonuclease III.
  3.1.11.3 Exodeoxyribonuclease (lambda-induced).
  3.1.11.4 Exodeoxyribonuclease (phage SP3-induced).
  3.1.11.5 Exodeoxyribonuclease V.
  3.1.11.6 Exodeoxyribonuclease VII.
3.1.13.—Exoribonucleases Producing 5'-Phosphomonoesters.
  3.1.13.1 Exoribonuclease II.
  3.1.13.2 Exoribonuclease H.
  3.1.13.3 Oligonucleotidase.
  3.1.13.4 Poly(A)-specific ribonuclease.
  3.1.13.5 Ribonuclease D.
3.1.14.—Exoribonucleases Producing 3'-Phosphomonoesters.
  3.1.14.1 Yeast ribonuclease.
3.1.15.—Exonucleases Active with Either Ribo- or Deoxyribonucleic Acid Producing 5' Phosphomonoesters
  3.1.15.1 Venom exonuclease.
3.1.16.—Exonucleases Active with Either Ribo- or Deoxyribonucleic Acid Producing 3' Phosphomonoesters
  3.1.16.1 Spleen exonuclease.
3.1.21.—Endodeoxyribonucleases Producing 5'-Phosphomonoesters.
  3.1.21.1 Deoxyribonuclease I.
  3.1.21.2 Deoxyribonuclease IV (phage-T(4)-induced).
  3.1.21.3 Type I site-specific deoxyribonuclease.
  3.1.21.4 Type II site-specific deoxyribonuclease.
  3.1.21.5 Type III site-specific deoxyribonuclease.
  3.1.21.6 CC-preferring endodeoxyribonuclease.
  3.1.21.7 Deoxyribonuclease V.
3.1.22.—Endodeoxyribonucleases Producing Other than 5'-Phosphomonoesters.
  3.1.22.1 Deoxyribonuclease II.
  3.1.22.2 *Aspergillus* deoxyribonuclease K(1).
  3.1.22.3 Transferred entry: 3.1.21.7.
  3.1.22.4 Crossover junction endodeoxyribonuclease.
  3.1.22.5 Deoxyribonuclease X.
3.1.25.—Site-Specific Endodeoxyribonucleases Specific for Altered Bases.
  3.1.25.1 Deoxyribonuclease (pyrimidine dimer).
  3.1.25.2 Transferred entry: 4.2.99.18.
3.1.26.—Endoribonucleases Producing 5'-Phosphomonoesters.
  3.1.26.1 *Physarum polycephalum* ribonuclease.
  3.1.26.2 Ribonuclease alpha.
  3.1.26.3 Ribonuclease III.
  3.1.26.4 Ribonuclease H.
  3.1.26.5 Ribonuclease P.
  3.1.26.6 Ribonuclease IV.
  3.1.26.7 Ribonuclease P4.
  3.1.26.8 Ribonuclease M5.
  3.1.26.9 Ribonuclease (poly-(U)-specific).
  3.1.26.10 Ribonuclease IX.
  3.1.26.11 Ribonuclease Z.
3.1.27.—Endoribonucleases Producing Other than 5'-Phosphomonoesters.
  3.1.27.1 Ribonuclease T(2).
  3.1.27.2 *Bacillus subtilis* ribonuclease.
  3.1.27.3 Ribonuclease T(1).
  3.1.27.4 Ribonuclease U(2).
  3.1.27.5 Pancreatic ribonuclease.
  3.1.27.6 *Enterobacter* ribonuclease.
  3.1.27.7 Ribonuclease F.
  3.1.27.8 Ribonuclease V.
  3.1.27.9 tRNA-intron endonuclease.
  3.1.27.10 rRNA endonuclease.
3.1.30.—Endoribonucleases Active with Either Ribo- or Deoxyribonucleic Producing 5' Phosphomonoesters
  3.1.30.1 *Aspergillus* nuclease S(1).
  3.1.30.2 *Serratia marcescens* nuclease.
3.1.31.—Endoribonucleases Active with Either Ribo- or Deoxyribonucleic producing 3' phosphomonoesters
  3.1.31.1 Micrococcal nuclease.

The enzyme is most preferably derived from an exonuclease, such as an exodeoxyribonuclease, which cleaves nucleic acids to form individual nucleotides. The advantages of exodeoxyribonucleases are that they are active on both single stranded and double stranded nucleic acids and hydrolyse bases either in the 5'-3' or 3'-5' direction.

An individual nucleotide is a single nucleotide. The nucleotide may be any of those discussed above. An individual nucleotide is one which is not bound to another nucleotide or nucleic acid by any bond, such as a phosphodiester bond. A phosphodiester bond involves one of the phosphate groups of a nucleotide being bound to the sugar group of another nucleotide. An individual nucleotide is typically one which is not bound in any manner to another nucleic acid sequence of at least 5, at least 10, at least 20, at least 50, at least 100, at least 200, at least 500, at least 1000 or at least 5000 nucleotides.

Preferred enzymes for use in the invention include exonuclease I from E. coli (SEQ ID NO: 6), exonuclease III enzyme from E. coli (SEQ ID NO: 8), RecJ from T. thermophilus (SEQ ID NO: 10) and bacteriophage lambda exonuclease (SEQ ID NO: 12) and variants thereof. Three identical subunits of SEQ ID NO: 12 interact to form a trimer exonuclease. The enzyme is most preferably based on exonuclease I from E. coli (SEQ ID NO: 6).

The nucleic acid handling enzyme preferably comprises any of the sequences shown in SEQ ID NOs: 6, 8, 10 and 12 or a variant thereof. A variant of SEQ ID NO: 6, 8, 10 or 12 is an enzyme that has an amino acid sequence which varies from that of SEQ ID NO: 6, 8, 10 or 12 and which retains nucleic acid handling ability. The ability of a variant to handle nucleic acids can be assayed using any method known in the art. For instance, the ability of a variant to handle nucleic acids can be assayed by contacting the enzyme with a nucleic acid and assaying its ability to orient it or move it to a specific position.

The variant may include modifications that facilitate handling of the nucleic acid and/or facilitate its activity at high salt concentrations and/or room temperature.

The enzyme may be a naturally occurring variant which is expressed by an organism, for instance by an E. coli bacterium. Variants also include non-naturally occurring variants produced by recombinant technology. Over the entire length of the amino acid sequence of SEQ ID NO: 6, 8, 10 or 12, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 6, 8, 10 or 12 over the entire sequence. There may be at least 80%, for example at least 85%, 90% or 95%, amino acid identity over a stretch of 200 or more, for example 230, 250, 270 or 280 or more, contiguous amino acids ("hard homology").

Standard methods in the art may be used to determine homology. For example the UWGCG Package provides the BESTFIT program which can be used to calculate homology, for example used on its default settings (Devereux et al (1984) Nucleic Acids Research 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSP's containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90: 5873-5787. One measure of similarity provided by the BLAST algorithm is the smallest sum probability (P(N)), which provides an indication of the probability by which a match between two amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

Amino acid substitutions may be made to the amino acid sequence of SEQ ID NO: 6, 8, 10 or 12 in addition to those discussed above, for example up to 1, 2, 3, 4, 5, 10, 20 or 30 substitutions. Conservative substitutions may be made, for example, according to Table 1 below.

TABLE 1

Conservative substitutions
Amino acids in the same block in the second column and preferably in the same line in the third column may be substituted for each other.

| NON-AROMATIC | Non-polar | G A P |
| | | I L V |
| | Polar-uncharged | C S T M |
| | | N Q |
| | Polar-charged | D E |
| | | H K R |
| AROMATIC | | H F W Y |

One or more amino acid residues of the amino acid sequence of SEQ ID NO: 6, 8, or 12 may additionally be deleted from the polypeptides described above. Up to 1, 2, 3, 4, 5, 10, 20 or 30 residues may be deleted, or more.

Variants may be fragments of SEQ ID NO: 6, 8, 10 or 12. Such fragments retain nucleic acid handling activity. Fragments may be at least 50, 100, 200 or 250 amino acids in length. A fragment preferably comprises the nucleic acid handling domain of SEQ ID NO: 6, 8, 10 or 12.

One or more amino acids may be alternatively or additionally added to the polypeptides described above. An extension may be provided at the amino terminus or carboxy terminus of the amino acid sequence of SEQ ID NO: 6, 8, 10 or 12 or a variant or fragment thereof. The extension may be quite short, for example from 1 to 10 amino acids in length. Alternatively, the extension may be longer, for example up to 50 or 100 amino acids. A carrier protein may be fused to a subunit or variant.

As discussed above, a variant of SEQ ID NO: 6, 8, 10 or 12 is a protein that has an amino acid sequence which varies from that of SEQ ID NO: 6, 8, 10 or 12 and which retains its ability to handle nucleic acids. A variant typically contains the regions of SEQ ID NO: 6, 8, 10 or 12 that are responsible for handling nucleic acids. The catalytic domains of SEQ ID NOs: 6, 8, 10 or 12 are discussed above in the description of the sequence listing. A variant of SEQ ID NO: 6, 8, 10 or 12 preferably comprises the relevant catalytic domain. A variant SEQ ID NO: 6, 8, 10 or 12 typically includes one or more modifications, such as substitutions, additions or deletions, outside the relevant catalytic domain.

The variant may be modified for example by the addition of histidine or aspartic acid residues to assist its identification or purification or by the addition of a signal sequence to promote their secretion from a cell where the polypeptide does not naturally contain such a sequence.

Other preferred enzymes that are capable of passing the target nucleic acid sequence through the pore include polymerases and helicases. The nucleic acid handling enzyme can be derived from any of these types of enzymes. The polymerase is preferably a member of any of the Enzyme Classification (EC) groups 2.7.7.6, 2.7.7.7, 2.7.7.19, 2.7.7.48 and 2.7.7.49. The polymerase is preferably a DNA-dependent DNA polymerase, an RNA-dependent DNA polymerase, a DNA-dependent RNA polymerase or an RNA-dependent RNA polymerase. The helicase is preferably based on a member of any of the Enzyme Classification (EC) groups 3.6.1.- and 2.7.7.-. The helicase is preferably an ATP-dependent DNA helicase (EC group 3.6.1.8), an ATP-dependent RNA helicase (EC group 3.6.1.8) or an ATP-independent RNA helicase.

The nucleic acid handling enzyme may be labelled with a revealing label. The revealing label may be any suitable label which allows the enzyme to be detected. Suitable labels include, but are not limited to, fluorescent molecules, radioisotopes, e.g. $^{125}I$, $^{35}S$, $^{14}C$, enzymes, antibodies, antigens, polynucleotides and ligands such as biotin.

The nucleic acid handling enzyme may be isolated from an enzyme producing organism, such as *E. coli, T. thermophilus* or bacteriophage, or made synthetically or by recombinant means. For example, the nucleic acid handling enzyme may be synthesised by in vitro translation and transcription. The amino acid sequence of the nucleic acid handling enzyme may be modified to include non-naturally occurring amino acids or to increase the stability of the protein. When the nucleic acid handling enzyme is produced by synthetic means, such amino acids may be introduced during production. The nucleic acid handling enzyme may also be altered following either synthetic or recombinant production.

The nucleic acid handling enzyme may also be produced using D-amino acids. For instance, the nucleic acid handling enzyme may comprise a mixture of L-amino acids and D-amino acids. This is conventional in the art for producing such proteins or peptides.

The nucleic acid handling enzyme may also contain other non-specific chemical modifications as long as they do not interfere with its ability to handle nucleic acids or attach to the pore. A number of non-specific side chain modifications are known in the art and may be made to the side chains of the pores. Such modifications include, for example, reductive alkylation of amino acids by reaction with an aldehyde followed by reduction with $NaBH_4$, amidination with methylacetimidate or acylation with acetic anhydride.

The nucleic acid handling enzyme can be produced using standard methods known in the art. Polynucleotide sequences encoding a nucleic acid handling enzyme may be isolated and replicated using standard methods in the art. Such sequences are discussed in more detail below. Polynucleotide sequences encoding a nucleic acid handling enzyme may be expressed in a bacterial host cell using standard techniques in the art. The nucleic acid handling enzyme may be produced in a cell by in situ expression of the polypeptide from a recombinant expression vector. The expression vector optionally carries an inducible promoter to control the expression of the polypeptide.

Polynucleotide sequences may be isolated and replicated using standard methods in the art. Chromosomal DNA may be extracted from an enzyme producing organism, such as *E. coli, T. thermophilus* or bacteriophage. The gene encoding the enzyme may be amplified using PCR involving specific primers. The amplified sequences may then be incorporated into a recombinant replicable vector such as a cloning vector. The vector may be used to replicate the polynucleotide in a compatible host cell. Thus polynucleotide sequences encoding the enzyme may be made by introducing a polynucleotide encoding the enzyme into a replicable vector, introducing the vector into a compatible host cell, and growing the host cell under conditions which bring about replication of the vector. The vector may be recovered from the host cell. Suitable host cells for cloning of polynucleotides are known in the art and described in more detail below.

The polynucleotide sequence may be cloned into suitable expression vector. In an expression vector, the polynucleotide sequence encoding a construct is typically operably linked to a control sequence which is capable of providing for the expression of the coding sequence by the host cell. Such expression vectors can be used to express a construct.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Multiple copies of the same or different polynucleotide may be introduced into the vector.

The expression vector may then be introduced into a suitable host cell. Thus, a construct can be produced by inserting a polynucleotide sequence encoding a construct into an expression vector, introducing the vector into a compatible bacterial host cell, and growing the host cell under conditions which bring about expression of the polynucleotide sequence. The recombinantly-expressed construct may self-assemble into a pore in the host cell membrane. Alternatively, the recombinant construct produced in this manner may be isolated from the host cell and inserted into another membrane. When producing an oligomeric pore comprising a construct of the invention and at least one different subunit, the construct and different subunits may be expressed separately in different host cells as described above, removed from the host cells and assembled into a pore in a separate membrane, such as a rabbit cell membrane.

The vectors may be for example, plasmid, virus or phage vectors provided with an origin of replication, optionally a promoter for the expression of the said polynucleotide sequence and optionally a regulator of the promoter. The vectors may contain one or more selectable marker genes, for example an ampicillin resistance gene. Promoters and other expression regulation signals may be selected to be compatible with the host cell for which the expression vector is designed. A T7, trc, lac, ara or $\lambda_L$ promoter is typically used. The host cell typically expresses the construct at a high level. Host cells transformed with a polynucleotide sequence encoding a construct will be chosen to be compatible with the expression vector used to transform the cell. The host cell is typically bacterial and preferably *E. coli*. Any cell with a λ DE3 lysogen, for example C41 (DE3), BL21 (DE3), JM109 (DE3), B834 (DE3), TUNER, Origami and Origami B, can express a vector comprising the T7 promoter.

A nucleic acid handling enzyme may be produced in large scale following purification by any protein liquid chromatography system from pore producing organisms or after recombinant expression as described below. Typical protein liquid chromatography systems include FPLC, AKTA systems, the Bio-Cad system, the Bio-Rad BioLogic system and the Gilson HPLC system.

Interaction Between the Nucleotides and Pore

The target sequence is passed through the transmembrane pore so that a proportion of the nucleotides in the target sequence interacts one at a time (i.e. sequentially) with at least one site in the pore that is capable of discriminating between different nucleotides. The sequence of the target sequence may be determined by identifying at least 80%, at least 85%, at least 90%, at least 95%, at least 98% or at least 99% of the nucleotides in the target sequence. Preferably, all of the nucleotides in the target sequence interact with the at least one site and are identified.

The target sequence may be contacted with the pore on either side of the membrane. The target sequence may be introduced to the pore on either side of the membrane. If a nucleic acid handling enzyme is used as discussed above, the target sequence is typically contacted with the side of the membrane on which the enzyme is present. This allows the enzyme to handle the nucleic acid during the method.

A proportion of the nucleotides in the target nucleic acid sequence interacts with at least one site in the pore that is capable of discriminating between different nucleotides as the sequence passes across the membrane through the barrel or channel of the pore. As discussed in more detail below, a proportion of the nucleotides preferably interacts with two or more distinct sites that are capable of discriminating between different nucleotides.

The nucleotides interact with the site(s) capable of discriminating different nucleotides one at a time in a sequential manner. This means that at any one time a site that is capable of discriminating between different nucleotides interacts with only one nucleotide in the target sequence. If the pore comprises two or more distinct sites that are capable of discriminating between different nucleotides, at any one time each of the distinct sites will interact with a different nucleotide in the target sequence. For instance, if the pore comprises two distinct sites that are capable of discriminating between different nucleotides, at any one time the distinct sites will interact with two different nucleotides in the target sequence.

The target sequence is passed through the pore one nucleotide at a time and each nucleotide is identified sequentially. Hence, at one time point, each of the distinct sites that are capable of discriminating between different nucleotides interacts with a different nucleotide in the target sequence. At the next time point, the target sequence is passed one nucleotide further through the pore and each of the distinct sites that are capable of discriminating between different nucleotides interacts with the a nucleotide that is adjacent to the nucleotide with which it interacted at the previous time point. If there are two or more distinct sites in the pore, a selected nucleotide in the target sequence will interact with each distinct site in a sequential manner as it passed through the pore.

The current passing through the pore is measured during each interaction and this allows the identity of the nucleotide interacting with the site(s) to be determined. Identification of a proportion of the nucleotides in the target sequence in a successive manner allows the sequence of the target sequence to be determined.

The nucleotides may interact with the pore in any manner and at any site. The nucleotides preferably reversibly bind to the sites(s) in the pore capable of discriminating between different nucleotides. The nucleotides most preferably reversibly bind to the site(s) in the pore in the pore as they pass through the pore across the membrane. The nucleotides can reversibly bind to the site(s) via or in conjunction with an adaptor that facilitates an interaction between the pore and the nucleotide. Preferably however, the pore does not contain a molecular adaptor that facilitates an interaction between the pore and nucleotides.

During the interaction between the nucleotide and a site capable of discriminating between different nucleotides, the nucleotide affects the current flowing through the pore in a manner specific for that nucleotide. For example, a particular nucleotide will reduce the current flowing through the pore to a particular extent. In other words, the current flowing through the pore is distinctive for the interaction between a particular nucleotide and a site capable of discriminating between different nucleotides. Hence, when different nucleotides move through the pore and interact with the pore in a successive manner, the current flowing through the pore changes for each interaction.

If two or more distinct sites that are capable of discriminating between different nucleotides are present in the pore, the overall current passing through the pore at any one time will be influenced by the interaction between each site and the nucleotide located each site. The presence of multiple sites that are capable of discriminating between different nucleotides increases the number of current levels seen and therefore provides more sequence information. For instance, a pore having a single site may produce four current levels for four different nucleotides (named A, B, C and D for illustrative purposes). In contrast, a pore having two sites may produce sixteen levels: four current levels when A is at site 1 and A, B, C or D is at site 2; four different current levels when B is at site 1 and A, B, C or D is at site 2; four different current levels when C is at site 1 and A, B, C or D is at site 2; and four different current levels when D is at site 1 and A, B, C or D is at site 2.

The dwell time of a selected nucleotide at a site that is capable of discriminating between different nucleotides will be determined by the way in which the target sequence is passed through the pore. For instance, if a nucleic acid handling enzyme is used, the dwell time of a selected nucleotide at a site that is capable of discriminating between different nucleotides will be determined by the rate at which the enzyme pushes or pulls the target sequence through the pore.

Control experiments may be carried out to determine the effect a particular nucleic acid sequence has on the current flowing through the pore. Results from carrying out the method of the invention on a test sample can then be compared with those derived from such a control experiment in order to identify the target sequence.

Site(s) Capable of Discriminating Between Different Nucleotides

A site in the pore is capable of discriminating between different nucleotides if it can discriminate between at least two, such as 3 or 4, different nucleotides. The nucleotides may be any of those discussed above. Each site in the pore is preferably capable of discriminating between four different nucleotides. Each site is most preferably capable of discriminating between the four nucleotides of DNA or RNA. In particular, each site is preferably capable of discriminating between four different nucleotides independently comprising the nucleobases (a) adenine, (b) guanine, (c) thymine or uracil and (d) cytosine. Each site is more preferably capable of discriminating between five different nucleotides independently comprising the nucleobases (a) adenine, (b) guanine, (c) thymine or uracil, (d) cytosine and (e) 5-methylcytosine.

A site is typically capable of discriminating between different nucleotides because it interacts with, preferably reversibly binds to, a nucleotide and the nucleotide affects the current flowing through the pore in a manner specific for that nucleotide. The way in which a site interacts with a selected nucleotide will depend on a variety of factors including the size of the site, the conformation of the site, the charge of the site, the ability of the site to form hydrogen bonds and the ability of the site to form other intermolecular interactions, such as dipole interactions. A site may have a net charge. The net charge may be negative, but is typically positive. A site may have no net charge. As discussed below, the ability of a site to discriminate between different nucleotides can be altered by altering the size of the site, the conformation of the site and/or the charge of the site.

Each site is preferably present in the barrel or channel of the pore. This allows the interaction between a site and a nucleotide to affect the current flowing through the pore. Site(s) in transmembrane protein pores that are capable of discriminating between different nucleotides are discussed in more detail below.

The pore comprises at least one, such as 2, 3 or 4, sites that are capable of discriminating between different nucleotides. The pore preferably comprises two or more, such as 2, 3 or 4 or more, distinct sites that are capable of discriminating between different nucleotides. Hence, a proportion of the nucleotides in the target sequence preferably interacts one at a time with two or more distinct sites in the pore that are capable of discriminating between different nucleotides. The pore most preferably comprises two distinct sites that are capable of discriminating between different nucleotides. Hence, a proportion of the nucleotides in the target sequence most preferably interacts with two distinct sites in the pore that are capable of discriminating between different nucleotides. Each nucleotide in the target sequence preferably interacts with each specific site, one site at a time.

Sites are distinct if they are separated from one another by sufficient distance to allow the interaction of a selected nucleotide with each site to be distinguished as described herein. Distinct sites are typically separated from one another by at least 10, at least 20, at least 30, at least 40 or at least 50 Angstroms. Distinct sites are preferably separated by from each other by about 20 to about 30 Angstroms.

Preferably, the two or more distinct sites each discriminate between different nucleotides in a different manner. This makes it possible to determine when a selected nucleotide is interacting with each of the two or more sites. The two or more sites may differ in the way in which they discriminate between different nucleotides in any manner. Some sites may discriminate between different nucleotides on the basis of different steric interactions with each of the nucleotides. Such interactions are typically dependent on the size and/or conformation of the sites. Other sites with a net charge may discriminate between different nucleotides on the basis of different ionic interactions with each of the nucleotides.

Figure 4:
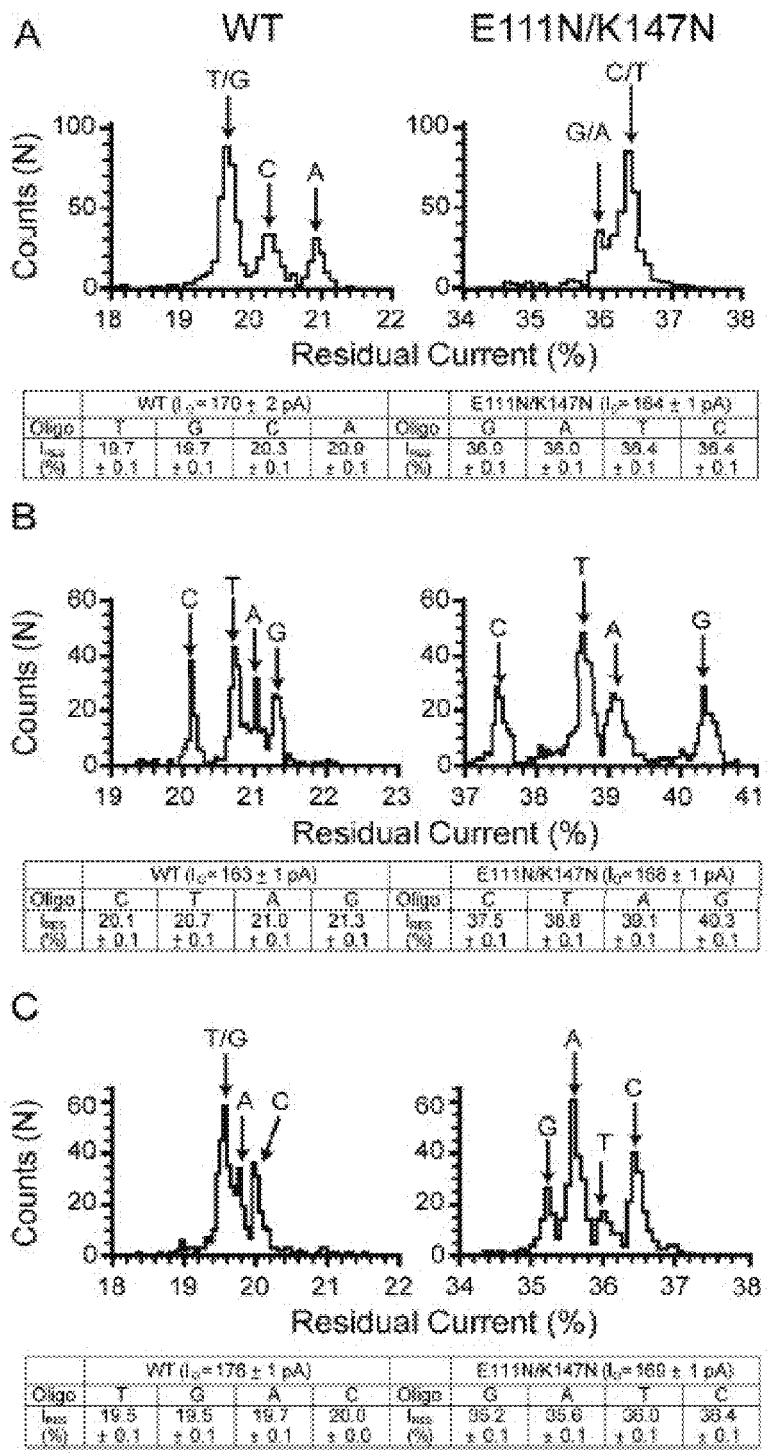
FIG. 4 shows recognition of all four DNA bases by the WT and E111N/K147N α-HL pores. Histograms of the residual current levels for WT (left) and E111N/K147N (right) pores are shown. Three sets of four poly(dC) oligonucleotides were used, with each set containing either a single G, A, T, or C nucleotide at a specific position. All experiments were conducted at least three times, and the results displayed in the figure are from a typical experiment. (A) The WT and E111N/K147N pores were interrogated with SEQ ID NOs: 35 to 38. Gaussian fits were performed for each peak, and the mean value of the residual current for each oligonucleotide (and the standard deviation) is displayed in the table below the histograms. (B) WT and E111N/K147N pores were interrogated with SEQ ID NOs: 39 to 42. (C) WT and E111N/K147N pores were interrogated with SEQ ID NOs: 43 to 46.

Typically, each of the two or more sites differs in the way in which its interactions with the different nucleotides affect the current passing through the pore. Preferably, the interaction of a selected nucleotide with each of the two or more distinct sites results in a different current passing through the pore. For instance, the interaction of an adenine-containing nucleotide with each of the two or more distinct sites results in a different current passing through the pore. More preferably, the interaction of different nucleotides with each of the two or more distinct sites results in differing currents passing through the pore and the separation between the mean value of the differing currents differs between each of the two or more distinct sites. This is illustrated in FIG. 4.

The presence in the pore of two or more distinct sites that are capable of discriminating between different nucleotides in different ways offers a couple advantages. First, it allows the number of nucleotides in the target sequence to be counted. If the distance between the two or more sites and the rate at which the target sequence passes through the pore is known, it is possible to count the number of nucleotides that pass through the pore as a selected nucleotide moves from one site to another. This is particularly helpful for determining the length of a continuous stretch of a particular nucleotide within the target sequence. Using a pore with only a single site that is capable of discriminating between different nucleotides, a continuous stretch of five identical nucleotides will not result in any change in the current level as they each of the five nucleotides sequentially interacts with the site. It would be necessary to try to predict, based on the rate at which the target sequence is passed through the pore, how many nucleotides interact with the site. However, if the pore has two sites that are capable of discriminating between different nucleotides, downstream nucleotides sequentially interacting with the second site will alter the current level passing through the pore as each of the five identical nucleotides in the continuous stretch sequentially interacts with the first site. This permits the number of identical nucleotides sequentially interacting with the first site to be counted.

Second and more importantly, the presence in the pore of two or more distinct sites that are capable of discriminating between different nucleotides allows the sequence of the target nucleic acid to be determined more efficiently. Having two distinct sites that discriminate between different nucleotides in different ways ensures that, when the target sequence is sequenced, each nucleotide is not merely observed once, but is in fact interrogated twice. This gives greater certainty that each position in the target sequence has been observed and that the aggregate call for both nucleotides at each position is of a greater quality score than would be possible with a single observation. In other words, the key advantage of the preferred method of the invention is that it allows each nucleotide position of a target sequence to be effectively interrogated twice without having to repeat the method. This ensures that the quality of the sequence generated is consequently very much higher, with a reduced potential for misidentified nucleotide calls, or completely missed nucleotides.

Modification of the Site(s)

The method preferably involves the use of a pore which has been modified to alter the ability of at least one site, such as 2 or 3 sites, to discriminate between different nucleotides. The pore may be modified to introduce one or more, such as 2, distinct sites that are capable of discriminating between different nucleotides. This increases the number of distinct sites that are capable of discriminating between different nucleotides in the pore. The pore may be modified to abolish one or more, such as 2, distinct sites that are capable of discriminating between different nucleotides. This decreases the number of distinct sites that are capable of discriminating between different nucleotides in the pore. However, at least one site, such as 2 or 3 sites, that is capable of discriminating between different nucleotides must remain for the pore to be useful.

The pore may be modified to enhance or reduce the ability of one or more distinct sites to discriminate between different nucleotides. For instance, the ability of one site to discriminate different nucleotides may be increased, while the ability of another distinct site to discriminate different nucleotides may be reduced. This allows the pore to be 'fine tuned' for sequencing specific target nucleic acid sequences.

The pore may be modified in any way to alter the ability of at least one site to discriminate between different nucleotides. One or more, such as 2, 3, 4 or 5 or more, modifications may be made. The one or more modifications preferably alter the current flowing through the pore when a selected nucleotide interacts with the at least one site.

The modification(s) may alter the size and/or conformation of the at least one site and thereby alter its steric interaction with different nucleotides. The modification(s) may alter the net charge of the at least one site and thereby alters its ionic interaction with different nucleotides. The net charge of the at least one site may be altered by (1) introducing positive charge or negative charge, (2) removing positive or negative charge without replacing it, (3) substituting neutral charge or negative charge with positive charge and/or (4) substituting neutral charge or positive charge with negative charge. The modification(s) cannot alter the net charge in such a manner that it interferes with translocation of the target sequence through the pore. For instance, introducing too much positive charge into the barrel or channel of the pore may reduce the current flowing through the pore and thereby prevent discrimination of different nucleotides. Alternatively, introducing too much negative charge into the barrel or channel of the pore may prevent entry of the target sequence into the pore.

The inventors have surprisingly shown that, if a pore contains two or more distinct sites that are capable of discriminating between different nucleotides, modification of one distinct site may alter the ability of the other distinct site(s) to discriminate between different nucleotides. Hence, in a preferred embodiment, the pore is modified at one of the two or more distinct sites and this alters the ability of at least one of the other two or more distinct sites to discriminate between different nucleotides. In another preferred embodiment, the pore is modified at one of the two or more distinct sites and this alters the ability of all of the other distinct sites to discriminate between different nucleotides. In another preferred embodiment, the pore is modified at one of the two or more distinct sites and this alters the ability of all of the other distinct sites to discriminate between different nucleotides. Any of the modifications described above may be used. Most preferably, the pore is modified at one of the two or more distinct sites to increase the difference between the currents passing through the pore when a selected nucleotide interacts with each of the two or more distinct sites.

It will be necessary to balance the effects of modifications at each of the two or more distinct sites. For instance, altering the net charge at one site may reduce the current flowing through the pore when the site interacts with nucleotides and thereby make it less easy to discriminate between different nucleotides at the other more distal site(s). Alternatively, modifying one site to increase the current flowing the pore may improve discrimination between different nucleotides at the other more distal site(s). This is discussed in more detail below with reference to transmembrane protein pores.

Pores

The method involves passing the target sequence through a transmembrane pore. A transmembrane pore is a pore that permits ions driven by an applied potential to flow from one side of a membrane to the other side of the membrane. The pore allows a nucleic acid, such as DNA or RNA, to be passed through the pore.

The pore is preferably a transmembrane protein pore. A transmembrane protein pore is a polypeptide or a collection of polypeptides that permits ions driven by an applied potential to flow from one side of a membrane to the other side of the membrane.

The pore may be isolated, substantially isolated, purified or substantially purified. A pore is isolated or purified if it is completely free of any other components, such as lipids or other pores. A pore is substantially isolated if it is mixed with carriers or diluents which will not interfere with its intended use. For instance, a pore is substantially isolated or substantially purified if it present in a form that comprises less than 10%, less than 5%, less than 2% or less than 1% of other components, such as lipids or other pores. The pore is typically present in a lipid bilayer.

The pore may be a monomer or an oligomer. The pore is preferably made up of several repeating subunits, such as 6, 7 or 8 subunits. The pore is more preferably a heptameric pore. The pore typically comprises a barrel or channel through which the ions may flow. The subunits of the pore typically surround a central axis and contribute strands to a transmembrane β barrel or channel or a transmembrane α-helix bundle or channel.

The pore comprises at least one site that is capable of discriminating between different nucleotides. The site(s) are preferably in the barrel or channel of the pore. Each site typically comprises several, such as 10, 20 or 30, amino acids that facilitate interaction with nucleotides. If the pore is an oligomer, each monomer may contribute one or more, such as 2, 3, or 4, amino acids to each site. These amino acids are preferably located near a constriction of the barrel or channel. Each site typically comprises one or more positively charged amino acids, such as arginine, lysine or histidine. These amino acids typically facilitate the interaction between the site and the nucleotides. Pores for use in accordance with the invention can be β-barrel pores, α-helix bundle pores or solid state pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin A (MspA), outer membrane porin F (OmpF), outer membrane porin G (OmpG), outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and α outer membrane proteins, such as Wza.

The pore may be a solid state pore. Suitable solid state pores include, but are not limited to, silicon nitride pores, silicon dioxide pores and graphene pores. Other suitable solid state pores and methods of producing them are discussed in U.S. Pat. No. 6,464,842, WO 03/003446, WO 2005/061373, U.S. Pat. No. 7,258,838, U.S. Pat. No. 7,466,069, U.S. Pat. No. 7,468,271 and U.S. Pat. No. 7,253,434.

The pore is preferably derived from α-hemolysin (α-HL). The wild type α-HL pore is formed of seven identical monomers or subunits (i.e. it is heptameric). The sequence of one wild type monomer or subunit of α-hemolysin is shown in SEQ ID NO: 2. The pore preferably comprises seven subunits comprising the sequence shown in SEQ ID NO: 2 or a variant thereof. The pore may be a homoheptamer comprising seven identical subunits of SEQ ID NO: 2 or a variant thereof. Alternatively, the pore may be a heteroheptamer comprising two or more, such as 2, 3, 4, 5, 6 or 7, different subunits. Each subunit in the heteroheptamer may comprise SEQ ID NO: 2 or a variant thereof.

Amino acids 1, 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274, 287 to 290 and 294 of SEQ ID NO: 2 form loop regions. Residues 111, 113 and 147 of SEQ ID NO: 2 form part of a constriction of the barrel or channel of α-HL.

A variant of SEQ ID NO: 2 is a subunit that has an amino acid sequence which varies from that of SEQ ID NO: 2 and which retains its pore forming ability. The ability of a variant to form a pore can be assayed using any method known in the art. For instance, the variant may be inserted into a membrane along with other appropriate subunits and its ability to oligomerise to form a pore may be determined. Methods are known in the art for inserting subunits into membranes, such as lipid bilayers. For example, subunits may be suspended in a purified form in a solution containing a lipid bilayer such that it diffuses to the lipid bilayer and is inserted by binding to the lipid bilayer and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

As described in the Example, pores formed from SEQ ID NO: 2 or a variant thereof have three sites that are capable of discriminating different nucleotides (named $R_1$, $R_2$ and $R_3$). $R_1$ is near the central constriction at position 147 of SEQ ID NO: 2. $R_1$ has a net charge. $R_2$ is about 20 to about 30 angstroms further down the n-barrel from $R_1$. $R_2$ is near position 139 of SEQ ID NO: 2. $R_3$ is about 20 to about 30 angstroms further down the β-barrel from $R_2$. Hence, $R_3$ is about 40 to about 60 angstroms down the n-barrel from $R_1$. $R_2$ has no net charge. $R_3$ is near the trans exit of the barrel or channel at position(s) 127, 128, 129 and 131 of SEQ ID NO: 2. $R_3$ has a net charge. Variants of SEQ ID NO: 2 may comprise modifications that affect these sites as described above and below.

The variant may include one or more modifications that alter the ability of at least one of $R_1$, $R_2$ and $R_3$ to discriminate between different nucleotides. In other words, the variant may be modified to alter the ability of (1) $R_1$, (2) $R_2$, (3) $R_3$, (4) $R_1$ and $R_2$, (5) $R_2$ and $R_3$ (6) $R_1$ and $R_3$, or (7) $R_1$, $R_2$ and $R_3$ to discriminate between different nucleotides. The variant may be modified in any way. The modification(s) may enhance or reduce the ability of at least one of $R_1$, $R_2$ and $R_3$ to discriminate between different nucleotides. The modification(s) can abolish the ability of at least one of $R_1$, $R_2$ and $R_3$ to discriminate between different nucleotides. The modification(s) preferably increase the difference between the currents passing through the pore when a selected nucleotide interacts with at least one of $R_1$, $R_2$ and $R_3$ compared with the others.

It will be necessary to balance the effects of particular modifications at each of $R_1$, $R_2$ and $R_3$. For instance, altering the net charge of $R_1$ may reduce the current flowing through the pore when it interacts with and thereby make it less easy to discriminate between different nucleotides at $R_2$ and/or $R_3$. Alternatively, modifying $R_1$ to increase the current flowing the pore when it interacts with nucleotides may improve discrimination between different nucleotides at $R_2$ and/or $R_3$.

The modifications may alter the size and/or conformation of at least one of $R_1$, $R_2$ and $R_3$ and thereby alter their steric interactions with different nucleotides. Discrimination between different nucleotides by at least one of $R_1$, $R_2$ and $R_3$ is preferably enhanced by introducing one or more amino acids having large side chains, such as tyrosine, arginine or tryptophan. The one or more amino acids may be introduced by addition. The one or more amino acids are preferably introduced by substitution. Discrimination between different nucleotides by at least one of $R_1$, $R_2$ and $R_3$ is preferably enhanced by substituting one or more amino acids in at least one of $R_1$, $R_2$ and $R_3$ with one or more amino acids having larger side chains.

Discrimination between different nucleotides by at least one of $R_1$, $R_2$ and $R_3$ is preferably reduced by introducing one or more amino acids having small side chains, such as glycine, alanine or serine. The one or more amino acids may be introduced by addition. The one or more amino acids are preferably introduced by substitution. Discrimination between different nucleotides by at least one of $R_1$, $R_2$ and $R_3$ is preferably reduced by substituting one or more amino acids in at least one of $R_1$, $R_2$ and $R_3$ with one or more amino acids having larger side chains.

The relative size of the side chains of amino acids can be determined by comparing their van der Waal volumes. The relative van der Waal volumes of the side chains of the standard amino acids is as follows (smallest first): glycine (G)<alanine (A)<serine (S)<cysteine (C)<proline (P)<aspartic acid (D)<threonine (T)<asparagine (N)<valine (V)<glutamic acid (E)<glutamine (Q)<histidine (H)<isoleucine (I)=leucine (L)=methionine (M)<phenylalanine (F)=lysine (K)<tyrosine (Y)<arginine (R)<tryptophan (W). Hence, substituting glycine with arginine constitutes substitution with an amino acid having a large side chain.

The modification(s) may alter the net charge of at least one of $R_1$, $R_2$ and $R_3$ and thereby alter their ionic interactions with different nucleotides. The modification(s) preferably increase the net positive charge of at least one of $R_1$, $R_2$ and $R_3$ and thereby alter their interaction with different nucleotides. The modification(s) do not have to alter the net charge of at least one of $R_1$, $R_2$ and $R_3$ as long as the ability of at least one of $R_1$, $R_2$ and $R_3$ to discriminate between different nucleotides is altered.

The net positive charge of at least one of $R_1$, $R_2$ and $R_3$ is preferably increased by introducing one or more positively charged amino acids. The one or more positively charged amino acids may be introduced by addition. The one or more positively charged amino acids are preferably introduced by substitution.

A positively charged amino acid is an amino acid with a net positive charge. The positively charged amino acid(s) can be naturally-occurring or non-naturally-occurring. The positively charged amino acids may be synthetic or modified. For instance, modified amino acids with a net positive charge may be specifically designed for use in the invention. A number of different types of modification to amino acids are well known in the art.

Preferred naturally-occurring positively charged amino acids include, but are not limited to, histidine (H), lysine (K) and arginine (R). Any number and combination of H, K and/or R may be introduced.

Methods for adding or substituting naturally-occurring amino acids are well known in the art. For instance, methionine (M) may be substituted with arginine (R) by replacing the codon for methionine (ATG) with a codon for arginine (AGA) at the relevant position in a polynucleotide encoding the pore. The polynucleotide can then be expressed as discussed above.

Methods for adding or substituting non-naturally-occurring amino acids are also well known in the art. For instance, non-naturally-occurring amino acids may be introduced by including synthetic aminoacyl-tRNAs in the IVTT system used to express the pore. Alternatively, they may be introduced by expressing the pore in E. coli that are auxotrophic for specific amino acids in the presence of synthetic (i.e. non-naturally-occurring) analogues of those specific amino acids. They may also be produced by native ligation if the pore is produced using partial peptide synthesis.

Any amino acid may be substituted with a positively charged amino acid. One or more uncharged amino acids, non-polar amino acids and/or aromatic amino acids may be substituted with one or more positively charged amino acids. Uncharged amino acids have no net charge. Suitable uncharged amino acids include, but are not limited to, cysteine (C), serine (S), threonine (T), methionine (M), asparagine (N) and glutamine (Q). Non-polar amino acids have non-polar side chains. Suitable non-polar amino acids include, but are not limited to, glycine (G), alanine (A), proline (P), isoleucine (I), leucine (L) and valine (V). Aromatic amino acids have an aromatic side chain. Suitable aromatic amino acids include, but are not limited to, histidine (H), phenylalanine (F), tryptophan (W) and tyrosine (Y). Preferably, one or more negatively charged amino acids are substituted with one or more positively charged amino acids. Suitable negatively charged amino acids include, but are not limited to, aspartic acid (D) and glutamic acid (E).

Preferred introductions include, but are not limited to, substitution of M with R, substitution of M with H, substitution of M with K, substitution of D with R, substitution of D with H, substitution of D with K, substitution of E with R, substitution of E with H and substitution of E with K.

Any number of positively charged amino acids may be introduced. For instance, 1, 2, 5, 10, 15, 20, 25 or more positively charged amino acids may be introduced. In the case of α-HL (i.e. SEQ ID NO: 2 and 4 and variants thereof discussed above), the one or more positively charged amino acids may be introduced into 1, 2, 3, 4, 5, 6 or 7 of the subunits in the pore. In each of the seven subunits, the one or more positively charged amino acids may be introduced at the same or different positions. Preferably, the pore is a homoheptamer and one or more positive amino acids are introduced at the same position(s) in each subunit.

The net positive charge of at least one of $R_1$, $R_2$ and $R_3$ may also be increased by replacing by substitution one or more negatively charged amino acids with one or more uncharged amino acids, non-polar amino acids and/or aromatic amino acids. The removal of negative charge increases the net positive charge. The uncharged amino acids, non-polar amino acids and/or aromatic amino acids can be naturally-occurring or non-naturally-occurring. They may be synthetic or modified. Suitable uncharged amino acids, non-polar amino acids and aromatic amino acids are discussed above. Preferred substitutions include, but are not limited to, substitution of E with N, substitution of D with N, substitution of E with T, substitution of D with T, substitution of E with G and substitution of D with G.

Any number and combination of uncharged amino acids, non-polar amino acids and/or aromatic amino acids may substituted into at least one of $R_1$, $R_2$ and $R_3$. For instance, 1, 2, 5, 10, 15, 20, 25 or more uncharged amino acids, non-polar amino acids and/or aromatic amino acids may be may substituted. In the case of α-HL (i.e. SEQ ID NO: 2 and 4 and variants thereof discussed above), the uncharged amino acids, non-polar amino acids and/or aromatic amino acids may be substituted into 1, 2, 3, 4, 5, 6 or 7 of the subunits in the pore. In each of the seven subunits, the one or more uncharged amino acids, non-polar amino acids and/or aromatic amino acids may be substituted into the same or different positions. Preferably, the pore is a homoheptamer and uncharged amino acids, non-polar amino acids and/or aromatic amino acids are substituted into the same position(s) in each subunit. Negatively charged amino acids may be substituted with (1) uncharged amino acids; (2) non-polar amino acids; (3) aromatic amino acids; (4) uncharged amino acids and non-polar amino acids; (5) uncharged amino acids and aromatic amino acids; and (5) non-polar amino acids and aromatic amino acids; or (6) uncharged amino acids, non-polar amino acids and aromatic amino acids.

The net negative charge of at least one of $R_1$, $R_2$ and $R_3$ is preferably increased by introducing one or more negatively charged amino acids into the barrel or channel and/or entrance of the pore. The one or more negatively charged amino acids may be introduced by addition. The one or more negatively charged amino acids are preferably introduced by substitution. Methods for adding and substituting amino acids are well known in the art.

Suitable negatively charged amino acids are discussed above. The negatively charged amino acid(s) can be naturally-occurring or non-naturally-occurring. The negatively charged amino acids may be synthetic or modified.

Any amino acid may be substituted with a negatively charged amino acid. One or more uncharged amino acids, non-polar amino acids and/or aromatic amino acids may be substituted with one or more negatively charged amino acids. Preferably, one or more positively charged amino acids are substituted with one or more negatively charged amino acids. Any number of negatively charged amino acids may be introduced as discussed above.

The net negative charge may also be increased by replacing by substitution one or more positively charged amino acids with one or more uncharged amino acids, non-polar amino acids and/or aromatic amino acids. The removal of positive charge increases the net negative charge. The uncharged amino acids, non-polar amino acids and/or aromatic amino acids can be naturally-occurring or non-naturally-occurring. They may be synthetic or modified.

Any number and combination of uncharged amino acids, non-polar amino acids and/or aromatic amino acids may substituted into the barrel or channel and/or entrance as discussed above.

The modification(s) do not have to alter the net charge of at least one of $R_1$, $R_2$ and $R_3$. For instance, at least one of $R_1$, $R_2$ and $R_3$ may be modified by replacing a positively charged amino acid with an uncharged amino acid and a negatively charged amino acid with an uncharged amino acid.

The modifications to $R_1$, $R_2$ and/or $R_3$ described above are preferably made to amino acids that face inward into the barrel or channel of the pore. Such amino acids can be identified as described in Song, L., Hobaugh, M. R., Shustak C., Cheley, S., Bayley, H., and Gouaux, J. E. (1996) *Science* 274, 1859-1866.

In a preferred embodiment, the variant of SEQ ID NO: 2 is modified at one of $R_1$, $R_2$ and $R_3$ and this alters the ability of one of the other sites to discriminate between different nucleotides. In another preferred embodiment, the variant is modified at one of $R_1$, $R_2$ and $R_3$ and this alters the ability of all of $R_1$, $R_2$ and $R_3$ to discriminate between different nucleotides. In a most preferred embodiment, the variant is modified at $R_1$ and this alters the ability of all of $R_1$, $R_2$ and $R_3$ to discriminate between different nucleotides. The variant preferably comprises an asparagine at position 111 of SEQ ID NO: 2 and an asparagine at position 147 of SEQ ID NO: 2. SEQ ID NO: 4 shows the sequence of SEQ ID NO: 2 except that it has an asparagine at position 111 of SEQ ID NO: 2 (E111N) and an asparagine at position 147 of SEQ ID NO: 2 (K147N). SEQ ID NO: 4 or a variant thereof may be used to form a pore in accordance with the invention. The variant of SEQ ID NO: 4 may differ from SEQ ID NO: 4 in the same way and to the same extent as discussed for SEQ ID NO: 2 above except that it must have an asparagine at position 111 of SEQ ID NO: 4 and an asparagine at position 147 of SEQ ID NO: 4. A preferred pore for use in the invention comprises one or more, preferably seven, subunits comprising SEQ ID NO: 4.

The variant may also include other modifications that facilitate an interaction with nucleotides. In particular, the variant preferably has a glutamine at position 139 of SEQ ID NO: 2. The variant preferably has an arginine or a tyrosine at position 113 of SEQ ID NO: 2.

The variant may include modifications that facilitate covalent attachment to or interaction with a nucleic acid handling protein. The variant preferably comprises one or more reactive cysteine residues that facilitate attachment to the nucleic acid handling enzyme. For instance, the variant may include a cysteine at one or more of positions 8, 9, 17, 18, 19, 44, 45, 50, 51, 237, 239 and 287 and/or on the amino or carboxy terminus of SEQ ID NO: 2. Preferred variants comprise a substitution of the residue at position 8, 9, 17, 237, 239 and 287 of SEQ ID NO: 2 with cysteine (K8C, T9C, N17C, K237C, S239C or E287C).

The variant may be a naturally occurring variant which is expressed naturally by an organism, for instance by a *Staphylococcus* bacterium, or expressed recombinantly by a bacterium such as *Escherichia coli*. Variants also include non-naturally occurring variants produced by recombinant technology. Over the entire length of the amino acid sequence of SEQ ID NO: 2 or 4, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 or 4 over the entire sequence. There may be at least 80%, for example at least 85%, 90% or 95%, amino acid identity over a stretch of 200 or more, for example 230, 250, 270 or 280 or more, contiguous amino acids ("hard homology"). Homology can be measured as described above.

Amino acid substitutions may be made to the amino acid sequence of SEQ ID NO: 2 or 4 in addition to those discussed above, for example up to 1, 2, 3, 4, 5, 10, 20 or 30 substitutions. Conservative substitutions may be made, for example, according to Table 1 above.

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may include fragments of SEQ ID NO: 2 or 4. Such fragments retain pore forming activity. Fragments may be at least 50, 100, 200 or 250 amino acids in length. A fragment preferably comprises the pore forming domain of SEQ ID NO: 2 or 4. Fragments typically include residues 119, 121, 135. 113 and 139 of SEQ ID NO: 2 or 4.

One or more amino acids may be alternatively or additionally added to the polypeptides described above. An extension may be provided at the amino terminus or carboxy terminus of the amino acid sequence of SEQ ID NO: 2 or 4 or a variant or fragment thereof. The extension may be quite short, for example from 1 to 10 amino acids in length. Alternatively, the extension may be longer, for example up to 50 or 100 amino acids. A carrier protein may be fused to a pore or variant.

As discussed above, a variant of SEQ ID NO: 2 or 4 is a subunit that has an amino acid sequence which varies from that of SEQ ID NO: 2 or 4 and which retains its ability to form a pore. A variant typically contains the regions of SEQ ID NO: 2 or 4 that are responsible for pore formation. The pore forming ability of α-HL, which contains a β-barrel, is provided by β-strands in each subunit. A variant of SEQ ID NO: 2 or 4 typically comprises the regions in SEQ ID NO: 2 that form β-strands. The amino acids of SEQ ID NO: 2 or 4 that form β-strands are discussed above. One or more modifications can be made to the regions of SEQ ID NO: 2 or 4 that form β-strands as long as the resulting variant retains its ability to form a pore. Specific modifications that can be made to the β-strandregions of SEQ ID NO: 2 or 4 are discussed above.

A variant of SEQ ID NO: 2 or 4 preferably includes one or more modifications, such as substitutions, additions or deletions, within its α-helices and/or loop regions. Amino acids that form α-helices and loops are discussed above.

The variant may be modified for example by the addition of histidine or aspartic acid residues to assist its identification or purification or by the addition of a signal sequence to promote their secretion from a cell where the polypeptide does not naturally contain such a sequence.

Variants may also comprise any of the non-specific modifications discussed above for the nucleic acid handling enzyme. Subunits or pores can be made as discussed above.

Any of the specific modifications discussed above with reference to SEQ ID NO: 2 are equally applicable to other transmembrane protein pores disclosed herein.

Transmembrane protein pores can be produced as described above for nucleic acid handling enzymes.

Attachment

If a nucleic acid handling enzyme is used, the enzyme should handle the target nucleic acid sequence in a specific manner. For instance, the target sequence must be passed through the pore in a processive manner as described above. This ensures that a proportion of the nucleotides in the target nucleic acid sequence interacts with the pore and is identified. The lack of any interruption in the signal is important when sequencing nucleic acids. The best way to ensure the specific handling of the target sequence by the enzyme is to attach the enzyme to the pore. In addition, if the enzyme is fixed to the pore, they can be stored together, thereby allowing the production of a ready-to-use sensor.

In a preferred embodiment, a nucleic acid handling enzyme is attached to the pore. This allows the target nucleic acid sequence is pushed through the barrel or channel of the pore in a stepwise manner and a proportion of the nucleotides in the target sequence to interacts with site(s) capable of discriminating different nucleotides. Suitable enzymes are discussed above. The enzyme is preferably attached to the pore at a site in close proximity to the opening of the barrel of channel of the pore. The enzyme is more preferably attached to the pore such that its active site is orientated towards the opening of the barrel of channel of the pore. This means that the target nucleic acid sequence is fed into the barrel or channel. The enzyme is preferably attached to the cis side of the pore.

The nucleic acid handling enzyme can be attached to the pore using any method known in the art. The nucleic acid handling enzyme and pore may be produced separately and then attached together. If the pore is a protein, the two components may be attached in any configuration. For instance, they may be attached via their terminal (i.e. amino or carboxy terminal) amino acids. Suitable configurations include, but are not limited to, the amino terminus of the nucleic acid handling enzyme being attached to the carboxy terminus of the pore and vice versa. Alternatively, the two components may be attached via amino acids within their sequences. For instance, the nucleic acid handling enzyme may be attached to one or more amino acids in a loop region of the pore. In a preferred embodiment, terminal amino acids of the nucleic acid handling enzyme are attached to one or more amino acids in the loop region of the pore. Terminal amino acids and loop regions are discussed above.

The nucleic acid handling enzyme is preferably chemically fused to the pore. A nucleic acid handling enzyme is chemically fused to a pore if the two parts are chemically attached, for instance via a linker molecule. Any method of chemical fusion or attachment can be used. Suitable methods include, but are not limited to, histidine tag binding to a metal affinity matrix, Ni-NTA, biotin binding to streptavidin, antibody binding to an antigen, primary amine coupling, GST tags binding to glutathione, MBP tags binding to dextrin, Protein A binding to IgG, reaction between thiols, nucleic acid hybridization linkers and cysteine linkage. DNA hybridization linkers and cysteine linkage are discussed in more detail below. The nucleic acid handling enzyme is preferably covalently attached to the pore.

If the pore is a protein, the nucleic acid handling enzyme may be genetically fused to the pore. A nucleic acid handling enzyme is genetically fused to a protein pore if the whole construct is expressed from a single polynucleotide sequence. The coding sequences of the nucleic acid handling enzyme and pore may be combined in any way to form a single polynucleotide sequence encoding the construct.

The nucleic acid handling enzyme and pore may be genetically fused in any configuration, such as via their terminal amino acids. The amino acid sequence of the nucleic acid handling enzyme is typically added in frame into the amino acid sequence of the pore. In a preferred embodiment, the nucleic acid handling enzyme is inserted into a loop region of a transmembrane protein pore. In an especially preferred embodiment, the nucleic acid handling enzyme is inserted between amino acids, 18 and 19, 44 and 45 or 50 and 51 of SEQ ID NO: 2.

The nucleic acid handling enzyme retains its ability to bind nucleic acids. This ability is typically provided by its secondary structural elements (α-helices and β-strands) and tertiary structural elements. In order to avoid adversely affecting the nucleic acid binding ability of the protein, it is preferably attached to the pore in a manner that does not affect its secondary or tertiary structure.

The pore retains its ability to permit ions driven by an applied potential to flow from one side of a membrane to the other side of the membrane. The pore forming ability of pores is typically provided by their α-helices and β-strands. β-barrel pores comprise a barrel or channel that is formed from β-strands, whereas α-helix bundle pores comprise a barrel or channel that is formed from α-helices. The α-helices and β-strands are typically connected by loop regions. In order to avoid affecting the functioning of the pore, the nucleic acid handling enzyme is preferably attached to a loop region of the pore. The loop regions of specific pore subunits are discussed in more detail above.

The nucleic acid handling enzyme is preferably attached to the pore using one or more, such as 2, 3 or 4, linkers. The one or more linkers may be designed to constrain the mobility of the nucleic acid handling enzyme. The linkers are typically attached to the one or more accessible cysteine residues in the nucleic acid handling enzyme. The linkers may be attached to one or more reactive groups, such as cysteine residues, reactive lysine residues or non-natural amino acids, in the pore. Suitable linkers are well known in the art. Suitable linkers include, but are not limited to, chemical crosslinkers and peptide linkers. Preferred chemical crosslinkers are nucleic hybridization linkers. The length, flexibility and hydrophilicity of the nucleic acid hybridization linkers are typically designed such that they do not to disturb the functions of the nucleic acid handling enzyme and pore. The nucleic acid hybridization linkers can comprise any of the nucleic acids discussed above.

Linkers may be attached to the nucleic acid handling enzyme first and then the pore, the pore first and then the nucleic acid handling enzyme or the pore and nucleic acid handling enzyme at the same time. When the linker is attached to a pore subunit (as the pore), it may be a monomeric subunit, part of an oligomer of two or more monomers or part of complete oligomeric pore. It is preferred that the linker is reacted before any purification step to remove any unbound linker.

The preferred method of attaching the nucleic acid handling enzyme to the pore is via cysteine linkage. This can be mediated by a bi-functional chemical linker or by a polypeptide linker with a terminal presented cysteine residue. α-HL (SEQ ID NO: 2) lacks native cysteine residues so the introduction of a cysteine into the sequence of SEQ ID NO: 2 enables the controlled covalent attachment of the nucleic acid handling enzyme to the subunit. Cysteines can be introduced at various positions, such as position K8, T9 or N17 of SEQ ID NO: 2 or at the carboxy terminus of SEQ ID NO: 2. The length, reactivity, specificity, rigidity and solubility of any bi-functional linker may be designed to ensure that the enzyme is positioned correctly in relation to the subunit and the function of both the subunit and enzyme is retained. Suitable linkers include those described above.

Cross-linkage of subunits or enzymes to themselves may be prevented by keeping the concentration of linker in a vast excess of the nucleic acid handling enzyme and/or the pore. Alternatively, a "lock and key" arrangement may be used in which two linkers are used. For instance, click chemistry, such as wide alkyne Huisgen cycloaddition, may be used to ensure that the nucleic acid handling enzyme only binds to the pore and not to itself and vice versa.

The nucleic acid handling enzyme is preferably attached to the part of a pore or a subunit thereof that forms part of the cis side of a pore. In electrophysiology, the cis side is the grounded side by convention. If a hemolysin pore is inserted correctly into an electrophysiology apparatus, the Cap region is on the cis side. It is well known that, under a positive potential, nucleotides will migrate from the cis to the trans side of pores used for stochastic sensing. Positioning the nucleic acid handling enzyme at the cis side of a pore allows it to handle the target nucleic acid such that a proportion of the nucleotides in the sequence enters the barrel or channel of the pore and interacts with it. Preferably, at least 20%, at least 40%, at least 50%, at least 80% or at least 90% of the nucleotides in the sequence enters the barrel or channel of the pore and interacts with it.

The site and method of covalent attachment is preferably selected such that mobility of the nucleic acid handling enzyme is constrained. This helps to ensure that the protein handles the target nucleic acid sequence in such a way that a proportion of the nucleotides in the target sequence interacts with the pore. For instance, constraining the ability of nucleic acid handling enzyme to move means that its active site can be permanently orientated towards the part of the subunit that forms part of the opening of the barrel of channel of the pore. The mobility of the nucleic acid handling enzyme may be constrained by increasing the number of points at which the protein is attached to the pore and/or the use of specific linkers.

Apparatus

The method may be carried out using any apparatus that is suitable for investigating a membrane/pore system in which a pore is inserted into a membrane. The method may be carried out using any apparatus that is suitable for stochastic sensing. For example, the apparatus comprises a chamber comprising an aqueous solution and a barrier that separates the chamber into two sections. The barrier has an aperture in which the membrane containing the pore is formed. The target sequence may be contacted with the pore by introducing the sequence into the chamber. The target sequence may be introduced into either of the two sections of the chamber, but, if a nucleic acid handling enzyme used, is preferably introduced into the section of the chamber containing the enzyme.

The method may be carried out using the apparatus described in International Application No. PCT/GB08/000, 562.

The method involves measuring the current passing through the pore during interaction with the nucleotides. Therefore the apparatus also comprises an electrical circuit capable of applying a potential and measuring an electrical signal across the membrane and pore. The method may be carried out using a patch clamp or a voltage clamp. The method preferably involves the use of a voltage clamp.

Conditions

The method of the invention involves the measuring of a current passing through the pore during interaction with nucleotides of a target nucleic acid sequence. Suitable conditions for measuring ionic currents through transmembrane pores are known in the art and disclosed in the Examples. The method is carried out with a voltage applied across the membrane and pore. The voltage used is typically from −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 120 mV to 170 mV. It is possible to increase discrimination between different nucleotides by at least one site capable of discriminating between different nucleotides by varying the applied potential.

The method is carried out in the presence of any alkali metal chloride salt. In the exemplary apparatus discussed above, the salt is present in the aqueous solution in the chamber. Potassium chloride (KCl), sodium chloride (NaCl) or caesium chloride (CsCl) is typically used. KCl is preferred. The salt concentration is typically from 0.1 to 2.5M, from 0.3 to 1.9M, from 0.5 to 1.8M, from 0.7 to 1.7M, from 0.9 to 1.6M or from 1M to 1.4M. High salt concentrations provide a high signal to noise ratio and allow for currents indicative of the presence of a nucleotide to be identified against the background of normal current fluctuations. However, lower salt concentrations may have to be used so that the enzyme is capable of functioning.

The method is typically carried out in the presence of a buffer. In the exemplary apparatus discussed above, the buffer is present in the aqueous solution in the chamber. Any buffer may be used in the method. One suitable buffer is Tris-HCl buffer. The method is typically carried out at a pH of from 4.0 to 13.0, from 4.5 to 12, from 5.0 to 11, from 5.5 to 10, from 6.0 to 9 or from 7.0 to 8.8 or 7.5 to 8.5. DNA denatures at a pH of around 11. The pH used is preferably about 7.5.

The method is typically carried out at from 0° C. to 100° C., from 15° C. to 95° C., from 16° C. to 90° C., from 17° C. to 85° C., from 18° C. to 80° C., 19° C. to 70° C., or from 20° C. to 60° C. The method may be carried out at room temperature. The method is preferably carried out at a temperature that supports enzyme function, such as about 37° C. Good nucleotide discrimination can be achieved at low salt concentrations if the temperature is increased. However, lower temperatures, particularly those below room temperature, result in longer dwell times and can therefore be used to obtain a higher degree of accuracy.

In addition to increasing the solution temperature, there are a number of other strategies that can be employed to increase the conductance of the solution, while maintaining conditions that are suitable for enzyme activity. One such strategy is to use the lipid bilayer to divide two different concentrations of salt solution, a low salt concentration of salt on the enzyme side and a higher concentration on the opposite side. One example of this approach is to use 200 mM of KCl on the cis side of the membrane and 500 mM KCl in the trans chamber. At these conditions, the conductance through the pore is expected to be roughly equivalent to 400 mM KCl under normal conditions, and the enzyme only experiences 200 mM if placed on the cis side. Another possible benefit of using asymmetric salt conditions is the osmotic gradient induced across the pore. This net flow of water could be used to pull nucleotides into the pore for detection. A similar effect can be achieved using a neutral osmolyte, such as sucrose, glycerol or PEG. Another possibility is to use a solution with relatively low levels of KCl and rely on an additional charge carrying species that is less disruptive to enzyme activity.

Method of Improving Pores

The invention also provides a method for improving a transmembrane pore for sequencing a target nucleic sequence. The target sequence may be homopolymeric or hetropolymeric. A homopolymeric nucleic acid sequence is one made of one type of nucleotide. The nucleotide may be any of those discussed above.

The method is intended to engineer or design an improved transmembrane pore that may be used to sequence nucleic acids as described above. Pores improved in accordance with the invention can be used in a sequencing method of invention.

In one embodiment, the method comprises modifying a pore comprising one site that is capable of discriminating between different nucleotides. The pore may be modified in any of the ways discussed above. The pore is typically modified to introduce at least one more site, such as 2, 3 or 4 sites, that are capable of discriminating between different nucleotides. The method then comprises determining whether or not the resulting pore comprises two or more distinct sites that are capable of discriminating between different nucleotides. The determining step can be done using any method known in the art. For instance, it may be done as described in the Example. The advantages of having two or more sites that are capable of discriminating between different nucleotides are discussed above.

In another embodiment, the method comprises modifying a pore comprising two or more distinct sites that are capable of discriminating between different nucleotides. The pore may be modified in any of the ways discussed above. The pore is typically modified to remove at least one site, such as 2, 3 or 4 sites, that are capable of discriminating between different nucleotides. The method then comprises determining whether or not the resulting pore comprises only two distinct sites that are capable of discriminating between different nucleotides. The determining step can be done using any method known in the art. For instance, it may be done as described in the Example. The advantages of having two sites that are capable of discriminating between different nucleotides are discussed above.

In another embodiment, the method comprises modifying a pore, comprising more than one site, such as 2, 3 or 4 sites, that are capable of discriminating between different nucleotides. The pore may be modified in any of the ways discussed above. The pore is typically modified to remove at least one site, such as 1, 2 or 3 sites, that are capable of discriminating between different nucleotides. The method then comprises determining whether or not the resulting pore comprises only one site that is capable of discriminating between different nucleotides. The determining step can be done using any method known in the art. For instance, it may be done as described in the Example. Pores with only one site that is capable of discriminating between different nucleotides produce a simple current signal when used to sequence target nucleic acid sequences.

In another embodiment, the method comprises modifying a pore comprising two or more sites that are capable of discriminating between different nucleotides at one of the distinct sites. The pore may be modified in any of the ways discussed above. The pore is typically modified to enhance or reduce the ability of at least one, such as 2, 3 or 4, of the distinct sites to discriminate between different nucleotides. The method then comprises determining whether or not the resulting pore the ability of at least one of the distinct sites to discriminate between different nucleotides is altered. The determining step can be done using any method known in the art. For instance, it may be done as described in the Example.

The invention also provides a pore improved using a method of the invention

The following Example illustrates the invention:

EXAMPLE

1 Materials and Methods 1.1 Protein Preparation

α-HL was produced as described in detail elsewhere (Cheley, S., Braha, O., Lu, X., Conlan, S., & Bayley, H. (1999) A functional protein pore with a "Retro" Transmembrane domain. *Protein Sci.* 8, 1257-1267). In brief, the protein was expressed in the presence of [$^{35}$S]methionine in an *E. coli* in vitro transcription and translation (IVTT) system (*E. coli* T7 S30 Extract System for Circular DNA, Cat. #L1130, Promega). IVTT reactions (100 µL) containing α-HL monomers were incubated with rabbit red blood cell membranes for 1 h at 37° C. to form α-HL heptamers. The solution was centrifuged at 25,000×g and the pellet containing heptamers was loaded onto a 5% SDS-polyacrylamide gel, which was run for 4 h at 100 V and subsequently vacuum dried for 3 to 4 h onto Whatman 3M filter paper. The dried gel was exposed to photographic film for 2 h and the developed film was used to locate the position of the heptameric protein in the gel. This region of the gel was excised, rehydrated and crushed in 400 µL of 10 mM Tris.HCl, pH 8.0, containing 100 µM EDTA. After 20 min at room temperature, the polyacrylamide was removed by centrifuging the suspension at 25,000×g for 7 min at room temperature through a cellulose micro spin column (Microfilterfuge tubes, Cat. #7016-024, Rainin). Aliquots of the purified protein were stored at −80° C. The mutant α-HL gene was prepared by using a kit for site-directed mutagenesis (QuickChange II XL, Cat. #200522-5, Stratagene). The DNA sequence of each gene was verified.

1.2 Planar Bilayer Recordings

Electrical recordings were carried out with a planar lipid bilayer apparatus (Montal, M. & Mueller, P. (1972) *Proc. Natl. Acad. Sci. USA* 69, 3561-3566) with a bilayer of 1,2-diphytanoyl-sn-glycero-3-phosphocholine (DPhPC, Avanti Polar Lipids) formed across an aperture (~100 µm in diameter) in a 25-µm thick polytetrafluoroethylene film (Teflon) (Goodfellow Cambridge, Cat. #FP301200/10), which separates the apparatus into cis and trans compartments. Bilayers were formed by first pre-treating the aperture with 10 mg mL$^{-1}$ hexadecane in n-pentane. Electrolyte solution (0.5 mL: 1 M KCl, 25 mM Tris.HCl, 0.1 mM EDTA, pH 8.0) was added to both compartments. Then, DPhPC in n-pentane (10 mg mL$^{-1}$) was added to both compartments. The solvent was allowed to evaporate and the bilayer was formed by lowering and raising the electrolyte level past the aperture.

Lipid bilayers were formed from 1,2-diphytanoyl-sn-glycero-3-phosphocholine (Avanti Polar Lipids). Both compartments of the recording chamber contained 0.5 mL of 1 M KCl, 25 mM Tris.HCl, pH 8.0, with 0.1 mM EDTA. Planar bilayer current recordings were performed with a patch clamp amplifier (Axopatch 200B, Axon Instruments, Foster City, Calif.) with the cis compartment connected to ground. The α-HL pores and the DNA were added to the cis compartment. ssDNA molecules, with a biotinyl group covalently attached to the 3' end through a linker, were obtained from Sigma-Aldrich (UK) (FIG. 7). Solutions of the biotinylated ssDNAs, at 100 µM in 10 mM Tris.HCl, pH 8.0, 0.1 mM EDTA, were mixed with equal volumes of 25 µM streptavidin (SA) (Sigma-Aldrich) in the same buffer. Each oligonucleotide (pre-incubated with streptavidin for at least five minutes) was added to the cis compartment to a final concentration of 200 nM (Example 1) or 400 nM (Example 2). Initially, +160 mV was applied to the trans side for 1800 ms (Example 1) or 900 ms (Example 2) to drive the negatively charged, biotinylated DNA into the pore. The capture of a ssDNA strand by an α-HL pore is observed as a stepwise decrease in the open pore current level ($I_O$) to a lower, but stable, current level ($I_B$). A voltage of −140 mV was then applied for 100 ms (Example 1) or 50 ms (Example 2) to eject the immobilized DNA from the pore. The applied potential was then stepped to 0 mV for 100 ms (Example 1) or 50 ms (Example 2). This two-second or one-second sequence was repeated for at least 100 cycles for each ssDNA species added. The amplified signal (arising from the ionic current passing through the pore) was low-pass filtered at 1 kHz and sampled at 5 kHz with a computer equipped with a Digidata 1440A digitizer (Molecular Devices).

Figure 6:
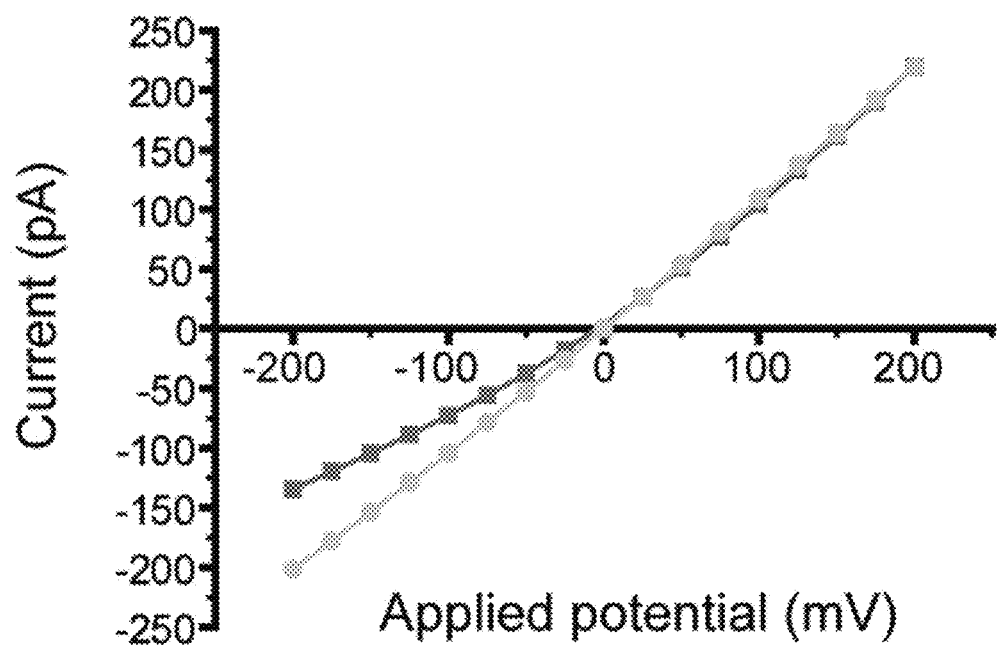
FIG. 6 shows typical current-voltage (IV) traces for WT (squares) and E111N/K147N (circles) α-HL pores, in 1 M KCl, 25 mM Tris.HCl, pH 8.0, containing 0.1 mM EDTA.

Under the conditions of the experiments, all of the pores exhibited a stable open-pore current. The current-voltage characteristics of WT pores are weakly rectifying (Gu, L.-Q., Dalla Serra, M., Vincent, J. B., Vigh, G., Cheley, S., Braha, O., & Bayley, H. (2000) *Proc. Natl. Acad. Sci. USA* 97, 3959-3964). This rectification is lost in E111N/K147N pores (FIG. 6). However, this difference is not relevant to the present work, as both pore types have similar open pore currents at +160 mV, which is the potential at which our experiments were conducted.

1.3 Oligonucleotides

The oligonucleotides used are shown in SEQ ID NOs: 13 to 66. All oligonucleotides have a 3' biotin-TEG tag and linker as shown in FIG. 7.

1.4 Data Analysis

Data were analyzed and prepared for presentation with pClamp software (version 10.1, Molecular Devices). Single-channel searches were performed to obtain the average current level for each ssDNA blockade event ($I_B$). The mean $I_B$ value for each oligonucleotide was determined by performing a Gaussian fit to a histogram of the $I_B$ values. The current blockade for each oligonucleotide was also expressed as the residual current ($I_{RES}$), wherein the average current level for a DNA blockade ($I_B$) is expressed as a percentage of the open pore current ($I_O$): $I_{RES}=(I_B/I_O)\times 100$. In general, when comparing several oligonucleotide species, a single oligonucleotide species was first added to the cis chamber and the current trace required for the determination of $I_B$ and $I_{RES}$ was recorded. Subsequently, a second (and if required, a third and a fourth) oligonucleotide was added and additional currents recorded. For example, the data in FIGS. 4 and 5 come from four oligonucleotide species, with sequences that differ by a single nucleotide. The experiment displayed in FIG. 11, which involves the probing of pores with 16 different sequences, was obtained by adding sets of 4 oligonucleotides at a time rather than adding individual oligonucleotides. Each of the 4 oligonucleotides within a set ($N_9X_{14}$) differed in the base at $R_1$, but had the same base at $R_2$, and each set had a different base at $R_2$. The peaks in the derived histograms were assigned based on previous experiments with the separate sets of 4 oligonucleotides.

When such experiments were repeated, the oligonucleotides were added to the chamber in a different order, and in the case of the 16 oligonucleotide experiment (FIG. 11), the sets of oligonucleotides were added in a different order.

2 Example 1

2.1 Improved Discrimination of Oligonucleotides with a Mutant α-HL Pore ssDNA oligonucleotides (SEQ ID NOs: 13 and 14) with biotin tags at the 3' terminus were allowed to form complexes with streptavidin. In this state, the DNAs were captured and immobilized by α-HL pores in an applied potential, but they were not translocated into the trans compartment (FIG. 1A). The immobilized DNA molecules caused a sequence-dependent decrease in the current flow through the pore (FIG. 1B), and here we quote the residual current ($I_{RES}$) as a percentage of the open pore current ($I_O$). We examined the WT α-HL pore and the pore formed by E111N/K147N. The latter forms stable pores despite the removal of the electrostatic interactions between Glu-111 and Lys-147 residues at the central constriction (Gu, L.-Q., Cheley, S., & Bayley, H. (2001) *J. Gen. Physiol.* 118, 481-494). We hoped that the increased space at the constriction would cause more current to flow in the presence of DNA and hence produce a greater dispersion of $I_{RES}$ values. At +160 mV in 1 M KCl, 25 mM Tris.HCl, pH 8.0, containing 0.1 mM EDTA (the conditions for all the experiments reported in this Example), WT α-HL pores have a mean open pore current level ($I_O^{WT}$) of 171±7 pA (n=20), while pores formed from E111N/K147N gave $I_O^{E111N/K147}$=167±7 pA (n=20). Poly(dA)60 oligonucleotides blocked WT pores to a lesser extent ($I_{RES}^{poly(dA)}$=20.0±1.3%) than poly(dC)60 ($I_{RES}^{poly(dC)}$=19.4±1.4%) (FIG. 1B). The residual current difference between the poly(dA) and the poly(dC) oligonucleotide blockades ($\Delta I_{RES}=I_{RES}^{poly(dA)}-I_{RES}^{poly(dC)}$) was +0.6±0.1%. It should be noted that the $\Delta I_{RES}$ values showed little experimental variation, while the absolute current values showed variation that exceeded $\Delta I_{RES}$ (Table 2).

TABLE 2

Residual currents ($I_{RES}$) for poly(dC) and poly(dA) oligonucleotides immobilized within WT and E111N/K147N pores.

| | WT | | | | | E111N/K147N | | | |
|---|---|---|---|---|---|---|---|---|---|
| Expt | $I_O$ (pA) | $I_{RES}^{pdC}$ (%) | $I_{RES}^{pdA}$ (%) | $\Delta I_{RES}$ (%) | Expt | $I_O$ (pA) | $I_{RES}^{pdC}$ (%) | $I_{RES}^{pdA}$ (%) | $\Delta I_{RES}$ (%) |
| 1 | 163 | 17.1 | 17.8 | 0.7 | 1 | 172 | 37.1 | 34.1 | -3.0 |
| 2 | 172 | 17.6 | 18.3 | 0.7 | 2 | 162 | 36.4 | 33.9 | -2.5 |
| 3 | 187 | 21.4 | 21.9 | 0.5 | 3 | 166 | 35.5 | 32.6 | -2.9 |
| 4 | 170 | 19.9 | 20.5 | 0.7 | 4 | 176 | 37.1 | 34.1 | -3.0 |
| 5 | 169 | 19.8 | 20.5 | 0.6 | 5 | 167 | 36.9 | 33.8 | -3.1 |
| 6 | 163 | 20.2 | 20.8 | 0.6 | 6 | 165 | 36.9 | 33.9 | -3.0 |
| 7 | 172 | 19.6 | 20.0 | 0.4 | 7 | 192 | 37.2 | 35.3 | -1.9 |
| 8 | 173 | 19.9 | 20.5 | 0.6 | 8 | 171 | 35.8 | 33.5 | -2.3 |
| Mean | 171 | 19.4 | 20.0 | 0.6 | Mean | 171 | 36.6 | 33.9 | -2.7 |
| SD | 8 | 1.4 | 1.3 | 0.1 | SD | 9 | 0.6 | 0.7 | 0.4 |

The $I_O$ and $I_{RES}$ values given for each oligonucleotide are mean values taken from Gaussian fits to event histograms for individual experiments.
$\Delta I_{RES}$ is the difference in residual current between the poly(dA) and poly(dC) blockades ($I_{RES}^{Poly(dA)} - I_{RES}^{Poly(dC)}$).

In practice, the small $\Delta I_{RES}$ values were readily determined from event histograms (FIG. 1B). Although the $I_O$ levels of WT and E111N/K147N pores are similar, $I_{RES}$ values, as we had hoped, were higher when oligonucleotides were immobilized within the E111N/K147N pores (FIG. 1C): $I_{RES}^{poly(dA)}$=33.9±0.7% and $I_{RES}^{poly(dC)}$=36.6±0.6%. Remarkably, as well as an increase in the residual current, there is also a change in the sign of $\Delta I_{RES}$, with poly(dA)

blockades giving a lower $I_{RES}$ than poly(dC) oligonucleotide blockades in the E111N/K147N pores: $\Delta I_{RES}$=−2.7±0.4% (FIG. 1C).

Figure 8:
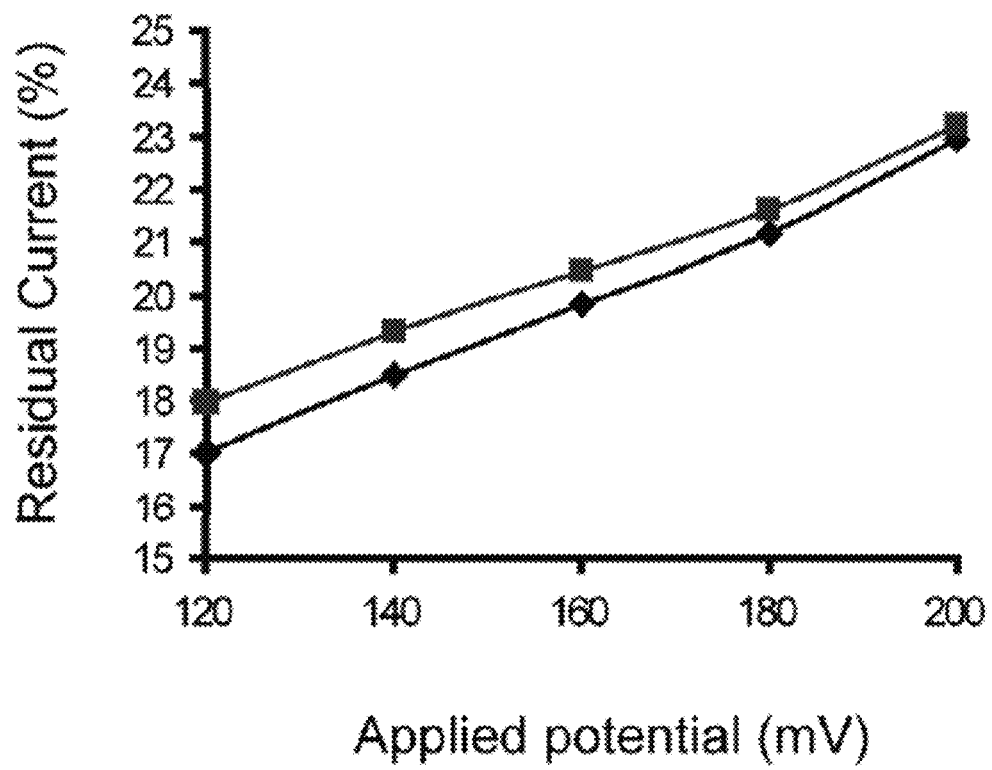
FIG. 8 shows voltage dependence of $I_{RES}$ for WT pores threaded with either poly(dA) (squares) or poly(dC) (diamonds). The data for the graph was obtained by taking mean values from Gaussian fits to histograms of residual current levels for multiple blockades for each oligonucleotide, at various applied potentials. The standard deviation associated with the fitting of the Gaussians is shown.

Nucleic acid homopolymers have been distinguished with the WT α-HL pore by several groups on the basis of differences in $I_{RES}$. Meller and colleagues found that poly (dA) and poly(dC) were difficult to distinguish during translocation through the pore, in part due to the broad distributions of $I_{RES}$ values (Meller, A., Nivon, L., Brandin, E., Golovchenko, J., & Branton, D. (2000) *Proc. Natl. Acad. Sci. USA* 97, 1079-1084). By contrast, when ssDNA was immobilized in the pore with a 3' hairpin (5' threading), Ashkenasy found a $\Delta I_{RES}^{poly(dA)-poly(dC)}$ value of −10.5% (Ashkenasy and colleagues, supra). The value for 3' threading was similar. Interestingly, Purnell and colleagues, using biotin-streptavidin immobilization, found that $\Delta I_{RES}$ depends on whether the 5' or 3' end of the DNA enters the pore first (5' entry, $\Delta I_{RES}^{poly(dA)-poly(dC)}$=+1.2%; 3' entry, $\Delta I_{RES}^{poly(dA)-poly(dC)}$=−2.9%) (Purnell, R. F., Mehta, K. K., & Schmidt, J. J. (2008) Nucleotide identification and orientation discrimination of DNA homopolymers immobilized in a protein nanopore. *Nano Lett* 8, 3029-3034). Our results (5' entry: $\Delta I_{RES}^{poly(dA)-poly(dC)}$=+0.6%) are in rough agreement with the latter work. We note that that $\Delta I_{RES}$ is voltage-dependent (FIG. 8), and that Purnell and colleagues worked at a lower applied potential. It is worth noting that $I_{RES}$ is greater when the DNAs are attached to streptavidin. Perhaps, DNA is more stretched in the electric field within the pore when it is anchored on the cis side. If this is the so, it would be preferable to sequence DNA under similar conditions. This would be the case, for example, when DNA is ratcheted through the pore by an enzyme (Cockroft, S. L., Chu, J., Amorin, M., & Ghadiri, M. R. (2008) *J. Am. Chem. Soc.* 130, 818-820).

Interestingly, the open pore current carried by the WT pore and E111N/K147N are similar at +160 mV (FIG. 6), but the residual currents in the presence of ssDNA are almost twice as high in the mutant pore (e.g. FIG. 1B, C), which be the basis of why E111N/K147N gives better discrimination between poly(dA) and poly(dC). We suggest that the ring of charged lysine and glutamatic acid side chains in the constriction (residues 147 and 111, FIG. 1A), which are replaced with asparagines in the mutant, might have one or more effects, including: a coulombic block to ion transport, or a steric block based either simply on the bulk of the large amino acid side chains, which might "grip" the translocating DNA, or a collapse of the barrel around the DNA. In either case, the current, which is carried largely by hydrated $K^+$ ions while the negatively charged DNA strand is in the pore (Sanchez-Quesada, J., Saghatelian, A., Cheley, S., Bayley, H., & Ghadiri, M. R. (2004) *Angew. Chem. Int. Ed. Engl.* 43, 3063-3067), is reduced in the WT pore and so is base discrimination in terms of differences in absolute current or as percentages of the open pore current ($\Delta I_{RES}$). The actual current levels that are observed cannot be readily rationalized, especially when it is noted that poly(dA) gives the higher residual current in the WT pore and poly(dC) in the E111N/K147N pore. A simplistic conclusion is that the central constriction (comprising residues Lys-147, Glu-111 and Met-113 in the WT) forms a recognition site. This is interesting because Ashkenasy and colleagues (supra) concluded that recognition occurs at the trans exit. In the latter case, the ssDNA was immobilized by 5' or 3' terminal hairpins, which probably enter the pore and perturb recognition that occurs at the constriction. Together, the results imply that more than one recognition element might be present in the β barrel of the α-HL pore. Further experimentation, as described below, supports this view.

2.2 Defining Recognition Elements within the α-HL Pore

We attempted to better define the regions of the α-HL pore that interact with DNA in a base-specific manner (recognition elements) by probing the length of the pore with a set of five oligonucleotides (SEQ ID NOs: 16 to 20), each of which contained a stretch of 5 consecutive adenine nucleotides ($A_5$ oligonucleotides) in an otherwise poly(dC) sequence (FIG. 2A, the locations of the $A_5$ sequences in the figure are justified below). A similar approach for the discovery of base recognition sites was established by Ashkenasay and colleagues (supra). We determined $\Delta I_{RES}$ with respect to a reference poly(dC) oligonucleotide for each of the $A_5$ oligonucleotides (i-v, FIG. 2A) for both the WT and E111N/K147N pores (FIG. 2BC, Table 3).

TABLE 3

Residual currents ($I_{RES}$) for poly(dC) oligonucleotides containing a stretch of five consecutive adenine nucleotides immobilized within WT and E111N/K147N pores.

| | WT | | | | | E111N/K147N | | | |
|---|---|---|---|---|---|---|---|---|---|
| Oligo i-v | $I_O$ (pA) | $I_{RES}^{i-v}$ (%) | $I_{RES}^{pdC}$ (%) | n | $\Delta I_{RES}$ (%) | Oligo i-v | $I_O$ (pA) | $I_{RES}^{i-v}$ (%) | $I_{RES}^{pdC}$ (%) | n | $\Delta I_{RES}$ (%) |
| i | 168 ± 2 | 19.3 ± 0.7 | 19.3 ± 0.7 | 3 | 0.0 ± 0.0 | i | 158 ± 1 | 35.8 ± 1.8 | 35.8 ± 1.8 | 3 | 0.0 ± 0.0 |
| ii | 171 ± 4 | 19.7 ± 0.8 | 19.3 ± 0.7 | 3 | 0.4 ± 0.2 | ii | 162 ± 7 | 35.2 ± 0.1 | 36.8 ± 0.1 | 3 | −1.6 ± 0.1 |
| iii | 178 ± 13 | 22.3 ± 1.3 | 21.1 ± 1.1 | 5 | 1.2 ± 0.3 | iii | 169 ± 8 | 39.0 ± 1.2 | 37.5 ± 0.9 | 4 | 1.5 ± 0.4 |
| iv | 175 ± 11 | 20.1 ± 1.3 | 21.1 ± 1.5 | 3 | −1.0 ± 0.2 | iv | 171 ± 7 | 35.3 ± 0.5 | 37.5 ± 0.9 | 3 | −2.2 ± 0.5 |
| v | 166 ± 14 | 21.3 ± 1.3 | 21.3 ± 1.3 | 3 | 0.0 ± 0.0 | v | 168 ± 8 | 37.8 ± 1.4 | 37.8 ± 1.4 | 3 | 0.0 ± 0.0 |

The $I_O$ and $I_{RES}$ values shown are the mean values from n experiments.
$\Delta I_{RES}$ is the difference in residual current between each $A_5$ oligonucleotide (i-v) (FIG. 2A) and poly(dC) ($I_{RES}^{A5oligo} - I_{RES}^{poly(dC)}$). The errors given are standard deviations.

Our data suggest that when the $A_5$ sequence is closest to the streptavidin anchor (positions 1-5 from the 3' end), the bases are not recognized by the α-HL pore, i.e. $\Delta I_{RES}^{A5oligo-poly(dC)}$=0, for both WT α-HL and E111N/K147N, and the $A_5$ sequence is likely lie within the vestibule. However, when the $A_5$ sequence was in positions 6-10, 11-15, and 16-20, the bases were recognized in both pores (FIG. 26). Importantly, when the $A_5$ sequence was in positions 6-10, the WT and the E111N/K147N pores recognized the DNA in a different way, i.e. for WT α-HL, $\Delta I_{RES}^{A5oligo-poly(dC)}$ was positive (+0.4±0.2%) and for E111N/K147N, $\Delta I_{RES}^{A5oligo-poly(dC)}$ was negative (−1.6±0.1%), suggesting that in this case the $A_5$ sequence lies at the constriction where the mutations are located. Finally, when the $A_5$ sequence was in positions 21-25, no discrimination was seen suggesting that this sequence protrudes through the trans entrance of the pore. Therefore the sequence bounded by positions 6 and 20 from the 3' end of the DNA is likely to lie within the narrow confines of the β barrel, where recognition should be at its strongest. Ashkenasy and colleagues (supra) performed a similar experiment and found that stretches of adenine nucleotides were recognized near the trans entrance, but as noted above they used DNA immobilized with hairpins.

Figure 2:
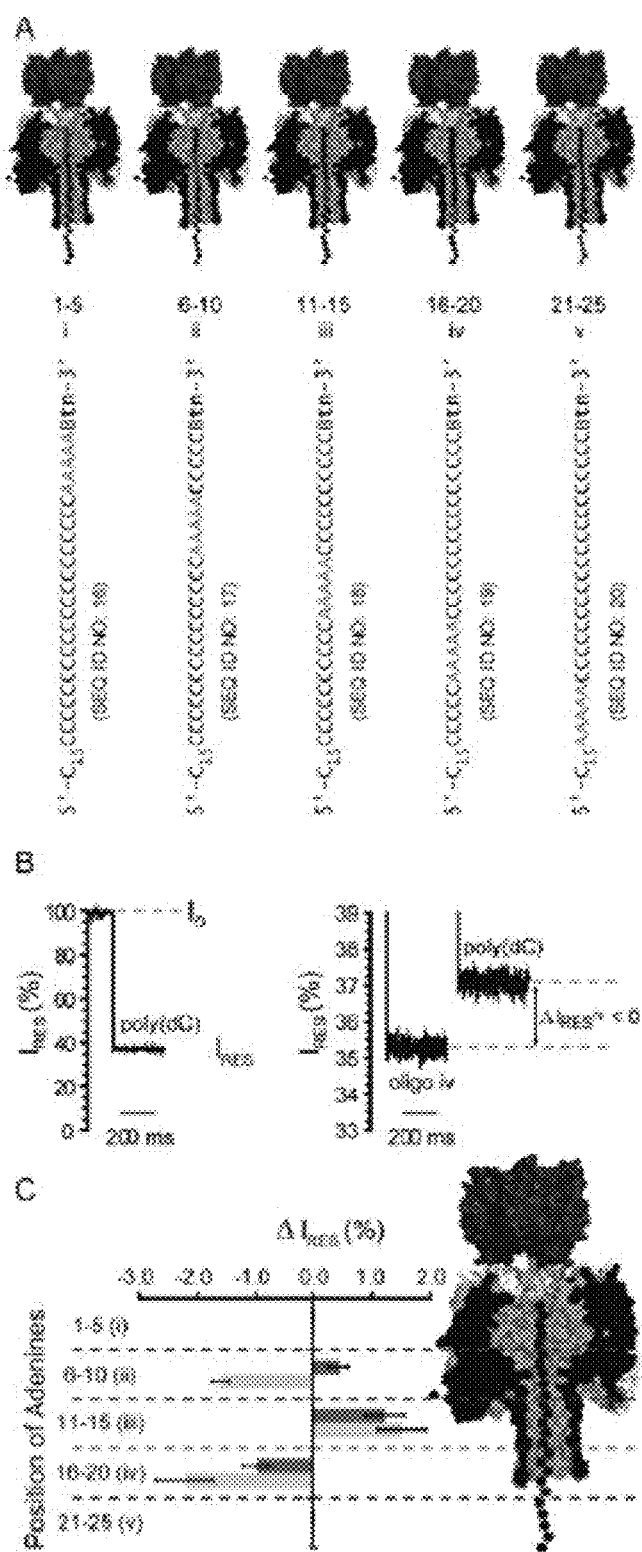
FIG. 2 shows the probing of DNA recognition by the α-HL pore with $A_5$ oligonucleotides. (A) The five oligonucleotides (i-v) containing 5 consecutive adenine nucleotides ($A_5$, red circles) at different positions (numbered from the 3' biotin tag) in an otherwise poly(dC) strand (cytidine nucleotides are shown as blue circles). Only the first 25 of the 40 nucleotide-long sequences are shown. (B, left) The stepwise reduction from the open current value (pore not blocked with DNA) to a residual current ($I_{RES}$) level of ~37% when the E111N/K147N pore becomes blocked with a poly(dC) oligonucleotide. (B, right) The $I_{RES}$ levels when a pore is blocked with oligonucleotides of different sequence (oligo iv and poly(dC) are shown). (C) Residual current difference ($\Delta I_{RES}$) between the blockade by oligonucleotides i-v (panel A) and poly(dC)40 for WT (green bars) and E111N/K147N (orange bars) α-HL pores ($\Delta I_{RES}=I_{RES}^{i-v}-I_{RES}^{poly(dC)}$). The probable location of the adenine ($A_5$) stretch of each oligonucleotide when immobilized with an α-HL pore is indicated (right).

The ssDNA in the pore is elongated compared to its conformation in solution. First, the applied potential produces a force on the DNA, which can be estimated to be ~8 pN, by the following argument. Let there be ~30 nt in the entire lumen of the pore (about the same as there would be for a strand in a double helix 10 nm in length) and therefore ~15 nt in the transmembrane β barrel. The experimentally determined effective charge on each base is ~0.1 e (Sauer-Budge, A. F., Nyamwanda, J. A., Lubensky, D. K., & Branton, D. (2003) *Phys. Rev. Lett.* 90, 238101-238101-238101-238104). This low value is consistent with the theory of Zhang and Shklovskii (Zhang, J. & Shklovskii, B. I. (2007) *Phys Rev E Stat Nonlin Soft Matter Phys* 75, 021906). Therefore, the overall charge is $\sim 2.4 \times 10^{-19}$ C. The field is 0.16 V over the 5 nm of the barrel or $3.2 \times 10^7$ Vm$^{-1}$. Therefore, the force (F=QE) is ~8 pN. Under this force, ssDNA has a similar extension to the B-form of dsDNA (Bustamante, C., Smith, S. B., Liphardt, J., & Smith, D. (2000) *Curr. Op. Struct. Biol.* 10, 279-285), so there would indeed be ~30 nt in the full length of the pore and about 15 nt in the β barrel. Second, the effects of enforced confinement would serve to elongate the DNA still further (Han, J. & Craighead, H. G. (2000) *Science* 288, 1026-1029). Taking into account how streptavidin might dock on the cis surface of the α-HL pore, the location of the biotin binding site within streptavidin and the length of the linker between the DNA and the biotinyl group (FIG. 7), the 3' end of the DNA would be within the lumen and about 15 _from the cis entrance (FIG. 1). Therefore, it is reasonable that the DNA strand is located with residues 6 to 20 within the β barrel (FIG. 2).

2.3 Discrimination of Single Adenine Nucleotides

Figure 3:
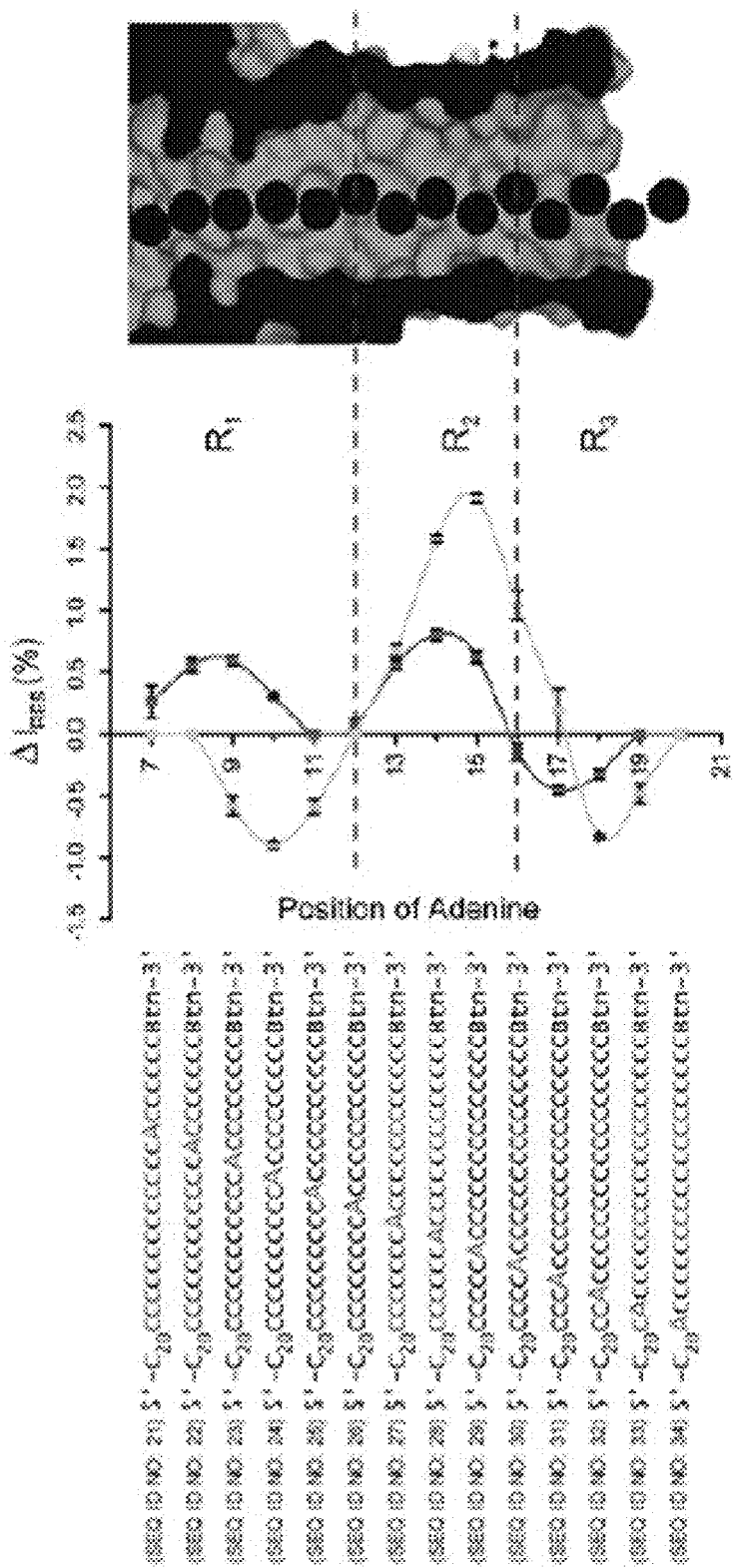
FIG. 3 shows discrimination of a single adenine nucleotide by α-HL. The graph (middle) indicates the differences in residual current ($\Delta I_{RES}$ values) between blockades caused by a poly(dC) oligonucleotide containing a single adenine nucleotide (the sequence of each oligonucleotide is shown to the left) and blockades caused by poly(dC)40 for WT (green) and E111N/K147N (orange) α-HL pores. $R_1$, $R_2$ and $R_3$ represent the three proposed recognition sites in the α-HL nanopore. Their probable locations are indicated on the cross-section of the β barrel domain of the α-HL pore (right).

The results of the $A_5$ scan show that the α-HL pore can recognize bases in ssDNA and contains at least three recognition sites within the β barrel. Of course, to be of use in sequencing intact ssDNA strands, the α-HL pore must be able to detect single nucleotides. Therefore, we further defined the recognition sites by moving a single A base through a poly(dC) background and comparing the residual current with that of poly(dC) itself. A set of fourteen poly(dC) oligonucleotides was made (SEQ ID NOs: 21 to 34), each containing a single adenine ($A_1$) nucleotide (Askenashay and colleagues, supra). The $A_1$ substitutions were in positions 7 to 20 relative to the 3' biotin tag (FIG. 3). $\Delta I_{RES}$ (with respect to poly(dC)) was plotted against the position of the adenine nucleotide for both the WT and E111N/K147N pores (FIG. 3, Table 4).

TABLE 4

Residual currents ($I_{RES}$) for poly(dC) and oligonucleotides that contain a single adenine nucleotide.

| Position of adenine | WT | | | | Position of adenine | E111N/K147N | | | |
|---|---|---|---|---|---|---|---|---|---|
| | $I_O$ (pA) | $I_{RES}^{A1}$ (%) | $I_{RES}^{pdC}$ (%) | n | $\Delta I_{RES}$ (%) | | $I_O$ (pA) | $I_{RES}^{A1}$ (%) | $I_{RES}^{pdC}$ (%) | n | $\Delta I_{RES}$ (%) |
| 7 | 167 ± 1 | 20.4 ± 0.4 | 20.2 ± 0.6 | 3 | 0.3 ± 0.2 | 7 | 169 ± 10 | 37.0 ± 0.4 | 37.0 ± 0.4 | 3 | 0.0 ± 0.0 |
| 8 | 170 ± 4 | 20.1 ± 0.4 | 19.6 ± 0.4 | 3 | 0.6 ± 0.1 | 8 | 163 ± 2 | 34.9 ± 3.9 | 34.9 ± 3.9 | 3 | 0.0 ± 0.0 |
| 9 | 169 ± 3 | 20.5 ± 0.5 | 19.9 ± 0.4 | 3 | 0.6 ± 0.1 | 9 | 163 ± 1 | 34.3 ± 3.8 | 34.9 ± 3.7 | 3 | −0.6 ± 0.1 |
| 10 | 173 ± 2 | 20.3 ± 0.2 | 20.0 ± 0.2 | 4 | 0.3 ± 0.0 | 10 | 175 ± 4 | 36.1 ± 0.4 | 37.0 ± 0.4 | 3 | −0.9 ± 0.1 |
| 11 | 168 ± 8 | 20.0 ± 0.2 | 20.0 ± 0.2 | 3 | 0.0 ± 0.0 | 11 | 165 ± 5 | 36.6 ± 0.1 | 37.2 ± 0.1 | 3 | −0.6 ± 0.1 |
| 12 | 173 ± 12 | 20.1 ± 0.1 | 20.0 ± 0.2 | 3 | 0.1 ± 0.1 | 12 | 164 ± 6 | 35.0 ± 2.2 | 35.0 ± 2.2 | 3 | 0.0 ± 0.0 |
| 13 | 168 ± 6 | 20.4 ± 0.3 | 19.8 ± 0.3 | 3 | 0.5 ± 0.1 | 13 | 164 ± 6 | 37.0 ± 1.8 | 36.3 ± 1.7 | 3 | 0.7 ± 0.1 |
| 14 | 170 ± 8 | 20.5 ± 0.7 | 19.7 ± 0.6 | 3 | 0.8 ± 0.1 | 14 | 167 ± 9 | 37.1 ± 1.5 | 35.5 ± 1.4 | 3 | 1.6 ± 0.1 |
| 15 | 172 ± 5 | 20.7 ± 0.3 | 20.0 ± 0.3 | 3 | 0.6 ± 0.1 | 15 | 164 ± 3 | 38.4 ± 2.2 | 36.5 ± 2.2 | 3 | 1.9 ± 0.1 |
| 16 | 170 ± 5 | 19.9 ± 0.2 | 20.0 ± 0.1 | 3 | −0.1 ± 0.1 | 16 | 161 ± 5 | 37.4 ± 1.3 | 36.4 ± 1.2 | 3 | 1.0 ± 0.2 |
| 17 | 172 ± 5 | 19.3 ± 0.4 | 19.8 ± 0.4 | 3 | −0.4 ± 0.0 | 17 | 165 ± 3 | 37.0 ± 0.3 | 36.9 ± 0.1 | 3 | 0.2 ± 0.3 |
| 18 | 171 ± 6 | 20.2 ± 0.9 | 20.5 ± 0.9 | 3 | −0.3 ± 0.1 | 18 | 165 ± 4 | 36.2 ± 0.3 | 37.0 ± 0.4 | 3 | −0.9 ± 0.0 |
| 19 | 172 ± 5 | 20.0 ± 0.3 | 20.0 ± 0.3 | 3 | 0.0 ± 0.0 | 19 | 170 ± 17 | 36.1 ± 1.6 | 36.6 ± 1.5 | 3 | −0.5 ± 0.1 |
| 20 | 173 ± 7 | 20.5 ± 0.9 | 20.5 ± 0.9 | 3 | 0.0 ± 0.0 | 20 | 166 ± 5 | 35.9 ± 1.3 | 35.9 ± 1.3 | 3 | 0.0 ± 0.0 |

The position of the adenine in the $A_1$ nucleotide (nucleotides 7-20) is numbered relative to the 3' biotin tag.
The $I_O$ and $I_{RES}$ values are the mean values from n experiments.
$\Delta I_{RES}$ is defined as the difference in residual current between an $A_1$ oligonucleotides and poly(dC) ($I_{RES}^{A1oligo} - I_{RES}^{dC}$).
The errors given are standard deviations.

Both pores were able to discriminate single adenine nucleotides at multiple positions within the oligonucleotide chain. Remarkably, the pattern of $\Delta I_{RES}$ values for the $A_1$ oligonucleotides mirrored the pattern seen with the $A_5$ oligonucleotides (FIGS. 2, 3). Further, the data suggest that there are indeed three recognition sites within the barrel, which have been designated $R_1$, $R_2$ and $R_3$ (FIG. 3). These experiments further demonstrate that a single base (A versus C) can be recognized in an otherwise identical strand at all three sites. By contrast, in the hairpin-anchor experiments of Ashkenasy (supra), recognition was confined to the trans entrance. When the WT and E111N/K147N pores are compared, the $A_1$ scans appear to be about 1 nt out of phase, suggesting that the extent of elongation of the ssDNA may differ slightly in the two pores.

2.4 Probing the Three Recognition Sites of α-HL for Four-Base Discrimination

In addition to the detection of individual bases, to sequence ssDNA, α-HL pores must also be able to distinguish between G, A, T and C within a DNA chain. To examine this possibility, the WT and E111N/K147N pores were probed with three sets of four oligonucleotides (SEQ ID NOs: 35 to 46). Each oligonucleotide was a homopolymer (poly(dC)), except at a specific position, where it was substituted with either G, A, T and C (the latter oligonucleotide being poly(dC) itself). Each of the three sets had substitutions at a different position in the sequence, which were designed to probe the $R_1$, $R_2$ and $R_3$ recognition sites.

The first set of oligonucleotides had the G, A, T or C substitution at position 9 (from the 3' end) and was designed to probe $R_1$ (FIG. 4A). Although there is some discrimination between the four oligonucleotides in this set, neither the WT nor the E111N/K147N pore is able to distinguish all four bases. The second set had the G, A, T or C substitution at position 14 and was designed to probe $R_2$ (FIG. 4B). In this case, both the WT and E111N/K147N pores clearly separated C, T, A and G, in order of increasing $I_{RES}$. The span between C and G is far greater for the E111N/K147N pores ($\Delta I_{RES}$=2.8%) than it is for WT pores ($\Delta I_{RES}$=1.2%). The final set had the G, A, T or C substitution at position 18 to probe $R_3$ (FIG. 4C). In this case, only the E111N/K147N pores are able distinguish the four bases, but in the reverse order, viz. G, A, T and C, and the spread of $I_{RES}$ values is not as large as seen with the set substituted at position 14.

For exonuclease sequencing, in which bases are sequentially cleaved from a DNA strand, all four DNA bases can be identified as deoxyribonucleoside 5'-monophosphates by using an engineered α-HL pore (Astier, Y., Braha, O., & Bayley, H. (2006) *J Am Chem Soc* 128, 1705-1710). In this case there are no interfering neighboring bases during detection. By contrast, the ability to sequence ssDNA would require the recognition of individual nucleotides in a heteropolymeric background and therefore we tested this possibility. We were uncertain of the outcome because homopolymeric nucleic acids have been reported to form secondary structure including extended helices. (Buhot, A. & Halperin, A. (2004) *Phys Rev E Stat Nonlin Soft Matter Phys* 70, 020902). Therefore, it was possible that the pronounced differences in residual current that we had observed were the result of disruptions in the DNA structure that caused changes in the conformation of the DNA within the nanopore, which in turn affected current flow.

2.5 Single Nucleotide Discrimination within a Heteropolymeric Sequence

Figure 5:
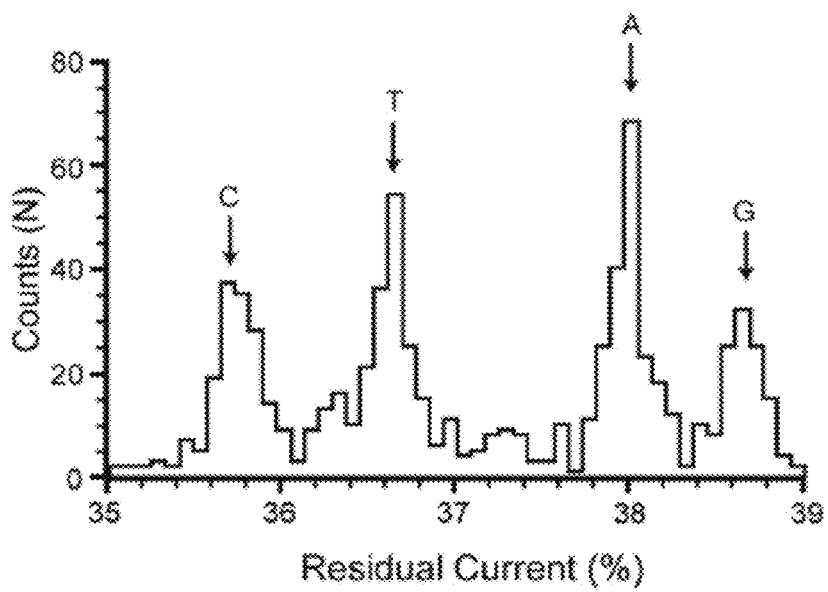
FIG. 5 shows probing the E111N/K147N α-HL pore for single nucleotide discrimination in a heteropolymeric oligonucleotide. Histogram (top) of residual current levels for E111N/K147N pores interrogated with four heteropolymeric DNA strands (center) that differ at only one position (large letter). Gaussian fits were performed for each peak, and the mean value of the residual current for each oligonucleotide (and the standard deviation) is displayed (bottom).

To examine discrimination within a heteropolymer, the most promising site, namely $R_2$ in E111N/K147N was tested using SEQ ID NOs: 47 to 50. All four bases at position 14 in a heteropolymer were recognized with the same order of residual current (C, T, A and G) as seen in the homopolymeric background (FIG. 5). The immediate context of the identified bases (N) was 5' . . . CTGNACA . . . 3', by comparison with 5' . . . CCCNCCC . . . 3' in the homopolymer. The span between C and G in the residual current histogram ($\Delta I_{RES}$=2.9%) was similar to that seen in the homopolymeric background ($\Delta I_{RES}$=2.8%), although the spacing between the four peaks differed in detail (FIG. 5). The sequence we chose does not contain secondary structure such as hairpins, as predicted by the mfold algorithm (Zuker, M. (2003) *Nucleic Acids Res* 31, 3406-3415), and is unlikely to form π-stacked helices (Buhot and colleagues, supra).

3 Example 2

To facilitate the observation of base recognition derived from current block, DNA strands can be immobilized within the α-HL pore by using a terminal hairpin or a biotin•streptavidin complex, which improves the resolution of the currents associated with individual nucleotides, because of the prolonged observation time (N. Ashkenasy, J. Sánchez-Quesada, H. Bayley, M. R. Ghadiri, *Angew. Chem. Int. Ed. Engl.* 2005, 44, 1401). The immobilized strands reduce the open pore current level, $I_O$, to a level $I_B$. In this Example, we quote the residual current $I_{RES}$ as a percentage of the open pore current: $I_{RES}=(I_B/I_O)\times 100$. By using the biotin•streptavidin approach, we recently demonstrated that the 5 nm-long β barrel of the α-HL nanopore contains three recognition sites, $R_1$, $R_2$ and $R_3$, each capable of recognizing single nucleotides within DNA strands (D. Stoddart, A. Heron, E. Mikhailova, G. Maglia, H. Bayley, *Proc. Natl. Acad. Sci. USA* 2009, 106, 7702). $R_1$ is located near the internal constriction in the lumen of the pore and recognizes bases at positions ~8 to 12 (bases are numbered from the 3' end of synthetic oligonucleotide probes). $R_2$ is located near the middle of the □ barrel and discriminates bases at positions ~12 to 16. $R_3$ recognizes bases at positions ~17 to 20 and is located near the trans entrance of the barrel.

Figure 9:
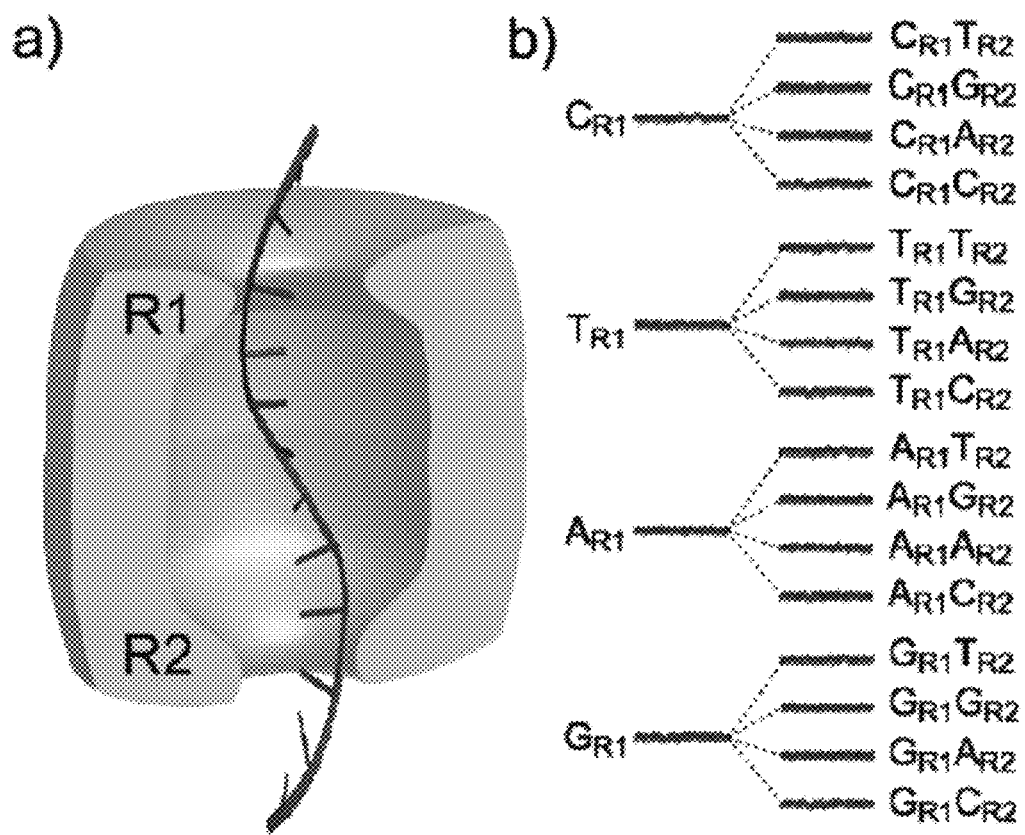
FIG. 9 shows that two heads are better than one. a) A hypothetical nanopore sensor (green) with two reading heads, $R_1$ and $R_2$, which could in principle extract more sequence information from a DNA strand (red) than a device with a single reading head. b) To illustrate the idea, we assume that the four bases of DNA at reading head $R_1$ produce 4 distinct current levels (widely dispersed as shown). Each of the levels is split into 4 additional levels (with a lesser dispersion, for the purpose of illustration) by the second reading head $R_2$, yielding 16 current levels in total and providing redundant information about the DNA sequence.

We surmised that it might be advantageous to use more than one of the recognition points for DNA sequence determination. Consider a nanopore with two reading heads, $R_1$ and $R_2$, each capable of recognizing all four bases (FIG. 9). If the first site, $R_1$ produces a large dispersion of current levels for the four bases and the second site, $R_2$ produces a more modest dispersion, 16 current levels, one for each of the 16 possible base combinations, would be observed as DNA molecules are translocated through the nanopore. Therefore, at any particular moment, the current signal would offer information about two positions in the sequence, rather than just one, providing redundant information; each base is read twice, first at $R_1$ and secondly at $R_2$. This built-in proof-reading mechanism would improve the overall quality of sequencing.

In the WT α-HL pore, $R_2$ is capable of discriminating between each of the four DNA bases (when the bases are placed at position 14, in an otherwise poly(dC) oligonucleotide). With the E111N/K147N mutant (NN), in which the charged residues at the constriction have been removed, a greater current flows through the pore when it is blocked with a DNA•streptavidin complex. This increase in $I_{RES}$ in the NN mutant leads to a greater dispersion of the current levels arising from different DNAs, and thereby improves base discrimination at $R_2$ and $R_3$, compared to WT. However, in NN, the ability of $R_1$ to recognize bases is weakened, presumably due to a reduced interaction between the pore and the DNA at the constriction, where amino acid residues 111 and 147 are located. Therefore, to further tune recognition at $R_1$, substitutions at position 113, which also forms part of the constriction, were examined. The mutation M113Y was the most effective.

The E111N/K147N/M113Y (NNY) and NN pores displayed similar discrimination of bases by $R_2$; bases at position 14, within poly(dC), are separated in the same order, namely C, T, A and G, in order of increasing $I_{RES}$, and with a similar dispersion between C and G: $\Delta I_{RES}^{G-C}=I_{RES}^{G}-I_{RES}^{C}=+2.8\pm 0.1\%$ (n=3) for NN and +2.9±0.1% (n=3) for NNY (FIG. 10a). It should be noted that the $\Delta I_{RES}$ values, which were readily determined from event histograms, showed little experimental variation, while the residual current values ($I_{RES}$) showed variation that exceeded $\Delta I_{RES}$. NNY displayed vastly improved base recognition properties at $R_1$ compared to the WT and NN pores. In the NN mutant, $R_1$ is not capable of discriminating all four bases (when they are located at position 9 within poly(dC)), and the magnitude of the current differences between the bases is quite small; the difference between the most widely dispersed bases, A and C ($\Delta I_{RES}^{A-C}$) is only $-0.4\pm0.1\%$ (n=5, A giving a lower residual current than C). However, the NNY mutant is capable of discriminating between T, G, A and C, in order of increasing $I_{RES}$ (FIG. 10b), and the dispersion of current levels is much larger, $\Delta I_{RES}^{T-C}=-2.8\pm0.2\%$ (n=5). It is remarkable that the single M113Y mutation is capable of turning a weakly discriminating $R_1$ site in the NN mutant into a strong site in the NNY mutant. Possibly, the tyrosines at position 113 improve discrimination at $R_1$ through aromatic stacking or hydrogen bonding interactions with the immobilized bases (G. Hu, P. D. Gershon, A. E. Hodel, F. A. Quiocho, Proc. Natl. Acad. Sci. USA 1999, 96, 7149). But, we are unsure of what properties of the bases cause the dispersion of the current levels, although it is clear that size is not the only factor, as a T at $R_1$ produces a greater current block than the larger purine bases.

We determined whether the NNY mutant, which has two strong recognition points ($R_1$ and $R_2$), could behave like the two-head sensor envisaged in FIG. 9 by using a library containing 16 oligonucleotides comprising poly(dC) with substitutions at position 9 (to probe $R_1$) and position 14 (to probe $R_2$). The sequence of a given oligonucleotide is designated: $X_9X_{14}$, where X represents a defined base; G, A, T or C, and 9 and 14 gives the position of the base (relative to the biotin tag). These oligonucleotides are shown in SEQ ID NOs: 51 to 66 and Table 5 below.

TABLE 5

Sequences of the oligonucleotides used in this study.

| Oligonucleotide name | SEQ ID NO: | Oligonucleotide sequence (5'→3') |
|---|---|---|
| $C_9C_{14}$ | 51 | CCCCCCCCCCCCCCCCCCCCCCCCCCCCCCCCCCCCCCB |
| $C_9T_{14}$ | 52 | CCCCCCCCCCCCCCCCCCCCCCCCCCCTCCCCCCCCCCCB |
| $C_9A_{14}$ | 53 | CCCCCCCCCCCCCCCCCCCCCCCCCCCACCCCCCCCCCCB |
| $C_9G_{14}$ | 54 | CCCCCCCCCCCCCCCCCCCCCCCCCCCGCCCCCCCCCCCB |
| $T_9C_{14}$ | 55 | CCCCCCCCCCCCCCCCCCCCCCCCCCCCCCCTCCCCCCCCB |
| $A_9C_{14}$ | 56 | CCCCCCCCCCCCCCCCCCCCCCCCCCCCCCCCACCCCCCCB |
| $G_9C_{14}$ | 57 | CCCCCCCCCCCCCCCCCCCCCCCCCCCCCCCCGCCCCCCCB |
| $T_9A_{14}$ | 58 | CCCCCCCCCCCCCCCCCCCCCCCCCCCACCCCTCCCCCCCCB |
| $A_9A_{14}$ | 59 | CCCCCCCCCCCCCCCCCCCCCCCCCCCACCCCACCCCCCCCB |
| $G_9A_{14}$ | 60 | CCCCCCCCCCCCCCCCCCCCCCCCCCCACCCCGCCCCCCCCB |
| $T_9G_{14}$ | 61 | CCCCCCCCCCCCCCCCCCCCCCCCCCCGCCCCTCCCCCCCCB |
| $A_9G_{14}$ | 62 | CCCCCCCCCCCCCCCCCCCCCCCCCCCGCCCCACCCCCCCCB |
| $G_9G_{14}$ | 63 | CCCCCCCCCCCCCCCCCCCCCCCCCCCGCCCCGCCCCCCCCB |
| $T_9T_{14}$ | 64 | CCCCCCCCCCCCCCCCCCCCCCCCCCCTCCCCTCCCCCCCCB |
| $A_9T_{14}$ | 65 | CCCCCCCCCCCCCCCCCCCCCCCCCCCTCCCCACCCCCCCCB |
| $G_9T_{14}$ | 66 | CCCCCCCCCCCCCCCCCCCCCCCCCCCTCCCCGCCCCCCCCB |

B represents the 3' biotin-TEG tag and linker. Each oligo $X_9X_{14}$ is a member of the set $N_9N_{14}$.

First, we tested whether the identity of the base at position 14 ($R_2$) affected base recognition at position 9 ($R_1$). NNY pores were separately probed with 4 sets of 4 oligonucleotides: $N_9C_{14}$, $N_9A_{14}$, $N_9T_{14}$ and $N_9G_{14}$ (where N=G, A, T or C, FIG. 10b-e, respectively). Despite the variation of the base at position 14, the distribution of the current levels for each set of 4 oligonucleotides, is remarkably similar (Table 6). This suggests that recognition at $R_1$ (i.e. the order and dispersion of the peaks in the histograms) is only weakly influenced by the base occupying $R_2$.

TABLE 6

Mean residual current differences ($\Delta I_{RES}$) between poly(dC) oligonucleotides that contain nucleotide substitutions at position 9 (to probe $R_1$) and/or position 14 (to probe $R_2$).

| Oligo-nucleotide set | Residual Current difference (%) | | |
|---|---|---|---|
| $C_9N_{14}$ | $\Delta I_{RES}^{C9A14-C9C14}$ +1.4 ± 0.0 | $\Delta I_{RES}^{C9T14-C9C14}$ +1.1 ± 0.0 | $\Delta I_{RES}^{C9G14-C9C14}$ +2.9 ± 0.1 |
| $N_9C_{14}$ | $\Delta I_{RES}^{A9C14-C9C14}$ -1.4 ± 0.1 | $\Delta I_{RES}^{T9C14-C9C14}$ -2.8 ± 0.2 | $\Delta I_{RES}^{G9C14-C9C14}$ -2.0 ± 0.1 |
| $N_9A_{14}$ | $\Delta I_{RES}^{A9A14-C9A14}$ -1.5 ± 0.1 | $\Delta I_{RES}^{T9A14-C9A14}$ -3.2 ± 0.1 | $\Delta I_{RES}^{G9A14-C9A14}$ -2.1 ± 0.1 |
| $N_9T_{14}$ | $\Delta I_{RES}^{A9T14-C9T14}$ -1.6 ± 0.1 | $\Delta I_{RES}^{T9T14-C9T14}$ -2.9 ± 0.1 | $\Delta I_{RES}^{G9T14-C9T14}$ -2.1 ± 0.1 |

TABLE 6-continued

Mean residual current differences ($\Delta I_{RES}$) between poly(dC) oligonucleotides that contain nucleotide substitutions at position 9 (to probe $R_1$) and/or position 14 (to probe $R_2$).

| Oligo-nucleotide set | Residual Current difference (%) | | |
|---|---|---|---|
| $N_9G_{14}$ | $\Delta I_{RES}^{A9G14-C9G14}$ $-1.1 \pm 0.1$ | $\Delta I_{RES}^{T9G14-C9G14}$ $-2.8 \pm 0.1$ | $\Delta I_{RES}^{G9G14-C9G14}$ $-1.7 \pm 0.2$ |

Figure 10:
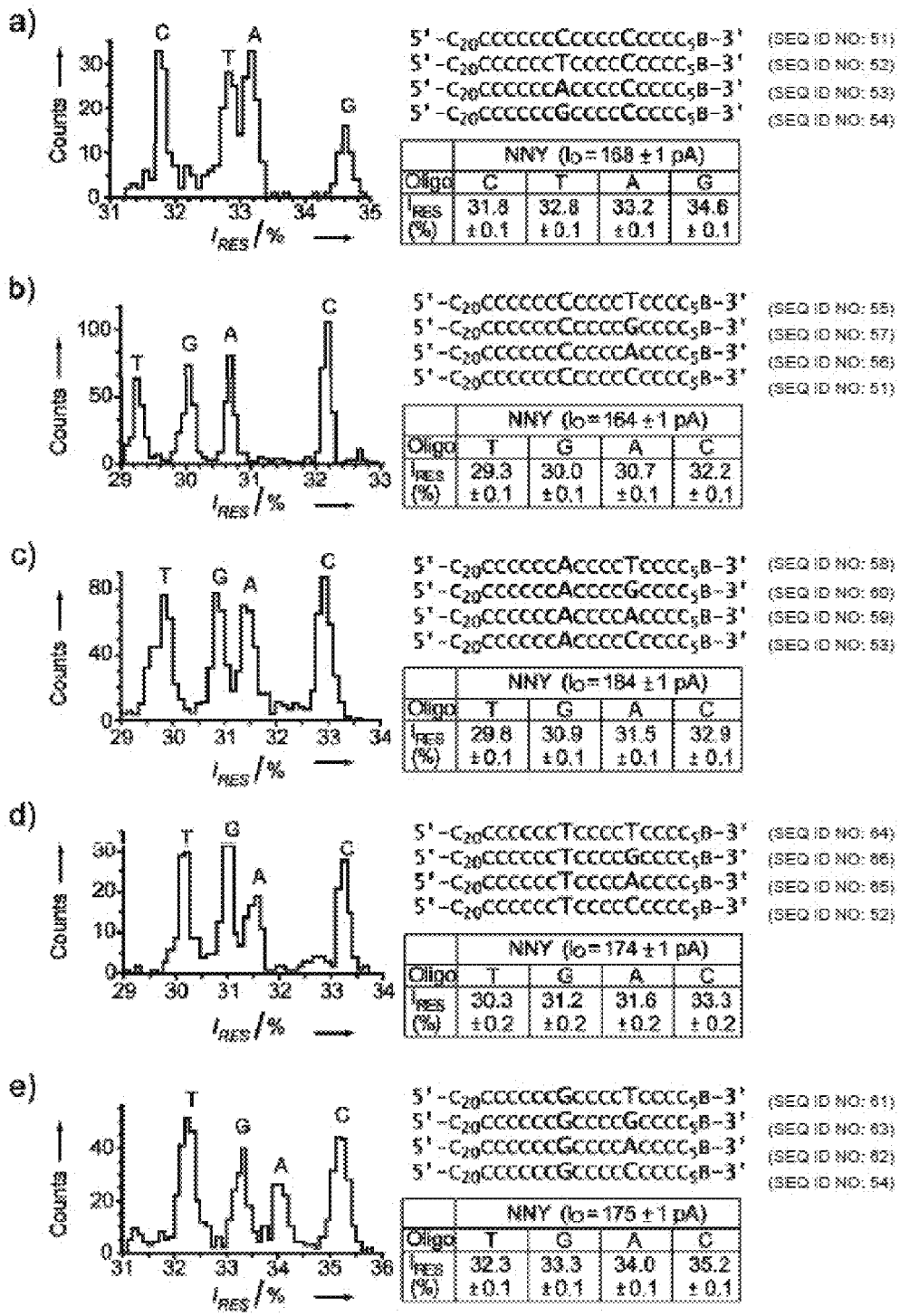
FIG. 10 shows four-base discrimination at $R_1$ and $R_2$, by an engineered αHL nanopore. Histograms of residual current levels for E111N/K147N/M113Y (NNY) pores are shown (left), for a set of 4 oligonucleotides (right). B represents the 3' biotin-TEG extension. Each experiment was conducted at least three times, and the results displayed in the figure are from a single experiment. When the oligonucleotides are driven into the α-HL pore the substituted nucleotides are positioned at $R_1$ (red) or $R_2$ (green). Gaussian fits were performed for each peak in the histograms.

The positions of the substitutions are relative to the 3' biotin tag.
The sequence of each oligonucleotide is abbreviated as $X_9X_{14}$ (SEQ ID NOs: 51 to 66).
The mean $\Delta I_{RES}$ value (±s.d.) is for at least three experiments.
$\Delta I_{RES}$ is directly measured as the difference between the residual current levels of two specified oligonucleotides (FIG. 10).
In the uppermost row (oligonucleotide set $C_9N_{14}$), $\Delta I_{RES} = I_{RES}^{C9N14} - I_{RES}^{C9C14}$ (FIG. 10a).
In the other four rows, $\Delta I_{RES} = I_{RES}^{N9X14} - I_{RES}^{C9X14}$ (FIG. 10b-e).

In the postulated two-head sensor, recognition point $R_1$ produces a large current dispersion, while that produced by $R_2$ is more modest (FIG. 9b). However, in the case tested, the NNY pore, $R_1$ and $R_2$ produce dispersions of similar magnitude ($\Delta I_{RES}^{T-C}=-2.8\pm0.2\%$ and $\Box I_{RES}^{G-C}+2.9\pm0.1\%$, respectively, FIG. 10ab). Further, the slight dependence of recognition at $R_1$ on the base occupying $R_2$ (Table 6, compare the columns for rows two through five) was not considered in the proposed scheme (FIG. 9). Assuming that the effects of each base at each recognition point on the change in current level are additive, and by using the directly determined $\Delta I_{RES}$ values in Table 6, we can predict the distribution of $I_{RES}$ values for each of the sixteen sequences $N_9N_{14}$ (SEQ ID NOs: 51 to 66), relative to poly(dC), which is set as zero (FIG. 11).

For example, consider the sequence $T_9A_{14}$ (SEQ ID NO: 58). We can predict the unknown $\Delta I_{RES}^{T9A14-C9C14}$ (these two sequences were not compared directly, FIG. 10) by using experimentally determined $\Delta I_{RES}$ values (Table 5): $\Delta I_{RES}^{T9A14-C9A14}=-3.2\pm0.1\%$ and $\Delta I_{RES}^{C9A14-C9C14}=+1.4\pm0.0\%$. By adding these values together, we find $\Delta I_{RES}^{T9A14-C9C14}=-1.8\pm0.1\%$. The use of $I_{RES}$ rather than experimental $\Delta I_{RES}$ values leads to unacceptable errors in predicted $\Delta I_{RES}$ values.

Figure 11:
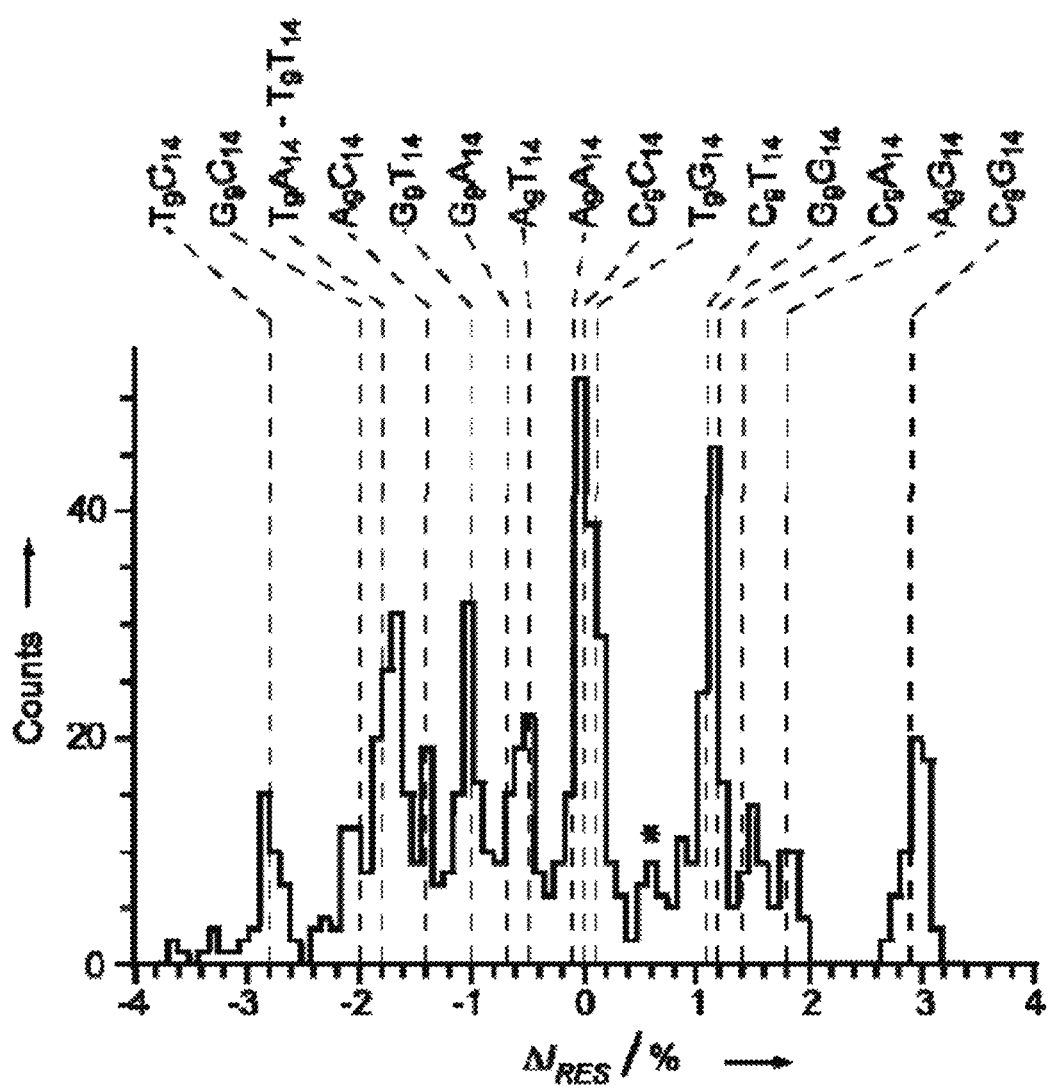
FIG. 11 shows the predicted and experimental residual current level differences ($\Delta I_{RES}$) observed when NNY pores are interrogated with oligonucleotides which simultaneously probe $R_1$ and $R_2$. E111N/K147N/M113Y (NNY) pores were probed with 16 oligonucleotides, with the sequence 5'-CCCCCCCCCCCCCCCCCCCCCCCCCCCCNCCCCNC-CCCCCCCB-3', where N is A, T, G or C ($N_9N_{14}$, Table 5, SEQ ID NOs: 51-66). A histogram displaying the residual current level differences for blockades by the various oligonucleotides, relative to the mean blockade produced by poly(dC) is shown. The current level for poly(dC) is set as zero. Blockades which have a residual current level lower than poly(dC) have negative $\Delta I_{RES}$ values and blockades which have higher residual current levels than poly(dC) have positive $\Delta I_{RES}$ values. The grey dashed lines show the predicted residual current levels, based on the $\Delta I_{RES}$ data displayed in Table 5 (see Example 2). The peak denoted * arises from non-specific blockades and is not considered in the analysis.

All remaining $\Delta I_{RES}$ values were predicted in the same way and are shown in FIG. 11 as dashed grey lines. Only two sequences ($T_9T_{14}$ and $T_9A_{14}$) were predicted to overlap directly. However, given the present resolution of our electrical recordings, three additional sequences were expected to remain unresolved; for example, $A_9A_{14}$ was predicted to have $\Delta I_{RES}^{A9A14-C9C14}=-0.1\pm0.1\%$ and it was therefore likely to overlap with $C_9C_{14}$. Indeed, when all 16 sequences ($N_9N_{14}$, Table 5) were used simultaneously to probe NNY pores, the histograms of the residual current levels consistently contained 11 resolvable sequence-specific peaks (FIG. 11). The predicted $\Delta I_{RES}$ values match well with the measured $\Delta I_{RES}$ values, with the observed mean $\Delta I_{RES}$ values within the error of the predicted values. We surmise that current flow is restricted at $R_1$ and $R_2$, and that the effects of the two recognition points are approximately additive, when $\Delta I_{RES}$ values are small, like the effect of two small resistances in series in an electrical circuit.

Although, the 16 DNA sequences did not produce 16 discrete current levels, we were able to resolve 11. A perfect 16-level system of two reading heads would read each position in a sequence twice, while a perfect single reading head would read the sequence just once. Therefore, although the 11-level system is imperfect, it does yield additional, redundant information about each base, which would provide more secure base identification than a single reading head. It might be thought that a third reading head would improve matters. However, in this case, the number of possible base combinations would increase from 16 to 64. Even if these levels could be dispersed across the entire current spectrum of the α-HL pore (from almost open to almost closed), it is unlikely that the 64 levels could be separated owing to the electrical noise in the system, even under the low bandwidth conditions used here. Under the high applied potentials required for threading, DNA translocates very quickly through the α-HL pore (at a few μs per base) and the situation would be exacerbated by the need for high data acquisition rates and the consequential increase in noise. Even enzyme-mediated threading at one-thousandth of the rate for free DNA will present difficulties. Therefore, it seems likely that a two reading-head sensor is optimal, and our next step will be to remove the superfluous reading head $R_3$.

```
                         Sequence listing

SEQ ID NO: 1
(WT α-HL)

1 ATGGCAGATT CTGATATTAA TATTAAAACC GGTACTACAG ATATTGGAAG CAATACTACA GTAAAAACAG
    71 GTGATTTAGT CACTTATGAT AAAGAAAATG GCATGCACAA AAAAGTATTT TATAGTTTTA TCGATGATAA
   141 AAATCACAAT AAAAAACTGC TAGTTATTAG AACAAAAGGT ACCATTGCTG GTCAATATAG AGTTTATAGC
   211 GAAGAAGGTG CTAACAAAAG TGGTTTAGCC TGGCCTTCAG CCTTTAAGGT ACAGTTGCAA CTACCTGATA
   281 ATGAAGTAGC TCAAATATCT GATTACTATC CAAGAAATTC GATTGATACA AAAGAGTATA TGAGTACTTT
   351 AACTTATGGA TTCAACGGTA ATGTTACTGG TGATGATACA GGAAAAATTG GCGGCCTTAT TGGTGCAAAT
   421 GTTTCGATTG GTCATACACT GAAATATGTT CAACCTGATT TCAAAACAAT TTTAGAGAGC CCAACTGATA
   491 AAAAAGTAGG CTGGAAAGTG ATATTTAACA ATATGGTGAA TCAAAATTGG GGACCATACG ATCGAGATTC
   561 TTGGAACCCG GTATATGGCA ATCAACTTTT CATGAAAACT AGAAATGGTT CTATGAAAGC AGCAGATAAC
   631 TTCCTTGATC CTAACAAAGC AAGTTCTCTA TTATCTTCAG GGTTTTCACC AGACTTCGCT ACAGTTATTA
   701 CTATGGATAG AAAAGCATCC AAACAACAAA CAAATATAGA TGTAATATAC GAACGAGTTC GTGATGATTA
   771 CCAATTGCAT TGGACTTCAA CAAATTGGAA AGGTACCAAT ACTAAAGATA AATGGACAGA TCGTTCTTCA
   841 GAAAGATATA AAATCGATTG GGAAAAAGAA GAAATGACAA AT

SEQ ID NO: 2
(WT α-HL)

1 ADSDINIKTG TTDIGSNTTV KTGDLVTYDK ENGMHKKVFY SFIDDKNHNK KLLVIRTKGT IAGQYRVYSE
    71 EGANKSGLAW PSAFKVQLQL PDNEVAQISD YYPRNSIDTK EYMSTLTYGF NGNVTGDDTG KIGGLIGANV
   141 SIGHTLKYVQ PDFKTILESP TDKKVGWKVI FNNMVNQNWG PYDRDSWNPV YGNQLFMKTR NGSMKAADNF
   211 LDPNKASSLL SSGFSPDFAT VITMDRKASK QQTNIDVIYE RVRDDYQLHW TSTNWKGTNT KDKWTDRSSE
   281 RYKIDWEKEE MTN
```

Sequence listing

SEQ ID NO: 3

(α-HL E111N/K147N)

```
  1 ATGGCAGATT CTGATATTAA TATTAAAACC GGTACTACAG ATATTGGAAG CAATACTACA GTAAAAACAG
 71 GTGATTTAGT CACTTATGAT AAAGAAAATG GCATGCACAA AAAAGTATTT TATAGTTTTA TCGATGATAA
141 AAATCACAAT AAAAAACTGC TAGTTATTAG AACAAAAGGT ACCATTGCTG GTCAATATAG AGTTTATAGC
211 GAAGAAGGTG CTAACAAAAG TGGTTTAGCC TGGCCTTCAG CCTTTAAGGT ACAGTTGCAA CTACCTGATA
281 ATGAAGTAGC TCAAATATCT GATTACTATC CAAGAAATTC GATTGATACA AAAAACTATA TGAGTACTTT
351 AACTTATGGA TTCAACGGTA ATGTTACTGG TGATGATACA GGAAAAATTG GCGGCCTTAT TGGTGCAAAT
421 GTTTCGATTG GTCATACACT GAACTATGTT CAACCTGATT TCAAACAAT TTTAGAGAGC CCAACTGATA
491 AAAAAGTAGG CTGGAAAGTG ATATTTAACA ATATGGTGAA TCAAAATTGG GGACCATACG ATCGAGATTC
561 TTGGAACCCG GTATATGGCA ATCAACTTTT CATGAAAACT AGAAATGGTT CTATGAAAGC AGCAGATAAC
631 TTCCTTGATC CTAACAAAGC AAGTTCTCTA TTATCTTCAG GGTTTTCACC AGACTTCGCT ACAGTTATTA
701 CTATGGATAG AAAAGCATCC AAACAACAAA CAAATATAGA TGTAATATAC GAACGAGTTC GTGATGATTA
771 CCAATTGCAT TGGACTTCAA CAAATTGGAA AGGTACCAAT ACTAAGATA AATGGACAGA TCGTTCTTCA
841 GAAAGATATA AATCGATTG GGAAAAAGAA GAAATGACAA AT
```

SEQ ID NO: 4

(α-HL E111N/K147N)

```
  1 ADSDINIKTG TTDIGSNTTV KTGDLVTYDK ENGMHKKVFY SFIDDKNHNK KLLVIRTKGT IAGQYRVYSE
 71 EGANKSGLAW PSAFKVQLQL PDNEVAQISD YYPRNSIDTK NYMSTLTYGF NGNVTGDDTG KIGGLIGANV
141 SIGHTLNYVQ PDFKTILESP TDKKVGWKVI FNNMVNQNWG PYDRDSWNPV YGNQLFMKTR NGSMKAADNF
211 LDPNKASSLL SSGFSPDFAT VITMDRKASK QQTNIDVIYE RVRDDYQLHW TSTNWKGTNT KDKWTDRSSE
281 RYKIDWEKEE MTN
```

SEQ ID NO: 5

(WT EcoExo I)

```
   1 ATGATGAACG ATGGCAAACA GCAGAGCACC TTCCTGTTTC ATGATTATGA AACCTTCGGT ACCCATCCGG
  71 CCCTGGATCG TCCGGCGCAG TTTGCGGCCA TTCGCACCGA TAGCGAATTC AATGTGATTG GCGAACCGGA
 141 AGTGTTTTAT TGCAAACCGG CCGATGATTA TCTGCCGCAG CCGGGTGCGG TGCTGATTAC CGGTATTACC
 211 CCGCAGGAAG CGCGCGCGAA AGGTGAAAAC GAAGCGGCGT TTGCCGCGCG CATTCATAGC CTGTTTACCG
 281 TGCCGAAAAC CTGCATTCTG GGCTATAACA ATGTGCGCTT CGATGATGAA GTTACCCGTA ATATCTTTTA
 351 TCGTAACTTT TATGATCCGT ATGCGTGGAG CTGGCAGCAT GATAACAGCC GTTGGGATCT GCTGGATGTG
 421 ATGCGCGCGT GCTATGCGCT GCGCCCGGAA GGCATTAATT GGCCGGAAAA CGATGATGGC CTGCCGAGCT
 491 TTCGTCTGGA ACATCTGACC AAAGCCAACG GCATTGAACA TAGCAATGCC CATGATGCGA TGGCCGATGT
 561 TTATGCGACC ATTGCGATGG CGAAACTGGT TAAAACCCGT CAGCCGCGCC TGTTTGATTA TCTGTTTACC
 631 CACCGTAACA ACACAAACT GATGGCGCTG ATTGATGTTC CGCAGATGAA ACCGCTGGTG CATGTGAGCG
 701 GCATGTTTGG CGCCTGGCGC GGCAACACCA GCTGGGTGGC CCCGCTGGCC TGGCACCCGG AAAATCGTAA
 771 CGCCGTGATT ATGGTTGATC TGGCCGGTGA TATTAGCCTG CTGCTGGAAC TGGATAGCGA TACCCTGCGT
 841 GAACGCCTGT ATACCGCCAA AACCGATCTG GGCGATAATG CCGCCGTGCC GGTGAAACTG GTTCACATTA
 911 ACAAATGCCC GGTGCTGGCC CAGGCGAACA CCCTGCGCCC GGAAGATGCG GATCGTCTGG GTATTAATCG
 981 CCAGCATTGT CTGGATAATC TGAAAATCCT GCGTGAAAAC CCGCAGGTGC GTGAAAAAGT GGTGGCGATC
1051 TTCGCGGAAG CGGAACCGTT CACCCCGAGC GATAACGTGG ATGCGCAGCT GTATAACGGC TTCTTTAGCG
1121 ATGCCGATCG CGCGGCGATG AAAATCGTTC TGGAAACCGA ACCGCGCAAT CTGCCGGCGC TGGATATTAC
1191 CTTTGTTGAT AAACGTATTG AAAAACTGCT GTTTAATTAT CGTGCGCGCA ATTTTCCGGG TACCCTGGAT
1261 TATGCCGAAC AGCAGCGTTG GCTGGAACAT CGTCGTCAGG TTTTCACCCC GGAATTTCTG CAGGGTTATG
1331 CGGATGAACT GCAGATGCTG GTTCAGCAGT ATGCCGATGA TAAAGAAAAA GTGGCGCTGC
```

SEQ ID NO: 6

(WT EcoExo I)

```
  1 MNDGKQQST FLFHDYETFG THPALDRPAQ FAAIRTDSEF NVIGEPEVFY
 51 CKPADDYLPQ PGAVLITGIT PQEARAKGEN EAAFAARIHS LFTVPKTCIL
101 GYNNVRFDDE VTRNIFYRNF YDPYAWSWQH DNSRWDLLDV MRACYALRPE
151 GINWPENDDG LPSFRLEHLT KANGIEHSNA HDAMADVYAT IAMAKLVKTR
201 QPRLFDYLFT HRNKHKLMAL IDVPQMKPLV HVSGMFGAWR GNTSWVAPLA
251 WHPENRNAVI MVDLAGDISP LLELDSDTLR ERLYTAKTDL GDNAAVPVKL
301 VHINKCPVLA QANTLRPEDA DRLGINRQHC LDNLKILREN PQVREKVVAI
351 FAEAEPFTPS DNVDAQLYNG FFSDADRAAM KIVLETEPRN LPALDITFVD
401 KRIEKLLFNY RARNFPGTLD YAEQQRWLEH RRQVFTPEFL QGYADELQML
451 VQQYADDKEK VALLKALWQY AEEIV SGSGH HHHHH
```

SEQ ID NO: 7

(WT Exo III)

```
  1 ATGAAATTTG TCTCTTTTAA TATCAACGGC CTGCGCGCCA GACCTCACCA GCTTGAAGCC ATCGTCGAAA
 71 AGCACCAACC GGATGTGATT GGCCTGCAGG AGACAAAAGT TCATGACGAT ATGTTTCCGC TCGAAGAGGT
141 GGCGAAGCTC GGCTACAACG TGTTTTATCA CGGGCAGAAA GGCCATTATG GCGTGGCGCT GCTGACCAAA
211 GAGACGCCGA TTGCCGTGCG TCGCGGCTTT CCCGGTGACG ACGAAGAGGC GCAGCGGCGG ATTATTATGG
281 CGGAAATCCC CTCACTGCTG GGTAATGTCA CCGTGATCAA CGGTTACTTC CCGCAGGGTG AAAGCCGCGA
351 CCATCCGATA AAATTCCCGG CAAAAGCGCA GTTTTATCAG AATCTGCAAA ACTACCTGGA AACCGAACTC
421 AAACGTGATA ATCCGGTACT GATTATGGGC GATATGAATA TCAGCCCTAC AGATCTGGAT ATCGGCATTG
491 GCGAAGAAAA CCGTAAGCGC TGGCTGCGTA CCGGTAAATG CTCTTTCCTG CCGGAAGAGC GCGAATGGAT
```

```
561 GGACAGGCTG ATGAGCTGGG GGTTGGTCGA TACCTTCCGC CATGCGAATC CGCAAACAGC AGATCGTTTC
631 TCATGGTTTG ATTACCGCTC AAAAGGTTTT GACGATAACC GTGGTCTGCG CATCGACCTG CTGCTCGCCA
701 GCCAACCGCT GGCAGAATGT TGCGTAGAAA CCGGCATCGA CTATGAAATC CGCAGCATGG AAAAACCGTC
771 CGATCACGCC CCCGTCTGGG CGACCTTCCG CCGC
```

SEQ ID NO: 8

(WT Exo III)

```
  1 MKFVSFNING LRARPHQLEA IVEKHQPDVI GLQETKVHDD MFPLEEVAKL GYNVFYHGQK GHYGVALLTK
 71 ETPIAVRRGF PGDDEEAQRR IIMAEIPSLL GNVTVINGYF PQGESRDHPI KFPAKAQFYQ NLQNYLETEL
141 KRDNPVLIMG DMNISPTDLD IGIGEENRKR WLRTGKCSFL PEEREWMDRL MSWGLVDTFR HANPQTADRF
211 SWFDYRSKGF DDNRGLRIDL LLASQPLAEC CVETGIDYEI RSMEKPSDHA PVWATFRR
```

SEQ ID NO: 9

(WT RecJ)

```
   1 ATGTTTCGTC GTAAAGAAGA TCTGGATCCG CCGCTGGCAC TGCTGCCGCT GAAAGGCCTG CGCGAAGCCG
  71 CCGCACTGCT GGAAGAAGCG CTGCGTCAAG GTAAACGCAT TCGTGTTCAC GGCGACTATG ATGCGGATGG
 141 CCTGACCGGC ACCGCGATCC TGGTTCGTGG TCTGGCCGCC CTGGGTGCGG ATGTTCATCC GTTTATCCCG
 211 CACCGCCTGG AAGAAGGCTA TGGTGTCCTG ATGGAACGCG TCCCGGAACA TCTGGAAGCC TCGGACCTGT
 281 TTCTGACCGT TGACTGCGGC ATTACCAACC ATGCGGAACT GCGCGAACTG CTGGAAAATG GCGTGGAAGT
 351 CATTGTTACC GATCATCATA CGCCGGGCAA AACGCCGCCG CCGGGTCTGG TCGTGCATCC GGCGCTGACG
 421 CCGGATCTGA AGAAAAACC GACCGGCGCA GGCGTGGCGT TTCTGCTGCT GTGGGCACTG CATGAACGCC
 491 TGGGCCTGCC GCCGCCGCTG GAATACGCGG ACCTGGCCGC CGTTGGCACC ATTGCCGACG TTGCCCCGCT
 561 GTGGGGTTGG AATCGTGCAC TGGTGAAAGA AGGTCTGGCA CGCATCCCGG CTTCATCTTG GGTGGGCCTG
 631 CGTCTGCTGG CTGAAGCCGT GGGCTATACC GGCAAAGCGG TCGAAGTCGC TTTCCGCATC GCGCCGCGCA
 701 TCAATGCGGC TTCCCGCCTG GGCGAAGCGG AAAAAGCCCT GCGCCTGCTG CTGACGGATG ATGCGGCAGA
 771 AGCTCAGGCG CTGGTCGGCG AACTGCACCG TCTGAACGCC CGTCGTCAGA CCCTGGAAGA AGCGATGCTG
 841 CGCAAACTGC TGCCGCAGGC CGACCCGGAA GCGAAAGCCA TCGTTCTGCT GGACCCGGAA GGCCATCCGG
 911 GTGTTATGGG TATTGTGGCC TCTCGCATCC TGGAAGCGAC CCTGCGCCCG GTCTTTCTGG TGGCCCAGGG
 981 CAAAGGCACC GTGCGTTCGC TGGCTCCGAT TTCCGCCGTC GAAGCACTGC GCAGCGCGGA AGATCTGCTG
1051 CTGCGTTATG GTGGTCATAA AGAAGCGGCG GGTTTCGCAA TGGATGAAGC GCTGTTTCCG GCGTTCAAAG
1121 CACGCGTTGA AGCGTATGCC GCACGTTTCC CGGATCCGGT TCGTGAAGTG GCACTGCTGG ATCTGCTGCC
1191 GGAACCGGGC CTGCTGCCGC AGGTGTTCCG TGAACTGGCA CTGCTGGAAC CGTATGGTGA AGGTAACCCG
1261 GAACCGCTGT TCCTG
```

SEQ ID NO: 10

(WT RecJ)

```
  1 MFRRKEDLDP PLALLPLKGL REAAALLEEA LRQGKRIRVH GDYDADGLTG TAILVRGLAA LGADVHPFIP
 71 HRLEEGYGVL MERVPEHLEA SDLFLTVDCG ITNHAELREL LENGVEVIVT DHHTPGKTPP PGLVVHPALT
141 PDLKEKPTGA GVAFLLLWAL HERLGLPPPL EYADLAAVGT IADVAPLWGW NRALVKEGLA RIPASSWVGL
211 RLLAEAVGYT GKAVEVAFRI APRINAASRL GEAEKALRLL LTDDAAEAQA LVGELHRLNA RRQTLEEAML
281 RKLLPQADPE AKAIVLLDPE GHPGVMGIVA SRILEATLRP VFLVAQGKGT VRSLAPISAV EALRSAEDLL
351 LRYGGHKEAA GFAMDEALFP AFKARVEAYA ARFPDPVREV ALLDLLPEPG LLPQVFRELA LLEPYGEGNP
421 EPLFL
```

SEQ ID NO: 11

(WT lambda Exo)

```
  1 TCCGGAAGCG GCTCTGGTAG TGGTTCTGGC ATGACACCGG ACATTATCCT GCAGCGTACC GGGATCGATG
 71 TGAGAGCTGT CGAACAGGGG GATGATGCGT GGCACAAATT ACGGCTCGGC GTCATCACCG CTTCAGAAGT
141 TCACAACGTG ATAGCAAAAC CCCGCTCCGG AAAGAAGTGG CCTGACATGA AAATGTCCTA CTTCCACACC
211 CTGCTTGCTG AGGTTTGCAC CGGTGTGGCT CCGGAAGTTA ACGCTAAAGC ACTGGCCTGG GGAAAACAGT
281 ACGAGAACGA CGCCAGAACC CTGTTTGAAT TCACTTCCGG CGTGAATGTT ACTGAATCCC CGATCATCTA
351 TCGCGACGAA AGTATGCGTA CCGCCTGCTC TCCCGATGGT TTATGCAGTG ACGGCAACGG CCTTGAACTG
421 AAATGCCCGT TTACCTCCCG GGATTTCATG AAGTTCCGGC TCGGTGGTTT CGAGGCCATA AGTCAGCTT
491 ACATGGCCCA GGTGCAGTAC AGCATGTGGG TGACGCGAAA AAATGCCTGG TACTTTGCCA ACTATGACCC
561 GCGTATGAAG CGTGAAGGCC TGCATTATGT CGTGATTGAG CGGGATGAAA AGTACATGGC GAGTTTTGAC
631 GAGATCGTGC CGGAGTTCAT CGAAAAAATG GACGAGGCAC TGGCTGAAAT TGGTTTTGTA TTTCCCCAGC
701 AATGGCGATC TGGCTCTGGT TCCGGCAGCG GTTCCGGA
```

SEQ ID NO: 12

(WT lambda Exo)

```
  1 MTPDIILQRT GIDVRAVEQG DDAWHKLRLG VITASEVHNV IAKPRSGKKW PDMKMSYFHT LLAEVCTGVA
 71 PEVNAKALAW GKQYENDART LFEFTSGVNV TESPIIYRDE SMRTACSPDG LCSDGNGLEL KCPFTSRDFM
141 KFRLGGFEAI KSAYMAQVQY SMWVTRKNAW YFANYDPRMK REGLHYVVIE RDEKYMASFD EIVPEFIEKM
211 DEALAEIGFV FGEQWR
```

SEQ ID NO: 13

CCCCCCCCCCCCCCCCCCCCCCCCCCCCCCCCCCCCCCCCCCCCCCCCCC

SEQ ID NO: 14

AAAAAAAAAAAAAAAAAAAAAAAAAAAAAAAAAAAAAAAAAAAAAAAAAA

-continued

| Sequence listing | |
|---|---|
| cccccccccccccccccccccccccccccccccccccc | SEQ ID NO: 15 |
| cccccccccccccccccccccccccccccccccAAAAA | SEQ ID NO: 16 |
| ccccccccccccccccccccccccccccccAAAAACCCC | SEQ ID NO: 17 |
| ccccccccccccccccccccccccccAAAAACCCCCCCCC | SEQ ID NO: 18 |
| ccccccccccccccccccccAAAAACCCCCCCCCCCCC | SEQ ID NO: 19 |
| ccccccccccccccAAAAACCCCCCCCCCCCCCCCCC | SEQ ID NO: 20 |
| ccccccccccccccccccccccccccccccccACCCCCC | SEQ ID NO: 21 |
| cccccccccccccccccccccccccccccccACCCCCCC | SEQ ID NO: 22 |
| ccccccccccccccccccccccccccccccACCCCCCCC | SEQ ID NO: 23 |
| cccccccccccccccccccccccccccccACCCCCCCCC | SEQ ID NO: 24 |
| ccccccccccccccccccccccccccccACCCCCCCCCC | SEQ ID NO: 25 |
| cccccccccccccccccccccccccccACCCCCCCCCCC | SEQ ID NO: 26 |
| ccccccccccccccccccccccccccACCCCCCCCCCCC | SEQ ID NO: 27 |
| cccccccccccccccccccccccccACCCCCCCCCCCCC | SEQ ID NO: 28 |
| ccccccccccccccccccccccccACCCCCCCCCCCCCC | SEQ ID NO: 29 |
| cccccccccccccccccccccccACCCCCCCCCCCCCCC | SEQ ID NO: 30 |
| ccccccccccccccccccccccACCCCCCCCCCCCCCCC | SEQ ID NO: 31 |
| cccccccccccccccccccccACCCCCCCCCCCCCCCCC | SEQ ID NO: 32 |
| ccccccccccccccccccccACCCCCCCCCCCCCCCCCC | SEQ ID NO: 33 |
| cccccccccccccccccccACCCCCCCCCCCCCCCCCCC | SEQ ID NO: 34 |
| ccccccccccccccccccccccccccccccccGCCCCCCC | SEQ ID NO: 35 |
| cccccccccccccccccccccccccccccccACCCCCCC | SEQ ID NO: 36 |
| ccccccccccccccccccccccccccccccccTCCCCCCC | SEQ ID NO: 37 |
| cccccccccccccccccccccccccccccccccCCCCCCC | SEQ ID NO: 38 |
| ccccccccccccccccccccccccccccccccGCCCCCCC | SEQ ID NO: 39 |
| ccccccccccccccccccccccccccccccACCCCCCCCC | SEQ ID NO: 40 |

| Sequence listing | |
|---|---|
| CCCCCCCCCCCCCCCCCCCCCCCCCTCCCCCCCCCCCC | SEQ ID NO: 41 |
| CCCCCCCCCCCCCCCCCCCCCCCCCCCCCCCCCCCCCC | SEQ ID NO: 42 |
| CCCCCCCCCCCCCCCCCCCCCCCGCCCCCCCCCCCCCC | SEQ ID NO: 43 |
| CCCCCCCCCCCCCCCCCCCCCCACCCCCCCCCCCCCCC | SEQ ID NO: 44 |
| CCCCCCCCCCCCCCCCCCCCCCCTCCCCCCCCCCCCCC | SEQ ID NO: 45 |
| CCCCCCCCCCCCCCCCCCCCCCCCCCCCCCCCCCCCCC | SEQ ID NO: 46 |
| ACTACCTAGTTTACGTAATCCATCTGAACAATGCAGCATT | SEQ ID NO: 47 |
| ACTACCTAGTTTACGTAATCCATCTGTACAATGCAGCATT | SEQ ID NO: 48 |
| ACTACCTAGTTTACGTAATCCATCTGGACAATGCAGCATT | SEQ ID NO: 49 |
| ACTACCTAGTTTACGTAATCCATCTGCACAATGCAGCATT | SEQ ID NO: 50 |
| CCCCCCCCCCCCCCCCCCCCCCCCCCCCCCCCCCCCCCB | SEQ ID NO: 51 |
| CCCCCCCCCCCCCCCCCCCCCCCCCCCTCCCCCCCCCCB | SEQ ID NO: 52 |
| CCCCCCCCCCCCCCCCCCCCCCCCCCACCCCCCCCCCCB | SEQ ID NO: 53 |
| CCCCCCCCCCCCCCCCCCCCCCCCCCGCCCCCCCCCCCB | SEQ ID NO: 54 |
| CCCCCCCCCCCCCCCCCCCCCCCCCCCCCTCCCCCCCCB | SEQ ID NO: 55 |
| CCCCCCCCCCCCCCCCCCCCCCCCCCCCACCCCCCCCB | SEQ ID NO: 56 |
| CCCCCCCCCCCCCCCCCCCCCCCCCCCCGCCCCCCCCB | SEQ ID NO: 57 |
| CCCCCCCCCCCCCCCCCCCCCCCCCCCACCCCTCCCCCCCCB | SEQ ID NO: 58 |
| CCCCCCCCCCCCCCCCCCCCCCCCCCCACCCCACCCCCCCCB | SEQ ID NO: 59 |
| CCCCCCCCCCCCCCCCCCCCCCCCCCCACCCCGCCCCCCCCB | SEQ ID NO: 60 |
| CCCCCCCCCCCCCCCCCCCCCCCCCCCGCCCCTCCCCCCCCB | SEQ ID NO: 61 |
| CCCCCCCCCCCCCCCCCCCCCCCCCCCGCCCCACCCCCCCCB | SEQ ID NO: 62 |
| CCCCCCCCCCCCCCCCCCCCCCCCCCCGCCCCGCCCCCCCCB | SEQ ID NO: 63 |

| Sequence listing | |
|---|---|
| CCCCCCCCCCCCCCCCCCCCCCCCCCTCCCCTCCCCCCCCB | SEQ ID NO: 64 |
| CCCCCCCCCCCCCCCCCCCCCCCCCCTCCCCACCCCCCCCB | SEQ ID NO: 65 |
| CCCCCCCCCCCCCCCCCCCCCCCCCCTCCCCGCCCCCCCCB | SEQ ID NO: 66 |

The invention claimed is:

1. A method for sequencing a heteropolymeric target nucleic acid sequence, comprising:
   (a) passing the heteropolymeric target nucleic acid sequence through a transmembrane protein pore so that the nucleotides in the heteropolymeric target nucleic acid sequence interact with two or more distinct sites of amino acids within the sequence of the transmembrane protein pore that are capable of discriminating between different nucleotides, such that the overall current passing through the pore is influenced by the interactions between each of the two or more sites and the nucleotides located at each of the sites;
   wherein: (1) the pore has been determined to comprise at least two of said distinct sites of amino acids, (2) at least one of the distinct site of amino acids is modified by amino acid substitution to alter its ability to discriminate between different nucleotides, and (3) the heteropolymeric target nucleic acid sequence is not cleaved or digested to form individual nucleotides before the heteropolymeric target nucleic acid sequence is sequenced; and
   (b) measuring the overall current passing through the pore, thereby determining the sequence of the heteropolymeric target nucleic acid sequence.

2. A method according to claim 1, wherein;
   (a) the two or more distinct sites each discriminate between different nucleotides in a different manner;
   (b) the interaction of a selected nucleotide with each of the two or more distinct sites results in a different current passing through the transmembrane protein pore; or
   (c) the interaction of different nucleotides with each of the two or more distinct sites results in differing currents passing through the transmembrane protein pore, wherein the separation between the mean values of the differing currents differs between each of the two or more distinct sites.

3. A method according to claim 1, wherein the transmembrane protein pore is modified to alter the current flowing through the transmembrane protein pore when a selected nucleotide interacts with the two or more distinct sites.

4. A method according to claim 1, wherein;
   (a) the heteropolymeric target nucleic acid sequence comprises three or more different nucleotides;
   (b) the heteropolymeric target nucleic acid sequence comprises four different nucleotides; or;
   (c) the heteropolymeric target nucleic acid sequence comprises four different nucleotides and the four different nucleotides comprise the nucleobases (a) adenine, (b) guanine, (c) thymine or uracil and (d) cytosine.

5. A method according to claim 1, wherein the heteropolymeric target nucleic acid sequence is passed through the transmembrane protein pore using a nucleic acid handling enzyme.

6. A method according to claim 5, wherein;
   (a) the nucleic acid handling enzyme is derived from a nuclease;
   (b) the nucleic acid handling enzyme is derived from a nuclease, wherein the nuclease is a member of any one of the Enzyme Classification groups 3.1.11, 3.1.13, 3.1.14, 3.1.15, 3.1.16, 3.1.21, 3.1.22, 3.1.25, 3.1.26, 3.1.27, 3.1.30 or 3.1.31;
   (c) the nucleic acid handling enzyme is derived from an exonuclease;
   (d) the nucleic acid handling enzyme is derived from an exonuclease, wherein the exonuclease comprises a sequence set forth in any one of SEQ ID NOs: 6, 8, 10 and 12, or a variant thereof;
   (e) the nucleic acid handling enzyme is derived from a polymerase or helicase;
   (f) the nucleic acid handling enzyme is derived from a polymerase or helicase and
      (i) the polymerase is member of any one of the Enzyme Classification groups 2.7.7.6, 2.7.7.7, 2.7.7.19, 2.7.7.48 or 2.7.7.49; or
      (ii) the helicase is member of any one of the Enzyme Classification groups 3.6.1. or 2.7.7.;
   (g) the nucleic acid handling enzyme is derived from a polymerase, wherein the polymerase is a DNA-dependent DNA polymerase, RNA-dependent DNA polymerase, DNA-dependent RNA polymerase, or RNA-dependent RNA polymerase; or
   (h) the helicase is an ATP-dependent DNA helicase, ATP-dependent RNA helicase, or ATP-independent RNA helicase.

7. A method according to claim 1, wherein;
   (a) the transmembrane protein pore is derived from α-hemolysin;
   (b) the transmembrane protein pore is derived from α-hemolysin and comprises seven subunits comprising the sequence set forth in SEQ ID NO: 2 or a variant thereof; or
   (c) the transmembrane protein pore is derived from α-hemolysin, comprises the sequence set forth in SEQ ID NO: 2 or a variant thereof, and all seven subunits have an asparagine at position 111 of SEQ ID NO: 2 and an asparagine at position 147 of SEQ ID NO: 2.

8. The method according to claim 1, wherein the pore does not contain a covalently linked exogenous moiety that facilitates an interaction between the pore and nucleotides.

9. A method for sequencing a heteropolymeric target nucleic acid sequence, comprising:
   (a) passing the heteropolymeric target nucleic acid sequence through a transmembrane protein pore so that the nucleotides in the heteropolymeric target nucleic acid sequence interact with two or more distinct sites of amino acids within the sequence of the pore that are capable of discriminating between different nucleotides, such that the overall current passing through the pore is influenced by the interactions between each of the two or more sites and the nucleotides located at each of the sites;

wherein: (1) at least two of the distinct sites of amino acids are modified by amino acid substitution to alter their ability to discriminate between different nucleotides, (2) the pore does not contain a covalently linked exogenous moiety that facilitates an interaction between the pore and nucleotides, and (3) the heteropolymeric target nucleic acid sequence is not cleaved or digested to form individual nucleotides before the heteropolymeric target nucleic acid sequence is sequenced; and (b) measuring the overall current passing through the pore, thereby determining the sequence of the heteropolymeric target nucleic acid sequence.

10. A method according to claim 9, wherein;
(a) the two or more distinct sites each discriminate between different nucleotides in a different manner;
(b) the interaction of a selected nucleotide with each of the two or more distinct sites results in a different current passing through the transmembrane protein pore; or
(c) the interaction of different nucleotides with each of the two or more distinct sites results in differing currents passing through the transmembrane protein pore, wherein the separation between the mean values of the differing currents differs between each of the two or more distinct sites.

11. A method according to claim 9, wherein the transmembrane protein pore is modified to alter the current flowing through the transmembrane protein pore when a selected nucleotide interacts with the two or more distinct sites.

12. A method according to claim 9, wherein;
(a) the heteropolymeric target nucleic acid sequence comprises three or more different nucleotides;
(b) the heteropolymeric target nucleic acid sequence comprises four different nucleotides; or;
(c) the heteropolymeric target nucleic acid sequence comprises four different nucleotides and the four different nucleotides comprise the nucleobases (a) adenine, (b) guanine, (c) thymine or uracil and (d) cytosine.

13. A method according to claim 9, wherein the heteropolymeric target nucleic acid sequence is passed through the transmembrane protein pore using a nucleic acid handling enzyme.

14. A method according to claim 13, wherein;
(a) the nucleic acid handling enzyme is derived from a nuclease;
(b) the nucleic acid handling enzyme is derived from a nuclease, wherein the nuclease is a member of any one of the Enzyme Classification groups 3.1.11, 3.1.13, 3.1.14, 3.1.15, 3.1.16, 3.1.21, 3.1.22, 3.1.25, 3.1.26, 3.1.27, 3.1.30 or 3.1.31;
(c) the nucleic acid handling enzyme is derived from an exonuclease;
(d) the nucleic acid handling enzyme is derived from an exonuclease, wherein the exonuclease comprises a sequence set forth in any one of SEQ ID NOs: 6, 8, 10 and 12, or a variant thereof;
(e) the nucleic acid handling enzyme is derived from a polymerase or helicase;
(f) the nucleic acid handling enzyme is derived from a polymerase or helicase and
  (i) the polymerase is member of any one of the Enzyme Classification groups 2.7.7.6, 2.7.7.7, 2.7.7.19, 2.7.7.48 or 2.7.7.49; or
  (ii) the helicase is member of any one of the Enzyme Classification groups 3.6.1. or 2.7.7.;
(g) the nucleic acid handling enzyme is derived from a polymerase, wherein the polymerase is a DNA-dependent DNA polymerase, RNA-dependent DNA polymerase, DNA-dependent RNA polymerase, or RNA-dependent RNA polymerase; or
(h) the helicase is an ATP-dependent DNA helicase, ATP-dependent RNA helicase, or ATP-independent RNA helicase.

15. A method according to claim 9, wherein;
(a) the transmembrane protein pore is derived from α-hemolysin;
(b) the transmembrane protein pore is derived from α-hemolysin and comprises seven subunits comprising the sequence set forth in SEQ ID NO: 2 or a variant thereof; or
(c) the transmembrane protein pore is derived from α-hemolysin, comprises the sequence set forth in SEQ ID NO: 2 or a variant thereof, and all seven subunits have an asparagine at position 111 of SEQ ID NO: 2 and an asparagine at position 147 of SEQ ID NO: 2.

* * * * *

SEQUENCE LISTING

<160> NUMBER OF SEQ ID NOS: 66

<210> SEQ ID NO 1
<211> LENGTH: 882
<212> TYPE: DNA
<213> ORGANISM: Staphylococcus aureus

<400> SEQUENCE: 1

```
atggcagatt ctgatattaa tattaaaacc ggtactacag atattggaag caatactaca      60
gtaaaaacag gtgatttagt cacttatgat aaagaaaatg gcatgcacaa aaaagtattt     120
tatagttta tcgatgataa aaatcacaat aaaaaactgc tagttattag aacaaaaggt     180
accattgctg gtcaatatag agtttatagc gaagaaggtg ctaacaaaag tggtttagcc     240
tggccttcag cctttaaggt acagttgcaa ctacctgata tgaagtagc tcaaatatct     300
gattactatc caagaaattc gattgataca aaagagtata tgagtacttt aacttatgga     360
ttcaacggta atgttactgg tgatgataca ggaaaaattg gcggcttat tggtgcaaat     420
gtttcgattg gtcatacact gaaatatgtt caacctgatt tcaaaacaat tttagagagc     480
ccaactgata aaaagtagg ctggaaagtg atatttaaca atatggtgaa tcaaaattgg     540
ggaccatacg atcgagattc ttggaacccg gtatatggca atcaacttt catgaaaact     600
agaaatggtt ctatgaaagc agcagataac ttccttgatc ctaacaaagc aagttctcta     660
ttatcttcag ggttttcacc agacttcgct acagttatta ctatggatag aaaagcatcc     720
aaacaacaaa caaatataga gtaatatac gaacgagttc gtgatgatta ccaattgcat     780
tggacttcaa caaattggaa aggtaccaat actaaagata aatggacaga tcgttcttca     840
gaaagatata aatcgattg ggaaaaagaa gaaatgacaa at                        882
```

<210> SEQ ID NO 2
<211> LENGTH: 293
<212> TYPE: PRT
<213> ORGANISM: Staphylococcus aureus

<400> SEQUENCE: 2

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80
```

```
Pro Ser Ala Phe Lys Val Gln Leu Gln Leu Pro Asp Asn Glu Val Ala
            85                  90                  95

Gln Ile Ser Asp Tyr Tyr Pro Arg Asn Ser Ile Asp Thr Lys Glu Tyr
        100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
        130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
        210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

<210> SEQ ID NO 3
<211> LENGTH: 882
<212> TYPE: DNA
<213> ORGANISM: Artificial sequence
<220> FEATURE:
<223> OTHER INFORMATION: a-HL E111N/K147N

<400> SEQUENCE: 3
atggcagatt ctgatattaa tattaaaacc ggtactacag atattggaag caatactaca      60
gtaaaaacag gtgatttagt cacttatgat aaagaaaatg gcatgcacaa aaaagtattt     120
tatagtttta tcgatgataa aaatcacaat aaaaaactgc tagttattag aacaaaaggt     180
accattgctg gtcaatatag agtttatagc gaagaaggtg ctaacaaaag tggtttagcc     240
tggccttcag cctttaaggt acagttgcaa ctacctgata tgaagtagc tcaaatatct      300 gattactatc caagaaattc gattgataca aaaaactata tgagtacttt aacttatgga     360
ttcaacggta atgttactgg tgatgataca ggaaaaattg gcggcttat tggtgcaaat      420 gtttcgattg gtcatacact gaactatgtt caacctgatt tcaaaacaat tttagagagc     480
ccaactgata aaaagtagg ctggaaagtg atatttaaca atatggtgaa tcaaaattgg      540
ggaccatacg atcgagattc ttggaacccg tatatggca atcaactttt catgaaaact      600
agaaatggtt ctatgaaagc agcagataac ttccttgatc ctaacaaagc aagttctcta     660
ttatcttcag ggttttcacc agacttcgct acagttatta ctatggatag aaaagcatcc     720
aaacaacaaa caatatagt gtaatatac gaacgagttc gtgatgatta ccaattgcat      780
tggacttcaa caaattggaa aggtaccaat actaaagata atggacaga tcgttcttca     840
```
gaaagatata aaatcgattg ggaaaaagaa gaaatgacaa at                     882

<210> SEQ ID NO 4
<211> LENGTH: 293
<212> TYPE: PRT
<213> ORGANISM: Artificial sequence
<220> FEATURE:
<223> OTHER INFORMATION: a-HL E111N/K147N

<400> SEQUENCE: 4

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290
```

<210> SEQ ID NO 5
<211> LENGTH: 1390
<212> TYPE: DNA
<213> ORGANISM: Escherichia coli

<400> SEQUENCE: 5
atgatgaacg atggcaaaca gcagagcacc ttcctgtttc atgattatga aaccttcggt    60

```
acccatccgg ccctggatcg tccggcgcag tttgcggcca ttcgcaccga tagcgaattc    120
aatgtgattg gcgaaccgga agtgtttat gcaaaccgg ccgatgatta tctgccgcag    180
```


```
acccatccgg ccctggatcg tccggcgcag tttgcggcca ttcgcaccga tagcgaattc    120
aatgtgattg gcgaaccgga agtgttttat gcaaaccgg ccgatgatta tctgccgcag    180
ccgggtgcgg tgctgattac cggtattacc ccgcaggaag cgcgcgcgaa aggtgaaaac    240
gaagcggcgt ttgccgcgcg cattcatagc ctgtttaccg tgccgaaaac ctgcattctg    300
ggctataaca atgtgcgctt cgatgatgaa gttacccgta atatctttta tcgtaacttt    360
tatgatccgt atgcgtggag ctggcagcat gataacagcc gttgggatct gctggatgtg    420
atgcgcgcgt gctatgcgct cgcccggaa ggcattaatt ggccggaaaa cgatgatggc    480
ctgccgagct ttcgtctgga acatctgacc aaagccaacg gcattgaaca tagcaatgcc    540
catgatgcga tggccgatgt ttatgcgacc attgcgatgg cgaaactggt taaaacccgt    600
cagccgcgcc tgtttgatta tctgtttacc caccgtaaca acacaaact gatggcgctg    660
attgatgttc cgcagatgaa accgctggtg catgtgagcg gcatgtttgg cgcctggcgc    720
ggcaacacca gctgggtggc cccgctggcc tggcacccgg aaaatcgtaa cgccgtgatt    780
atggttgatc tggccggtga tattagcccg ctgctggaac tggatagcga taccctgcgt    840
gaacgcctgt ataccgccaa aaccgatctg ggcgataatg ccgccgtgcc ggtgaaactg    900
gttcacatta acaaatgccc ggtgctggcc caggcgaaca ccctgcgccc ggaagatgcg    960
gatcgtctgg gtattaatcg ccagcattgt ctggataatc tgaaaatcct gcgtgaaaac    1020
ccgcaggtgc gtgaaaaagt ggtggcgatc ttcgcggaag cggaaccgtt caccccgagc    1080
gataacgtgg atgcgcagct gtataacggc ttctttagcg atgccgatcg cgcggcgatg    1140
aaaatcgttc tggaaaccga accgcgcaat ctgccggcgc tggatattac ctttgttgat    1200
aaacgtattg aaaaactgct gtttaattat cgtgcgcgca attttccggg taccctggat    1260
tatgccgaac agcagcgttg gctggaacat cgtcgtcagg ttttcacccc ggaatttctg    1320
cagggttatg cggatgaact gcagatgctg gttcagcagt atgccgatga taaagaaaaa    1380
gtggcgctgc                                                          1390
```

<210> SEQ ID NO 6
<211> LENGTH: 485
<212> TYPE: PRT
<213> ORGANISM: Escherichia coli

<400> SEQUENCE: 6

Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Cys Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Cys Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

```
Gln His Asp Asn Ser Arg Trp Asp Leu Leu Asp Val Met Arg Ala Cys
130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
            165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
            195                 200                 205

Phe Thr His Arg Asn Lys His Lys Leu Met Ala Leu Ile Asp Val Pro
210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
            245                 250                 255

Asn Ala Val Ile Met Val Asp Leu Ala Gly Asp Ile Ser Pro Leu Leu
            260                 265                 270

Glu Leu Asp Ser Asp Thr Leu Arg Glu Arg Leu Tyr Thr Ala Lys Thr
            275                 280                 285

Asp Leu Gly Asp Asn Ala Ala Val Pro Val Lys Leu Val His Ile Asn
290                 295                 300

Lys Cys Pro Val Leu Ala Gln Ala Asn Thr Leu Arg Pro Glu Asp Ala
305                 310                 315                 320

Asp Arg Leu Gly Ile Asn Arg Gln His Cys Leu Asp Asn Leu Lys Ile
            325                 330                 335

Leu Arg Glu Asn Pro Gln Val Arg Glu Lys Val Val Ala Ile Phe Ala
            340                 345                 350

Glu Ala Glu Pro Phe Thr Pro Ser Asp Asn Val Asp Ala Gln Leu Tyr
            355                 360                 365

Asn Gly Phe Phe Ser Asp Ala Asp Arg Ala Ala Met Lys Ile Val Leu
            370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
            405                 410                 415

Gly Thr Leu Asp Tyr Ala Glu Gln Gln Arg Trp Leu Glu His Arg Arg
            420                 425                 430

Gln Val Phe Thr Pro Glu Phe Leu Gln Gly Tyr Ala Asp Glu Leu Gln
            435                 440                 445

Met Leu Val Gln Gln Tyr Ala Asp Asp Lys Glu Lys Val Ala Leu Leu
450                 455                 460

Lys Ala Leu Trp Gln Tyr Ala Glu Glu Ile Val Ser Gly Ser Gly His
465                 470                 475                 480

His His His His His
            485

<210> SEQ ID NO 7
<211> LENGTH: 804
<212> TYPE: DNA
<213> ORGANISM: Escherichia coli

<400> SEQUENCE: 7
atgaaatttg tctcttttaa tatcaacggc ctgcgcgcca gacctcacca gcttgaagcc    60
```

```
atcgtcgaaa agcaccaacc ggatgtgatt ggcctgcagg agacaaaagt tcatgacgat      120
atgtttccgc tcgaagaggt ggcgaagctc ggctacaacg tgttttatca cgggcagaaa      180
ggccattatg gcgtggcgct gctgaccaaa gagacgccga ttgccgtgcg tcgcggcttt      240
cccggtgacg acgaagaggc gcagcggcgg attattatgg cggaaatccc ctcactgctg      300
ggtaatgtca ccgtgatcaa cggttacttc ccgcagggtg aaagccgcga ccatccgata      360
aaattcccgg caaaagcgca gttttatcag aatctgcaaa actacctgga aaccgaactc      420
aaacgtgata atccggtact gattatgggc gatatgaata tcagccctac agatctggat      480
atcggcattg gcgaagaaaa ccgtaagcgc tggctgcgta ccggtaaatg ctctttcctg      540
ccggaagagc gcgaatggat ggacaggctg atgagctggg ggttggtcga taccttccgc      600
catgcgaatc cgcaaacagc agatcgtttc tcatggtttg attaccgctc aaaaggtttt      660
gacgataacc gtggtctgcg catcgacctg ctgctcgcca gccaaccgct ggcagaatgt      720
tgcgtagaaa ccggcatcga ctatgaaatc gcagcatgg aaaaaccgtc cgatcacgcc      780
cccgtctggg cgaccttccg ccgc                                            804
```

<210> SEQ ID NO 8
<211> LENGTH: 268
<212> TYPE: PRT
<213> ORGANISM: Escherichia coli

<400> SEQUENCE: 8

```
Met Lys Phe Val Ser Phe Asn Ile Asn Gly Leu Arg Ala Arg Pro His
1               5                   10                  15

Gln Leu Glu Ala Ile Val Glu Lys His Gln Pro Asp Val Ile Gly Leu
            20                  25                  30

Gln Glu Thr Lys Val His Asp Asp Met Phe Pro Leu Glu Glu Val Ala
        35                  40                  45

Lys Leu Gly Tyr Asn Val Phe Tyr His Gly Gln Lys Gly His Tyr Gly
    50                  55                  60

Val Ala Leu Leu Thr Lys Glu Thr Pro Ile Ala Val Arg Arg Gly Phe
65                  70                  75                  80

Pro Gly Asp Asp Glu Glu Ala Gln Arg Arg Ile Ile Met Ala Glu Ile
                85                  90                  95

Pro Ser Leu Leu Gly Asn Val Thr Val Ile Asn Gly Tyr Phe Pro Gln
            100                 105                 110

Gly Glu Ser Arg Asp His Pro Ile Lys Phe Pro Ala Lys Ala Gln Phe
        115                 120                 125

Tyr Gln Asn Leu Gln Asn Tyr Leu Glu Thr Glu Leu Lys Arg Asp Asn
    130                 135                 140

Pro Val Leu Ile Met Gly Asp Met Asn Ile Ser Pro Thr Asp Leu Asp
145                 150                 155                 160

Ile Gly Ile Gly Glu Glu Asn Arg Lys Arg Trp Leu Arg Thr Gly Lys
                165                 170                 175

Cys Ser Phe Leu Pro Glu Glu Arg Glu Trp Met Asp Arg Leu Met Ser
            180                 185                 190

Trp Gly Leu Val Asp Thr Phe Arg His Ala Asn Pro Gln Thr Ala Asp
        195                 200                 205

Arg Phe Ser Trp Phe Asp Tyr Arg Ser Lys Gly Phe Asp Asp Asn Arg
    210                 215                 220

Gly Leu Arg Ile Asp Leu Leu Leu Ala Ser Gln Pro Leu Ala Glu Cys
225                 230                 235                 240
```

```
Cys Val Glu Thr Gly Ile Asp Tyr Glu Ile Arg Ser Met Glu Lys Pro
                245                 250                 255
Ser Asp His Ala Pro Val Trp Ala Thr Phe Arg Arg
            260                 265
```

<210> SEQ ID NO 9
<211> LENGTH: 1275
<212> TYPE: DNA
<213> ORGANISM: Thermus thermophilus

<400> SEQUENCE: 9

```
atgtttcgtc gtaaagaaga tctggatccg ccgctggcac tgctgccgct gaaaggcctg      60
cgcgaagccg ccgcactgct ggaagaagcg ctgcgtcaag gtaaacgcat tcgtgttcac     120
ggcgactatg atgcggatgg cctgaccggc accgcgatcc tggttcgtgg tctggccgcc     180
ctgggtgcgg atgttcatcc gtttatcccg caccgcctgg aagaaggcta tggtgtcctg     240
atggaacgcg tcccggaaca tctggaagcc tcggacctgt ttctgaccgt tgactgcggc     300
attaccaacc atgcggaact gcgcgaactg ctggaaaatg gcgtggaagt cattgttacc     360
gatcatcata cgccgggcaa aacgccgccg ccgggtctgg tcgtgcatcc ggcgctgacg     420
ccggatctga agaaaaaacc gaccggcgca ggcgtggcgt ttctgctgct gtgggcactg     480
catgaacgcc tgggcctgcc gccgccgctg aatacgcgg acctggcagc cgttggcacc     540
attgccgacg ttgccccgct gtggggttgg aatcgtgcac tggtgaaaga aggtctggca     600
cgcatcccgg cttcatcttg ggtgggcctg cgtctgctgg ctgaagccgt gggctatacc     660
ggcaaagcgg tcgaagtcgc tttccgcatc gcgccgcgca tcaatgcggc ttcccgcctg     720
ggcgaagcgg aaaaagccct gcgcctgctg ctgacggatg atgcggcaga agctcaggcg     780
ctggtcggcg aactgcaccg tctgaacgcc gtcgtcaga ccctggaaga agcgatgctg     840
cgcaaactgc tgccgcaggc cgaccccgaa gcgaaagcca tcgttctgct ggacccggaa     900
ggccatccgg tgttatggg tattgtggcc tctcgcatcc tggaagcgac cctgcgcccg     960
gtctttctgg tggcccaggg caaaggcacc gtgcgttcgc tggctccgat tccgccgtc    1020
gaagcactgc gcagcgcgga agatctgctg ctgcgttatg gtgtcataa gaagcggcg    1080
ggtttcgcaa tggatgaagc gctgtttccg gcgttcaaag cacgcgttga agcgtatgcc    1140
gcacgtttcc cggatccggt tcgtgaagtg cactgctgg atctgctgcc ggaaccgggc    1200
ctgctgccgc aggtgttccg tgaactggca ctgctggaac cgtatggtga aggtaacccg    1260
gaaccgctgt cctg                                                      1275
```

<210> SEQ ID NO 10
<211> LENGTH: 425
<212> TYPE: PRT
<213> ORGANISM: Thermus thermophilus

<400> SEQUENCE: 10

```
Met Phe Arg Arg Lys Glu Asp Leu Asp Pro Pro Leu Ala Leu Leu Pro
1               5                   10                  15
Leu Lys Gly Leu Arg Glu Ala Ala Ala Leu Leu Glu Glu Ala Leu Arg
            20                  25                  30
Gln Gly Lys Arg Ile Arg Val His Gly Asp Tyr Asp Ala Asp Gly Leu
        35                  40                  45
Thr Gly Thr Ala Ile Leu Val Arg Gly Leu Ala Ala Leu Gly Ala Asp
    50                  55                  60
Val His Pro Phe Ile Pro His Arg Leu Glu Glu Gly Tyr Gly Val Leu
```

Met Glu Arg Val Pro Glu His Leu Glu Ala Ser Asp Leu Phe Leu Thr
                85                  90                  95

Val Asp Cys Gly Ile Thr Asn His Ala Glu Leu Arg Glu Leu Leu Glu
            100                 105                 110

Asn Gly Val Glu Val Ile Val Thr Asp His His Thr Pro Gly Lys Thr
            115                 120                 125

Pro Pro Pro Gly Leu Val Val His Pro Ala Leu Thr Pro Asp Leu Lys
130                 135                 140

Glu Lys Pro Thr Gly Ala Gly Val Ala Phe Leu Leu Leu Trp Ala Leu
145                 150                 155                 160

His Glu Arg Leu Gly Leu Pro Pro Leu Glu Tyr Ala Asp Leu Ala
                165                 170                 175

Ala Val Gly Thr Ile Ala Asp Val Ala Pro Leu Trp Gly Trp Asn Arg
            180                 185                 190

Ala Leu Val Lys Glu Gly Leu Ala Arg Ile Pro Ala Ser Ser Trp Val
            195                 200                 205

Gly Leu Arg Leu Leu Ala Glu Ala Val Gly Tyr Thr Gly Lys Ala Val
210                 215                 220

Glu Val Ala Phe Arg Ile Ala Pro Arg Ile Asn Ala Ala Ser Arg Leu
225                 230                 235                 240

Gly Glu Ala Glu Lys Ala Leu Arg Leu Leu Leu Thr Asp Asp Ala Ala
                245                 250                 255

Glu Ala Gln Ala Leu Val Gly Glu Leu His Arg Leu Asn Ala Arg Arg
            260                 265                 270

Gln Thr Leu Glu Glu Ala Met Leu Arg Lys Leu Leu Pro Gln Ala Asp
            275                 280                 285

Pro Glu Ala Lys Ala Ile Val Leu Leu Asp Pro Glu Gly His Pro Gly
            290                 295                 300

Val Met Gly Ile Val Ala Ser Arg Ile Leu Glu Ala Thr Leu Arg Pro
305                 310                 315                 320

Val Phe Leu Val Ala Gln Gly Lys Gly Thr Val Arg Ser Leu Ala Pro
                325                 330                 335

Ile Ser Ala Val Glu Ala Leu Arg Ser Ala Glu Asp Leu Leu Leu Arg
            340                 345                 350

Tyr Gly Gly His Lys Glu Ala Ala Gly Phe Ala Met Asp Glu Ala Leu
            355                 360                 365

Phe Pro Ala Phe Lys Ala Arg Val Glu Ala Tyr Ala Ala Arg Phe Pro
370                 375                 380

Asp Pro Val Arg Glu Val Ala Leu Leu Asp Leu Leu Pro Glu Pro Gly
385                 390                 395                 400

Leu Leu Pro Gln Val Phe Arg Glu Leu Ala Leu Leu Glu Pro Tyr Gly
                405                 410                 415

Glu Gly Asn Pro Glu Pro Leu Phe Leu
            420                 425

<210> SEQ ID NO 11
<211> LENGTH: 738
<212> TYPE: DNA
<213> ORGANISM: Bacteriophage

<400> SEQUENCE: 11
tccggaagcg gctctggtag tggttctggc atgacaccgg acattatcct gcagcgtacc      60
gggatcgatg tgagagctgt cgaacagggg gatgatgcgt ggcacaaatt acggctcggc     120

```
gtcatcaccg cttcagaagt tcacaacgtg atagcaaaac cccgctccgg aaagaagtgg    180
cctgacatga aaatgtccta cttccacacc ctgcttgctg aggtttgcac cggtgtggct    240
ccggaagtta acgctaaagc actggcctgg ggaaaacagt acgagaacga cgccagaacc    300
ctgtttgaat tcacttccgg cgtgaatgtt actgaatccc cgatcatcta tcgcgacgaa    360
agtatgcgta ccgcctgctc tcccgatggt ttatgcagtg acggcaacgg ccttgaactg    420
aaatgcccgt ttacctcccg ggatttcatg aagttccggc tcggtggttt cgaggccata    480
aagtcagctt acatggccca ggtgcagtac agcatgtggg tgacgcgaaa aaatgcctgg    540
tactttgcca actatgaccc gcgtatgaag cgtgaaggcc tgcattatgt cgtgattgag    600
cgggatgaaa agtacatggc gagttttgac gagatcgtgc cggagttcat cgaaaaaatg    660
gacgaggcac tggctgaaat tggttttgta tttgggggagc aatggcgatc tggctctggt    720
tccggcagcg gttccgga                                                  738
```

<210> SEQ ID NO 12
<211> LENGTH: 226
<212> TYPE: PRT
<213> ORGANISM: Bacteriophage

<400> SEQUENCE: 12

```
Met Thr Pro Asp Ile Ile Leu Gln Arg Thr Gly Ile Asp Val Arg Ala
1               5                   10                  15

Val Glu Gln Gly Asp Asp Ala Trp His Lys Leu Arg Leu Gly Val Ile
            20                  25                  30

Thr Ala Ser Glu Val His Asn Val Ile Ala Lys Pro Arg Ser Gly Lys
        35                  40                  45

Lys Trp Pro Asp Met Lys Met Ser Tyr Phe His Thr Leu Leu Ala Glu
    50                  55                  60

Val Cys Thr Gly Val Ala Pro Glu Val Asn Ala Lys Ala Leu Ala Trp
65                  70                  75                  80

Gly Lys Gln Tyr Glu Asn Asp Ala Arg Thr Leu Phe Glu Phe Thr Ser
                85                  90                  95

Gly Val Asn Val Thr Glu Ser Pro Ile Ile Tyr Arg Asp Glu Ser Met
            100                 105                 110

Arg Thr Ala Cys Ser Pro Asp Gly Leu Cys Ser Asp Gly Asn Gly Leu
        115                 120                 125

Glu Leu Lys Cys Pro Phe Thr Ser Arg Asp Phe Met Lys Phe Arg Leu
    130                 135                 140

Gly Gly Phe Glu Ala Ile Lys Ser Ala Tyr Met Ala Gln Val Gln Tyr
145                 150                 155                 160

Ser Met Trp Val Thr Arg Lys Asn Ala Trp Tyr Phe Ala Asn Tyr Asp
                165                 170                 175

Pro Arg Met Lys Arg Glu Gly Leu His Tyr Val Val Ile Glu Arg Asp
            180                 185                 190

Glu Lys Tyr Met Ala Ser Phe Asp Glu Ile Val Pro Glu Phe Ile Glu
        195                 200                 205

Lys Met Asp Glu Ala Leu Ala Glu Ile Gly Phe Val Phe Gly Glu Gln
    210                 215                 220

Trp Arg
225
```

<210> SEQ ID NO 13
<211> LENGTH: 60

```
<212> TYPE: DNA
<213> ORGANISM: Artificial sequence
<220> FEATURE:
<223> OTHER INFORMATION: Oligonucleotide used in the Examples

<400> SEQUENCE: 13
cccccccccc cccccccccc cccccccccc cccccccccc cccccccccc cccccccccc      60

<210> SEQ ID NO 14
<211> LENGTH: 60
<212> TYPE: DNA
<213> ORGANISM: Artificial sequence
<220> FEATURE:
<223> OTHER INFORMATION: Oligonucleotide used in the Examples

<400> SEQUENCE: 14
aaaaaaaaaa aaaaaaaaaa aaaaaaaaaa aaaaaaaaaa aaaaaaaaaa aaaaaaaaaa      60

<210> SEQ ID NO 15
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 15
cccccccccc cccccccccc cccccccccc cccccccccc                            40

<210> SEQ ID NO 16
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 16
cccccccccc cccccccccc cccccccccc cccccaaaaa                            40

<210> SEQ ID NO 17
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 17
cccccccccc cccccccccc cccccccccc aaaaaccccc                            40

<210> SEQ ID NO 18
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 18
cccccccccc cccccccccc cccccaaaaa cccccccccc                            40

<210> SEQ ID NO 19
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 19
```
cccccccccc cccccccccc aaaaaccccc cccccccccc        40

<210> SEQ ID NO 20
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 20
cccccccccc cccccaaaaa cccccccccc cccccccccc        40

<210> SEQ ID NO 21
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 21
cccccccccc cccccccccc cccccccccc cccacccccc        40

<210> SEQ ID NO 22
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 22
cccccccccc cccccccccc cccccccccc ccacccccccc       40

<210> SEQ ID NO 23
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 23
cccccccccc cccccccccc cccccccccc cacccccccc        40

<210> SEQ ID NO 24
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 24
cccccccccc cccccccccc cccccccccc acccccccccc       40

<210> SEQ ID NO 25
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 25
cccccccccc cccccccccc cccccccca cccccccccc        40

<210> SEQ ID NO 26
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 26
cccccccccc cccccccccc ccccccccac cccccccccc                         40

<210> SEQ ID NO 27
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 27
cccccccccc cccccccccc cccccccacc cccccccccc                         40

<210> SEQ ID NO 28
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 28
cccccccccc cccccccccc ccccccaccc cccccccccc                         40

<210> SEQ ID NO 29
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 29
cccccccccc cccccccccc cccccacccc cccccccccc                         40

<210> SEQ ID NO 30
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 30
cccccccccc cccccccccc ccccaccccc cccccccccc                         40

<210> SEQ ID NO 31
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 31
cccccccccc cccccccccc cccacccccc cccccccccc                         40

<210> SEQ ID NO 32
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 32
cccccccccc cccccccccc ccacccccccc cccccccccc                        40

```
<210> SEQ ID NO 33
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 33
cccccccccc cccccccccc caccccccccc cccccccccc                          40

<210> SEQ ID NO 34
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 34
cccccccccc cccccccccc accccccccc cccccccccc                           40

<210> SEQ ID NO 35
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 35
cccccccccc cccccccccc cccccccccc cgcccccccc                           40

<210> SEQ ID NO 36
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 36
cccccccccc cccccccccc cccccccccc cacccccccc                           40

<210> SEQ ID NO 37
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 37
cccccccccc cccccccccc cccccccccc ctcccccccc                           40

<210> SEQ ID NO 38
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 38
cccccccccc cccccccccc cccccccccc cccccccccc                           40

<210> SEQ ID NO 39
<211> LENGTH: 40
<212> TYPE: DNA
<213> ORGANISM: Artificial sequence
<220> FEATURE:
<223> OTHER INFORMATION: Oligonucleotide used in the Examples
```

<400> SEQUENCE: 39
cccccccccc cccccccccc cccccgccc ccccccccc              40

<210> SEQ ID NO 40
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 40
cccccccccc cccccccccc ccccccaccc ccccccccc              40

<210> SEQ ID NO 41
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 41
cccccccccc cccccccccc ccccctccc ccccccccc              40

<210> SEQ ID NO 42
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 42
cccccccccc cccccccccc ccccccccc ccccccccc              40

<210> SEQ ID NO 43
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 43
cccccccccc cccccccccc ccgccccccc ccccccccc              40

<210> SEQ ID NO 44
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 44
cccccccccc cccccccccc ccaccccccc ccccccccc              40

<210> SEQ ID NO 45
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 45
cccccccccc cccccccccc cctccccccc ccccccccc              40

<210> SEQ ID NO 46

```
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 46
cccccccccc cccccccccc cccccccccc cccccccccc                            40

<210> SEQ ID NO 47
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 47
actacctagt ttacgtaatc catctgaaca atgcagcatt                            40

<210> SEQ ID NO 48
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 48
actacctagt ttacgtaatc catctgtaca atgcagcatt                            40

<210> SEQ ID NO 49
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 49
actacctagt ttacgtaatc catctggaca atgcagcatt                            40

<210> SEQ ID NO 50
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 50
actacctagt ttacgtaatc catctgcaca atgcagcatt                            40

<210> SEQ ID NO 51
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 51
cccccccccc cccccccccc cccccccccc cccccccccc                            40

<210> SEQ ID NO 52
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 52
```
cccccccccc cccccccccc cccccctccc cccccccccc        40

<210> SEQ ID NO 53
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 53
cccccccccc cccccccccc cccccaccc cccccccccc        40

<210> SEQ ID NO 54
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 54
cccccccccc cccccccccc cccccgccc cccccccccc        40

<210> SEQ ID NO 55
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 55
cccccccccc cccccccccc cccccccccc ctccccccc        40

<210> SEQ ID NO 56
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 56
cccccccccc cccccccccc cccccccccc caccccccc        40

<210> SEQ ID NO 57
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 57
cccccccccc cccccccccc cccccccccc cgccccccc        40

<210> SEQ ID NO 58
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 58
cccccccccc cccccccccc cccccaccc ctccccccc        40

<210> SEQ ID NO 59
<211> LENGTH: 40
<212> TYPE: DNA

```
<213> ORGANISM: Artificial sequence
<220> FEATURE:
<223> OTHER INFORMATION: Oligonucleotide used in the Examples

<400> SEQUENCE: 59
cccccccccc cccccccccc ccccccaccc caccccccccc                         40

<210> SEQ ID NO 60
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 60
cccccccccc cccccccccc ccccccaccc cgccccccccc                         40

<210> SEQ ID NO 61
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 61
cccccccccc cccccccccc ccccccgccc ctccccccccc                         40

<210> SEQ ID NO 62
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 62
cccccccccc cccccccccc ccccccgccc cacccccccc                          40

<210> SEQ ID NO 63
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 63
cccccccccc cccccccccc ccccccgccc cgcccccccc                          40

<210> SEQ ID NO 64
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 64
cccccccccc cccccccccc cccccctccc ctcccccccc                          40

<210> SEQ ID NO 65
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 65
cccccccccc cccccccccc cccccctccc caccccccccc                         40
```

```
<210> SEQ ID NO 66
<211> LENGTH: 40
<212> TYPE: DNA
<213> ORGANISM: Artificial sequence
<220> FEATURE:
<223> OTHER INFORMATION: Oligonucleotide used in the Examples

<400> SEQUENCE: 66
cccccccccc cccccccccc ccccctccc cgcccccccc                                  40
```